US012133762B2

(12) United States Patent
Klingensmith et al.

(10) Patent No.: US 12,133,762 B2
(45) Date of Patent: Nov. 5, 2024

(54) THREE-DIMENSIONAL MODELING AND ASSESSMENT OF CARDIAC TISSUE

(71) Applicant: Board of Trustees of Southern Illinois University, Edwardsville, IL (US)

(72) Inventors: Jon Klingensmith, Carbondale, IL (US); Colin Gibbons, Glen Carbon, IL (US); Michaela Kulasekara, Glen Carbon, IL (US); Vu Quang Dinh, Edwardsville, IL (US)

(73) Assignee: Board of Trustees of Southern Illinois University, Edwardsville, IL (US)

( * ) Notice: Subject to any disclaimer, the term of this patent is extended or adjusted under 35 U.S.C. 154(b) by 215 days.

(21) Appl. No.: 17/730,380

(22) Filed: Apr. 27, 2022

(65) Prior Publication Data

US 2022/0370033 A1    Nov. 24, 2022

Related U.S. Application Data

(60) Provisional application No. 63/250,568, filed on Sep. 30, 2021, provisional application No. 63/184,492, filed on May 5, 2021.

(51) Int. Cl.
*A61B 8/08*        (2006.01)
*A61B 5/00*        (2006.01)
(Continued)

(52) U.S. Cl.
CPC ............ *A61B 8/085* (2013.01); *A61B 5/7275* (2013.01); *A61B 8/0858* (2013.01); *A61B 34/10* (2016.02);
(Continued)

(58) Field of Classification Search
CPC ..... A61B 8/085; A61B 5/7275; A61B 8/0858; A61B 34/10; A61B 2034/105; A61B 5/4872; A61B 5/7264; A61B 8/0883; A61B 8/466; A61B 8/483; A61B 8/5261; A61B 5/0044; G06T 7/0012; G06T 2207/30048; G06T 7/12; G06T 7/136; G06T 7/149; G06T 7/344; G06T 7/62; G06T 7/75; G06T 7/77; G06T 2207/10081;
(Continued)

(56) References Cited

PUBLICATIONS

Commandeur et al., Fully Automated CT Quantification of Epicardial Adipose Tissue by Deep Learning: A Multicenter Study, Radiology: Artificial Intelligence 2019 1:6.*

(Continued)

*Primary Examiner* — Bo Joseph Peng
(74) *Attorney, Agent, or Firm* — Greer, Burns & Crain, Ltd.; Steven P. Fallon

(57) ABSTRACT

A system for patient cardiac imaging and tissue modeling. The system includes a patient imaging device that can acquire patient cardiac imaging data. A processor is configured to receive the cardiac imaging data. A user interface and display allow a user to interact with the cardiac imaging data. The processor includes fat identification software conducting operations to interact with a trained learning network to identify fat tissue in the cardiac imaging data and to map fat tissue onto a three-dimensional model of the heart. A preferred system uses an ultrasound imaging device as the patient imaging device. Another preferred system uses an MRI or CT image device as the patient imaging device.

4 Claims, 41 Drawing Sheets

(51) Int. Cl.
*A61B 34/10* (2016.01)
*G06T 7/00* (2017.01)

(52) U.S. Cl.
CPC ...... *G06T 7/0012* (2013.01); *A61B 2034/105* (2016.02); *G06T 2207/30048* (2013.01)

(58) Field of Classification Search
CPC . G06T 2207/10088; G06T 2207/10132; G06T 2207/20072; G06T 2207/20076; G06T 2207/20081; G06T 2207/20084; G06T 2207/20101; G06T 2207/20104; G06T 2207/30061
See application file for complete search history.

(56) References Cited

PUBLICATIONS

Klingensmith et al., Three-dimensional modeling and assessment of cardiac adipose tissue distribution, Journal of Biomedical Graphics and Computing, 2018, vol. 8, No. 1, online Published, Jan. 15, 2018.*

Karlapalem et al., Classification of Cardiac Adipose Tissue Using Spectral Analysis of Ultrasound Radiofrequency Backscatter, Proceedings vol. 10955, Medical Imaging 2019: Ultrasonic Imaging and Tomography; 109550F (2019), online Mar. 15, 2019.*

Dydenko et al., Towards ultrasound cardiac image segmentation based on the radiofrequency signal, Medical Image Analysis 7 (2003) 353-367.*

Chen et al., Deep Learning for Cardiac Image Segmentation: A Review, Frontiers in Cardiovascular Medicine, Mar. 2020, vol. 7, Article 25.*

Harada et al., The different association of epicardial fat with coronary plaque in patients with acute coronary syndrome and patients with stable angina pectoris: Analysis using integrated backscatter intravascular ultrasound, Atherosclerosis, vol. 236, Issue 2, 2014, pp. 301-306, ISSN 0021-9150.*

Spearman, et al., "Prognostic Value of Epicardial Fat Volume Measurements by Computed Tomography: A Systematic Review of the Literature", Eur Radiol., 2015, vol. 25(11), pp. 3372-3381.

Strobl, et al., "Conditional variable importance for random forests", BMC Bioinformatics, 2008, vol. 9:307, pp. 1-11.

Taha, et al., "Metrics for evaluating 3D medical image segmentation: analysis, selection, and tool", BMC Medical Imaging, 2015, vol. 15:29, pp. 1-28.

Talman, et al., "Epicardial adipose tissue: far more than a fat depot", Cardiovascular Diagnosis and Therapy, 2014, vol. 4(6), pp. 416-429.

Thomas, et al., "Whole body fat: Content and distribution", Progress in Nuclear Magnetic Resonance Spectroscopy, 2013, vol. 73, pp. 56-80.

Thörmer, et al., "Software for Automated MRI-Based Quantification of Abdominal Fat and Preliminary Evaluation In Morbidly Obese Patients", Journal of Magnetic Resonance Imaging, 2013, vol. 37, pp. 1144-1150.

Tustison, et al., "N4ITK: Improved N3 Bias Correction", IEEE Transactions on Medical Imaging, 2010, vol. 29, No. 6, pp. 1310-1320.

Unberath, et al., "Open-Source 4D Statistical Shape Model of the Heart for X-Ray Projection Imaging", IEEE 12th International Symposium on Biomedical Imaging, 2015, pp. 739-742.

Van Der Walt, et al., "The NumPy Array: A Structure for Efficient Numerical Computation", Computing in Science & Engineering, 2011, pp. 22-30.

Van Der Walt, et al., "scikit-image: image processing in Python", PeerJ, 2014, 2:e453, pp. 1-18.

Van Gaal, et al., "Mechanisms linking obesity with cardiovascular disease", Nature, 2006, vol. 444, pp. 875-880.

Van Son, et al., "Intercostal Artery: Histomorphometric Study to Assess its Suitability as a Coronary Bypass Graft", Ann Thorac Surg, 1993, vol. 56, pp. 1078-1081.

Vogt, et al., "Parallel Acquisition Techniques for Accelerated Volumetric Interpolated Breath-Hold Examination Magnetic Resonance Imaging of the Upper Abdomen: Assessment of Image Quality and Lesion Conspicuity", Journal of Magnetic Resonance Imaging, 2005, vol. 21, pp. 376-382.

Wald, et al., "Automatic Quantification of Subcutaneous and Visceral Adipose Tissue From Whole-Body Magnetic Resonance Images Suitable for Large Cohort Studies", Journal of Magnetic Resonance Imaging, 2012, vol. 36, pp. 1421-1434.

Watson, et al., "Method agreement analysis: A review of correct methodology", Theriogenology, 2010, vol. 73, pp. 1167-1179.

Wear, et al., "High Resolution Ultrasonic Backscatter Coefficient Estimation Based on Autoregressive Spectral Estimation Using Burg's Algorithm", IEEE Transactions on Medical Imaging, 1994, vol. 13, No. 3, pp. 500-507.

Wear, et al., "A Comparison of Autoregressive Spectral Estimation Algorithms and Order Determination Methods in Ultrasonic Tissue Characterization", IEEE Transactions on Ultrasonics, Ferroelectrics, and Frequency Control, 1995, vol. 42, No. 4, pp. 709-716.

Wile, et al., "Magnetic Resonance Imaging of the Liver: Sequence Optimization and Artifacts", Magn Reson Imaging Clin N Am, 2010, vol. 18, pp. 525-547.

Williams, George, "Comparing the Joint Agreement of Several Raters with Another Rater", Biometrics, 1976, vol. 32, No. 3, pp. 619-627.

Wortsman, et al., "Clinical usefulness of variable-frequency ultrasound in localized lesions of the skin", J Am Acad Dermatol, 2010, vol. 62, No. 2, pp. 247-256.

Yaniv, et al., "SimpleITK Image-Analysis Notebooks: a Collaborative Environment for Education and Reproducible Research", J Digit Imaging, 2018, vol. 31, pp. 290-303.

Yavariabdi, et al., "Mapping and characterizing endometrial implants by registering 2D transvaginal ultrasound to 3D pelvic magnetic resonance images", Computerized Medical Imaging and Graphics, 2015, vol. 45, pp. 11-25.

Chelly, Jacques E., "Paravertebral Blocks", Anesthesiol Clin, 2012, vol. 30, pp. 75-90.

Cornier, et al., "Assessing Adiposity: A Scientific Statement From the American Heart Association", Circulation, 2011, vol. 124, pp. 1996-2019.

Cristobal-Huerta, et al., "Automated quantification of epicardial adipose tissue in Cardiac Magnetic Resonance Imaging", IEEE, 2015, pp. 7308-7311.

Crum, et al., "Generalized Overlap Measures for Evaluation and Validation in Medical Image Analysis", IEEE Transactions on Medical Imaging, 2006, vol. 25, No. 11, pp. 1451-1461.

Cullu, et al., "Does epicardial adipose tissue vol. provide information about the presence and localization of coronary artery disease?", Anadolu Kardiyol Derg, 2015, vol. 15.

Despres, Jean-Pierre, "Body Fat Distribution and Risk of Cardiovascular Disease: An Update", Circulation, 2012, vol. 126, pp. 1301-1313.

Dixon, Thomas W., "Simple Proton Spectroscopic Imaging", Radiology, 1984, vol. 153, pp. 189-194.

Eckel, et al., "Preventing Cardiovascular Disease and Diabetes: A Call to Action From the American Diabetes Association and the American Heart Association", Circulation, 2006, vol. 113, pp. 2943-2946.

Eroglu, Serpil, "How do we measure epicardial adipose tissue thickness by transthoracic echocardiography?", Anatol J Cardiol, 2015, vol. 15, pp. 416-419.

Feleppa, et al., "Diagnostic Spectrum Analysis in Ophthalmology: A Physical Perspective", Ultrasound in Med & Biol., 1986, vol. 12, No. 8, pp. 623-631.

Fluchter, et al., "Volumetric Assessment of Epicardial Adipose Tissue With Cardiovascular Magnetic Resonance Imaging", Obesity, 2007, vol. 15, No. 4, pp. 870-878.

(56) References Cited

PUBLICATIONS

Georgiou, et al., "Tissue Characterization Using the Continuous Wavelet Transform Part I: Decomposition Method", IEEE Transactions on Ultrasonics, Ferroelectrics, and Frequency Control, 2001, vol. 48, No. 2, pp. 355-363.

Georgiou, et al., "Tissue Characterization Using the Continuous Wavelet Transform Part II: Application on Breast RF Data", IEEE Transactions on Ultrasonics, Ferroelectrics, and Frequency Control, 2001, vol. 48, No. 2, pp. 364-373.

Gerber, et al., "Radiation Dose and Safety in Cardiac Computed Tomography", Cardiol Clin, 2009, vol. 27(4), pp. 665-677.

Glocker, et al., "Correction of Fat-Water Swaps in Dixon MRI", Lect. Notes Comput. Sci. 9902, 2016, pp. 536-543.

Gower, et al., "Procrustes Problems", Oxford University Press on Demand, 2004.

Haggard, et al., "Spectral analysis of ultrasound radiofrequency backscatter for the identification of five tissue ypes found in and around the paravertebral space", Proc. of SPIE, 2018, vol. 10580, pp. 1058016-1.

Hastie, et al., The Elements of Statistical Learning: Data Mining, Inference, and Prediction, Second Edition, Springer Science+ Business Media, LLC, 2009.

Hill, et al., "An automated segmentation for direct assessment of adipose tissue distribution from thoracic and abdominal Dixon-technique MR images", Proc. of SPIE, 2017, vol. 10133, pp. 1013315-1.

Homsi, et al., "3D-Dixon MRI based volumetry of peri- and epicardial fat", Int J Cardiovasc Imaging, 2016, vol. 32, pp. 291-299.

Hoogland, et al., "The Posterior Intercostal Vein: A Thermoregulatory Gateway to the Internal Vertebral Venous Plexus", Clinical Anatomy, 2013, vol. 26, pp. 735-740.

Hunter, John D., "Matplotlib: A 2D Graphics Environment", Computing in Science & Engineering, 2007, vol. 9(3), pp. 90-95.

Huttenlocher, et al., "Comparing Images Using the Hausdorff Distance", IEEE Transactions on Pattern Analysis and Machine Intelligence, 1993, vol. 15, No. 9, pp. 850-863.

Jacobellis, Gianluca, "Relation of Epicardial Fat Thickness to Right Ventricular Cavity Size in Obese Subjects", The American Journal of Cardiology, 2009, vol. 104, pp. 1601-1602.

Jacobellis, et al., "Epicardial adipose tissue: anatomic, biomolecular and clinical relationships with the heart", Nature Clinical Practice Cardiovascular Medicine, 2005, vol. 2, No. 10, pp. 536-543.

Jacobellis, et al., "Threshold Values of High-risk Echocardiographic Epicardial Fat Thickness", Obesity, 2008, vol. 16, pp. 887-892.

Jacobellis, et al., "Epicardial Fat from Echocardiography: A New Method for Visceral Adipose Tissue Prediction", Obesity Research, 2003, vol. 11, No. 2, pp. 304-310.

Insana, et al., "Describing small-scale structure in random media using pulse-echo ultrasound", J Acoust Soc Am., 1990, vol. 87(1), pp. 179-192.

Kanungo, et al., "An Efficient k-Means Clustering Algorithm: Analysis and Implementation", IEEE Transactions on Pattern Analysis and Machine Intelligence, 2002, vol. 24, No. 7, pp. 881-892.

Karlapalem, et al., "Classification of Cardiac Adipose Tissue Using Spectral Analysis of Ultrasound Radiofrequency Backscatter", Proceedings of SPIE Medical Imaging, 2019, 10955.

Kass, et al., "Snakes: Active Contour Models", International Journal of Computer Vision, 1988, vol. 1(4), pp. 321-331.

Kay, et al., "Spectrum Analysis—A Modern Perspective", Proceedings of the IEEE, 1981, vol. 69, No. 11, pp. 1380-1419.

Klingensmith, et al., "Spectral Analysis of Ultrasound Radiofrequency Backscatter for the Detection of Intercostal Blood Vessels", Ultrasound in Med. & Biol., 2018, vol. 44, No. 7, pp. 1411-1422.

Klingensmith, et al., "MRI-Based Three-Dimensional Modeling and Assessment of Epicardial Adipose Tissue Distribution", Proceedings of SPIE Medical Imaging, 2018, 105781P.

Klingensmith, et al., "Validation of an automated system for luminal and medial-adventitial border detection in three-dimensional intravascular ultrasound", The International Journal of Cardiovascular Imaging, 2003, vol. 19, pp. 93-104.

Klingensmith, et al., "Evaluation of Three-Dimensional Segmentation Algorithms for the Identification of Luminal and Medial-Adventitial Borders in Intravascular Ultrasound Images", IEEE Transactions on Medical Imaging, 2000, vol. 19, No. 10, pp. 996-1011.

Klingensmith, et al., "Development and evaluation of a method for segmentation of cardiac, subcutaneous, and visceral adipose tissue from Dixon magnetic resonance images", Journal of Medical Imaging, 2019, vol. 6(1), pp. 014004-1-014004-14.

Klingensmith, et al., "Automated segmentation of cardiac adipose tissue in Dixon magnetic resonance images", Journal of Biomedical Graphics and Computing, 2018, vol. 8, No. 1, pp. 1-13.

Klingensmith, et al., "Three-dimensional modeling and assessment of cardiac adipose tissue distribution", Journal of Biomedical Graphics and Computing, 2018, vol. 8, No. 1, pp. 14-28.

Kullberg, et al., "Automated and reproducible segmentation of visceral and subcutaneous adipose tissue from abdominal MRI", International Journal of Obesity, 2007, vol. 31, pp. 1806-1817.

Kumon, et al., "Spectral Analysis of Ultrasound Backscatter for Characterization of HIFU Lesions in Cardiac Tissue with High-Frequency Imaging", IEEE International Ultrasonics Symposium Proceedings, 2009, pp. 244-247.

Lang, et al., "The Use of a Nerve Simulator for Thoracic Paravertebral Block", Anesthesiology, 2002, vol. 97, No. 2, pp. 521-529.

Lang, et al., "Recommendations for Cardiac Chamber Quantification by Echocardiography in Adults: An Update from the American Society of Echocardiography and the European Association of Cardiovascular Imaging", European Heart Journal—Cardiovascular Imaging, 2015, vol. 16, pp. 233-271.

Lee, et al., "Two Algorithms for Constructing a Delaunay Triangulation", International Journal of Computer and Information Sciences, 1980, vol. 9, No. 3, pp. 219-242.

Lee, et al., "Adipose tissue heterogeneity: Implication of depot differences in adipose tissue for obesity complications", Molecular Aspects of Medicine, 2013, vol. 34, pp. 1-11.

Liou, et al., "Fully automated large-scale assessment of visceral and subcutaneous abdominal adipose tissue by magnetic resonance imaging", International Journal of Obesity, 2006, vol. 30, pp. 844-852.

Liu, et al., "Ultrasonic tissue characterization via 2-D spectrum analysis: theory and in vitro measurements", Med Phys., 2007, vol. 34(3), pp. 1037-1046.

Lizzi, et al., "Relationship of Ultrasonic Spectral Parameters to Features of Tissue Microstructure", IEEE Transactions on Ultrasonics, Ferroelectrics, and Frequency Control, 1986, vol. UFFC-33, No. 3, pp. 319-329.

Lizzi, et al., "Theoretical framework for spectrum analysis in ultrasonic tissue characterization", J. Acoust. Soc. Am., 1983, vol. 73(4), pp. 1366-1373.

Lönnqvist, et al., "Paravertebral blockade", Anaesthesia, 1995, vol. 50, pp. 813-815.

Lorenz, et al., "A comprehensive shape model of the heart", Medical Image Analysis, 2006, vol. 10, pp. 657-670.

Lorenzo-Valdés, et al., "Segmentation of 4D cardiac MR images using a probabilistic atlas and the EM algorithm", Medical Image Analysis, 2004, vol. 8, pp. 255-265.

Lötjönen, et al., "Statistical shape model of atria, ventricles and epicardium from short- and long-axis MR mages", Medical Image Analysis, 2004, vol. 8, pp. 371-386.

Marple, et al., "Digital Spectral Analysis with Applications", The Journal of the Acoustical Society of America, 1989, vol. 86(5), pp. 2043.

Mihl, et al., "Automated quantification of epicardial adipose tissue (EAT) in coronary CT angiography; comparison with manual assessment and correlation with coronary artery disease", Journal of Cardiovascular Computed Tomography, 2014, vol. 8, pp. 215-221.

Möller, et al., "Fast, Minimum Storage Ray/Triangle Intersection", J Graph Tools., 1997, pp. 1-7.

Moore, et al., "Characterization of coronary atherosclerotic morphology by spectral analysis of radiofrequency signal: in vitro

(56) References Cited

PUBLICATIONS intravascular ultrasound study with histological and radiological validation", Heart, 1998, vol. 79, pp. 459-467.

Nair, et al., "Regularized Autoregressive Analysis of Intravascular Ultrasound Backscatter: Improvement in Spatial Accuracy of Tissue Maps", IEEE Transactions on Ultrasonics, Ferroelectrics, and Frequency Control, 2004, vol. 51, No. 4, pp. 420-431.

Nair, et al., "Classification of Atherosclerotic Plaque Composition by Spectral Analysis of Intravascular Ultrasound Data", IEEE Ultrasonics Symposium, 2001, pp. 1569-1572.

Nair, et al., "'Blind' Data Calibration of Intravascular Ultrasound Data for Automated Tissue Characterization", IEEE Ultrasonics Symposium, 2004, pp. 1126-1129.

Abrahams, et al., "Evidence-Based Medicine: Ultrasound Guidance for Truncal Blocks", Regional Anesthesia and Pain Medicine, 2010, vol. 35, No. 2, Supplement 1, pp. S36-S42.

Acharya, et al., "Ultrasound-based tissue characterization and classification of fatty liver disease: A screening and diagnostic paradigm", Knowledge-Based Systems, 2015, vol. 75, pp. 66-77.

Addeman, et al., "Validation of Volumetric and Single-Slice MRI Adipose Analysis Using a Novel Fully Automated Segmentation Method", Journal of Magnetic Resonance Imaging, 2015, vol. 41, pp. 233-241.

Ahn, et al., "Relationship of epicardial adipose tissue by echocardiography to coronary artery disease", Heart, 2008, vol. 94: e7, pp. 1-6.

Akaike, Hirotugu, "Fitting Autoregressive Models For Prediction", Ann Inst Stat Math, 1969, vol. 21, pp. 243-247.

Alabousi, et al., "Evaluation of Adipose Tissue vol. Quantification with IDEAL Fat-Water Separation", Journal of Magnetic Resonance Imaging, 2011, vol. 34, pp. 474-479.

Alexopoulos, et al., "Epicardial adipose tissue and coronary artery plaque characteristics", Elsevier: Atherosclerosis, 2010, vol. 210, pp. 150-154.

Andrekute, et al., "Automatic Differential Diagnosis of Melanocytic Skin Tumors Using Ultrasound Data", 2016, vol. 42, pp. 2834-2843.

Bastarrika, et al., "Relationship Between Coronary Artery Disease and Epicardial Adipose Tissue Quantification at Cardiac CT: Comparison Between Automatic Volumetric Measurement and Manual Bidimensional Estimation", Academic Radiology, 2010, vol. 17, No. 6, pp. 727-734.

Bergstrom, et al., "Robust registration of point sets using iteratively reweighted least squares", Comput Optim Appl, 2014, vol. 58, pp. 543-561.

Bernard, et al., "Deep Learning Techniques for Automatic MRI Cardiac Multi-Structures Segmentation and Diagnosis: Is the Problem Solved?" IEEE Transactions on Medical Imaging, 2018, vol. 37, No. 11, pp. 2514-2525.

Bland, et al., "Statistical Methods For Assessing Agreement Between Two Methods of Clinical Measurement", The Lancet, 1986, vol. 327(8476), pp. 307-310.

Boezaart, et al., "Early Experience With Continuous Cervical Paravertebral Block Using a Stimulating Catheter", Regional Anesthesia and Pain Medicine, 2003, vol. 28, No. 5, pp. 406-413.

Bonekamp, et al., "Quantitative comparison and evaluation of software packages for assessment of abdominal adipose tissue distribution by magnetic resonance imaging", Int J Obes (Lond)., 2008, vol. 32(1), pp. 100-111.

Bornert, et al., "Water/Fat-Resolved Whole-Heart Dixon Coronary MRA: An Initial Comparison", Magnetic Resonance in Medicine, 2014, vol. 71, pp. 156-163.

Bradski, et al., "Learning OpenCV: Computer Vision with the OpenCV Library", O'Reilly Media, Inc., 2008.

Breiman, Leo, "Random Forests", Machine Learning, 2001, vol. 45, pp. 5-32.

Britton, et al., "Ectopic Fat Depots and Cardiovascular Disease", Circulation, 2011, vol. 124, pp. e837-e841.

Chalana, et al., "A Methodology for Evaluation of Boundary Detection Algorithms on Medical Images", IEEE Transactions on Medical Imaging, 1997, vol. 16, No. 5, pp. 642-652.

Chawla, et al., "A Class of Generalized Trapezoidal Formulas for the Numerical Integration of y'=f(x,y)", Intern. J. Computer Math, 1996, vol. 62, pp. 131-142.

Nair, et al., "Assessing Spectral Algorithms to Predict Atherosclerotic Plaque Composition with Normalized and Raw Intravascular Ultrasound Data", Ultrasound in Med. & Biol., 2001, vol. 27, No. 10, pp. 1319-1331.

Nakazato, et al., "Interscan reproducibility of computer-aided epicardial and thoracic fat measurement from honcontrast cardiac CT", Journal of Cardiovascular Computed Tomography, 2011, vol. 5, pp. 172-179.

Nguyen, et al., "Unbiased Feature Selection in Learning Random Forests for High-Dimensional Data", The Scientific World Journal, 2015, vol. 2015, pp. 1-18.

Nikolaou, et al., "Advances in cardiac CT imaging: 64-slice scanner", The International Journal of Cardiovascular Imaging, 2004, vol. 20, pp. 535-540.

Olshansky, et al., "A Potential Decline in Life Expectancy in the United States in the 21st Century", The New England Journal of Medicine, 2005, vol. 352;11, pp. 1138-1145.

Otsu, Nobuyuki, "A Threshold Selection Method from Gray-Level Histograms", IEEE Transactions on Systems, Man, and Cybernetics, 1979, vol. SMC-9, No. 1, pp. 62-66.

Painchaud, et al., "Cardiac MRI Segmentation with Strong Anatomical Guarantees", 2019, Medical Image Computing and Computer Assisted Intervention—MICCAI, 2019, pp. 632-640.

Pareek, et al., "Prostate Tissue Characterization/Classification in 144 Patient Population Using Wavelet and Higher Order Spectra Features from Transrectal Ultrasound Images", Technology in Cancer Research and Treatment, 2013, vol. 12, No. 6, pp. 545-557.

Parisi, et al., "Sleep disordered breathing and epicardial adipose tissue in patients with heart failure", Nutrition, Metabolism and Cardiovascular Diseases, 2017, pp. 1-24.

Park, et al., "Epicardial adipose tissue thickness is a predictor for plaque vulnerability in patients with significant coronary artery disease", Atherosclerosis, 2013, vol. 226, pp. 134-139.

Peng, et al., "Ultrasound-Guided Interventional Procedures in Pain Medicine: A Review of Anatomy, Sonoanatomy, and Procedures: Part I: Nonaxial Structures", Regional Anesthesia and Pain Medicine, 2009, vol. 34, No. 5, pp. 458-474.

Pérez, et al., "Applicability of Ultrasonic Tissue Characterization for Longitudinal Assessment and Differentiation of Calcification and Fibrosis in Cardiomyopathy", JACC, 1984, vol. 4, No. 1, pp. 88-95.

Piazzese, et al., "Evaluation of different statistical shape models for segmentation of the left ventricular endocardium from magnetic resonance images", Computing in Cardiology, 2015, vol. 42, pp. 105-108.

Postiano, et al., "An Accurate and Robust Method for Unsupervised Assessment of Abdominal Fat by MRI", Journal of Magnetic Resonance Imaging, 2004, vol. 20, pp. 684-689.

Pusch, et al., "Single-injection paravertebral block compared to general anaesthesia in breast surgery", Acta Anaesthesiol Scand, 1999, vol. 43, pp. 770-774.

Richardson, et al., "Thoracic paravertebral space location", Anaesthesia, 1996, vol. 51, pp. 137-139.

Rodrigues, et al., "Towards the Automated Segmentation of Epicardial and Mediastinal Fats: A Multi- Manufacturer Approach Using Intersubject Registration and Random Forest", IEEE International Conference on Industrial Technology (ICIT), 2015, pp. 1779-1785.

Sadeghi-Naini, et al., "Quantitative Ultrasound Evaluation of Tumor Cell Death Response in Locally Advanced Breast Cancer Patients Receiving Chemotherapy", Clinical Cancer Research, 2013, vol. 19(8), pp. 2163-2174.

Silaghi, et al., "Is epicardial adipose tissue, assessed by echocardiography, a reliable method for visceral adipose tissue prediction?", Medical Ultrasonography, 2011, vol. 13, No. 1, pp. 15-20.

Spearman, et al., "Automated Quantification of Epicardial Adipose Tissue Using CT Angiography: Evaluation of a Prototype Software", Eur Radiol, 2014, vol. 24, pp. 519-526.

\* cited by examiner

FIG. 2A
FIG. 2B
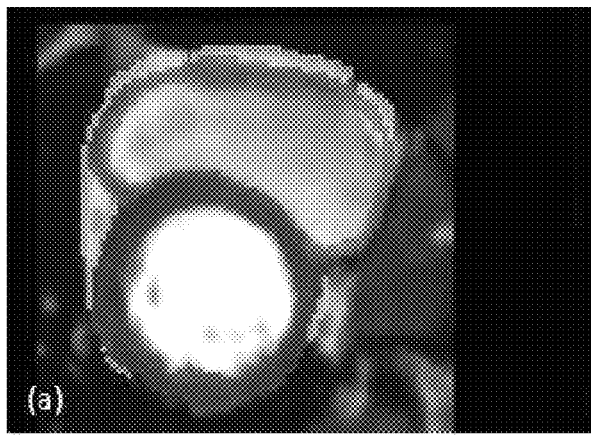
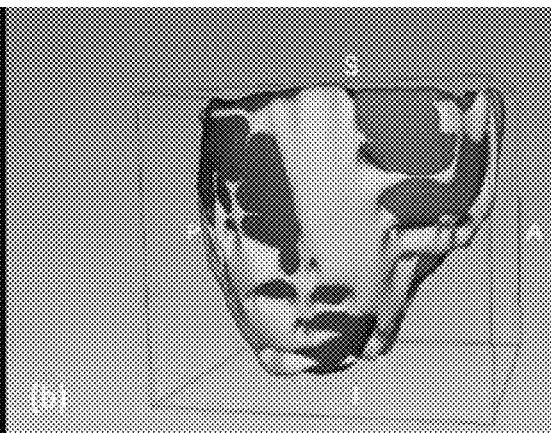
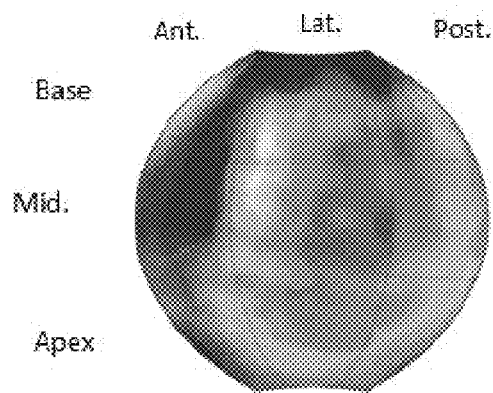
(c) Right-Heart Average Regional CAT Map
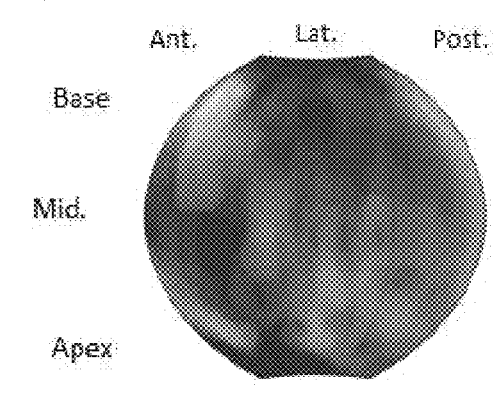
(d) Left-Heart Average Regional CAT Map
FIG. 2C
FIG. 2D

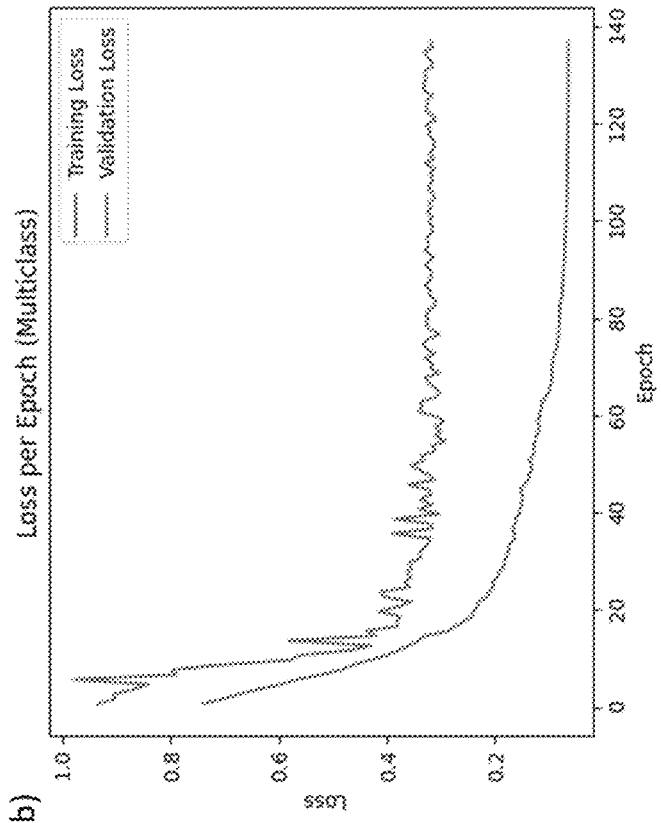
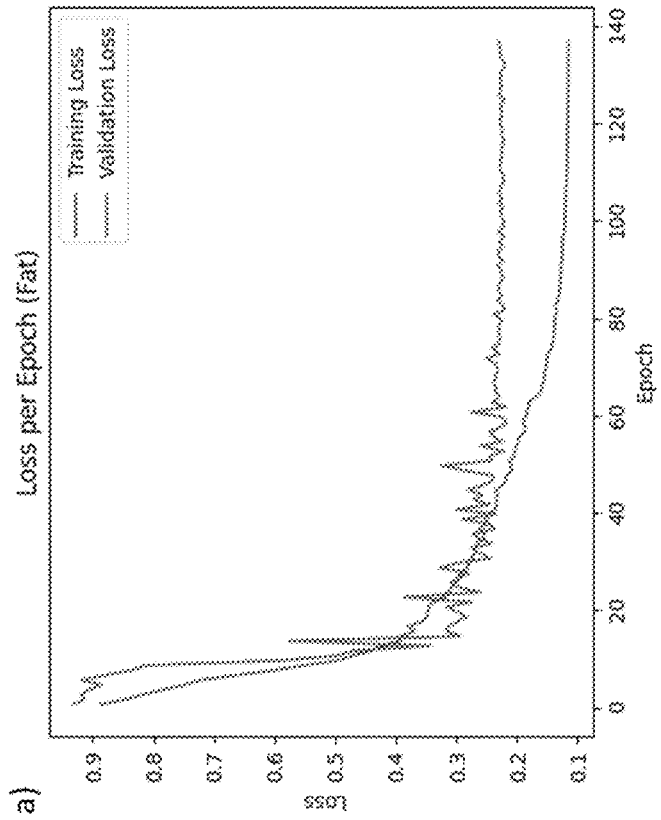
FIG. 16B
FIG. 16A

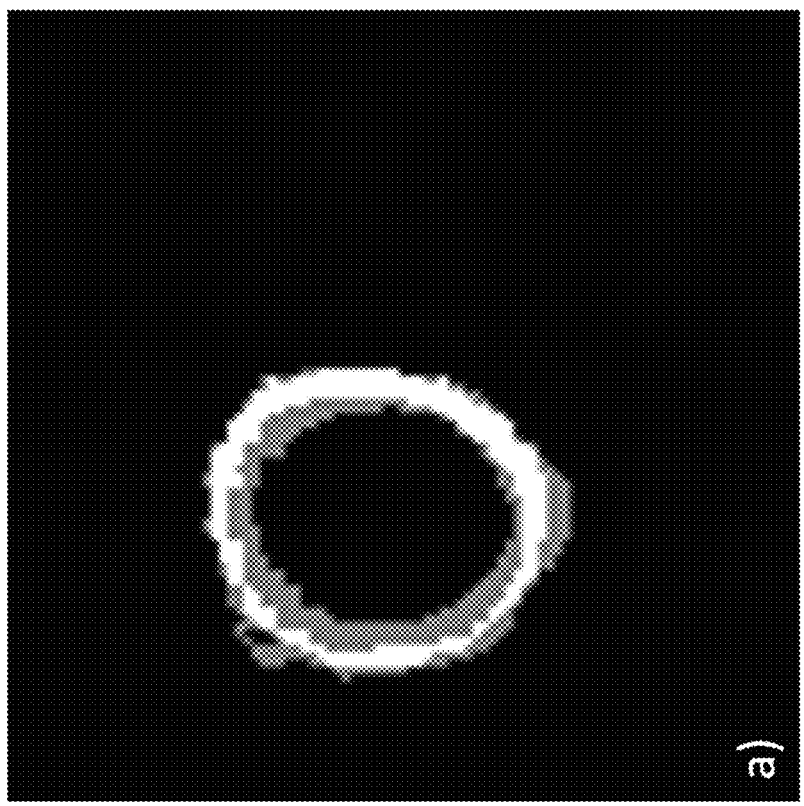
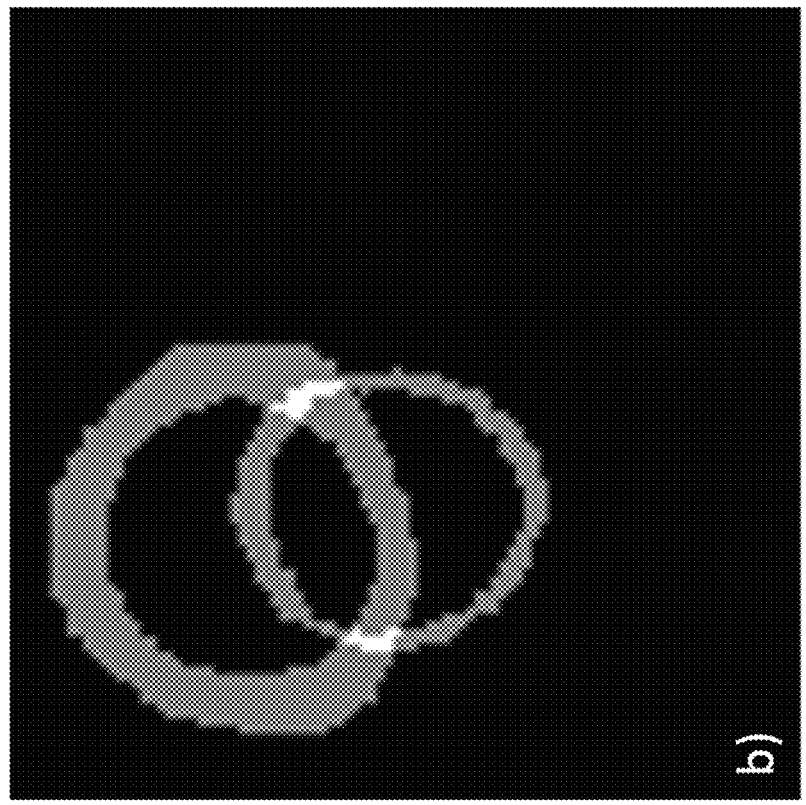
FIG. 22A
FIG. 22B

THREE-DIMENSIONAL MODELING AND ASSESSMENT OF CARDIAC TISSUE

PRIORITY CLAIM AND REFERENCE TO RELATED APPLICATION

The application claims priority under 35 U.S.C. § 119 and all applicable statutes and treaties from prior U.S. provisional application Ser. No. 63/184,492 which was filed May 5, 2021 and from U.S. provisional application Ser. No. 63/250,568 which was filed Sep. 30, 2021, which applications are incorporated by reference herein.

STATEMENT REGARDING FEDERALLY SPONSORED RESEARCH OR DEVELOPMENT

This invention was made with government support under Project Number 1R15HL145576-01A1 awarded by the National Institutes of Health. The government has certain rights in the invention.

FIELD OF THE INVENTION

The present invention relates to a method and apparatus for generating three-dimensional images of the heart, and more particularly, to a method and apparatus for generating a three-dimensional image of the heart using two-dimensional echocardiograms without requiring a separate three-dimensional image photographing apparatus for the purpose of volumetric assessment of cardiac adipose tissue.

BACKGROUND OF THE INVENTION

Obesity continues to be one of the most important health issues of our time and is a significant risk factor for cardiovascular disease. A layer of fat called epicardial adipose tissue (EAT) forms between the myocardium and visceral pericardium. In addition, pericardial adipose tissue (PAT) forms between the visceral and parietal pericardium. This combined fat deposit, called the cardiac adipose tissue (CAT), directly influences the development of coronary artery disease (CAD). Therefore, measuring the volume and distribution of CAT can be a marker for coronary artery disease and has become an important task for cardiovascular risk assessment.

Cardiac magnetic resonance imaging (MRI) can provide a three-dimensional (3D) assessment of CAT, but the procedure is expensive, time-consuming, and is only available at large institutions. Efforts to automate the analysis have helped reduce the burden and have improved the ability to measure CAT volume via MRI, but studies using MRI for assessment of CAT volume on CAD are limited to large research facilities or hospitals with the appropriate MRI capabilities. Echocardiography can also be used to quantify CAT but is significantly limited due to the fact that echocardiographic images only give information related to the intensity reflected by the tissue.

SUMMARY OF THE INVENTION

A preferred embodiment provides a system for patient cardiac imaging and tissue modeling. The system includes a patient imaging device that can acquire patient cardiac imaging data. A processor is configured to receive the cardiac imaging data. A user interface and display allows a user to interact with the cardiac imaging data. The processor includes fat identification software conducting operations to interact with a trained learning network to identify fat tissue in the cardiac imaging data and to map fat tissue onto a three-dimensional model of the heart. A preferred system uses an ultrasound imaging device as the patient imaging device. Another preferred system uses an MRI or CT image device as the patient imaging device.

The various preferred embodiments disclosed herein concern a system for echocardiographic assessment of CAT volume and distribution. Preferred applications include automated diagnostic tools that create and analyze fat maps to make predictions about the presence and type of coronary artery disease.

BRIEF DESCRIPTION OF THE DRAWINGS

FIGS. 2A-2D show a 3D CAT mapping according to an example modelling technique with (A) example segmented image, (B) 3D model, and Hammer projections of the average (C) right and (D) left side fat maps.

FIGS. 16A and 16B show calculated Dice loss of the 3D U-net for (A) each individual predicted class (B) weighted total of all predicted classes for both training and validation data at each epoch.

FIGS. 22A-22B show intersected contours from the shape model left myocardium filled-in with pixels for comparison to the left-myocardium-labeled pixels from the convolutional network.

DETAILED DESCRIPTION OF THE INVENTION

Figure 1A:
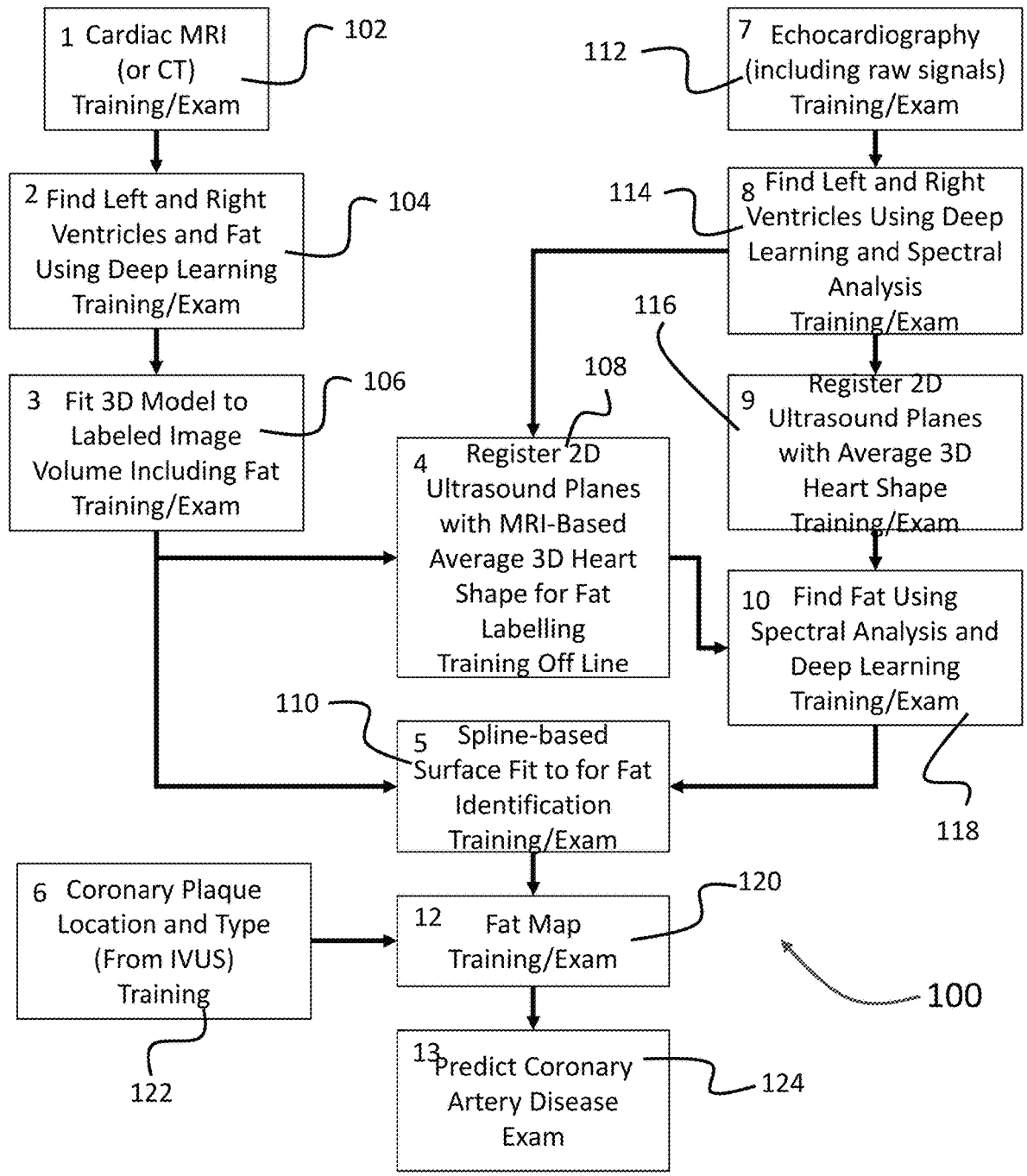
FIG. 1A is a flowchart illustrating steps in preferred imaging systems for detecting and mapping heart fat in patient images obtain from ultrasound or from one of MRI or CT.

Preferred embodiments of the invention provide methods and systems for non-invasive and inexpensive automated screening for cardiovascular disease. A patient being evaluated is imaged, via ultrasound or one of CT or MRI to obtain image data for automated analysis that can quantify and map fat. Preferred methods and systems also use the map data to estimate arterial lumen condition, with fat from the automated analysis, particularly in the area of the artery structures, being applied as a corollary for arterial lumen conditions.

Preferred methods and systems include machine learning analysis that was trained on MRI or CT data that establishes learning to distinguish fat in heart image data. Subsequent patient image data (from an ultrasound or from one of CT or MRI) is then processed to provide a surface model that fits the heart and allows the mapping of fat thickness in a two-dimensional coordinate system. An interface is provided that allows a practitioner to examine any selected portion of the image data that has been mapped into the two-dimensional coordinate system. The system automatically determines fat via a frequency analysis (when ultrasound is used for exam imaging and machine learning training) and the practitioner can therefore trace fat in close proximity to artery by going along the length when displaying the image data. When CT or MRI is used for exam imaging, then MRI data or CT data is also used for machine learning training.

In the ultrasound imaging example, fat is determined from a spectral analysis of frequency content (raw RF), which allows automated fat mapping from the spectral analysis that is not apparent in a B-mode picture. The analysis considers small portions of known tissue of the heart to access a database of fat and muscle, that was generated with an autoregressive model during training of the machine learning system, which allows the system to recognize fat and muscle. An acquired patient exam image plane is intersected with the prior developed average heart model from MRI or CT data. Preferred systems use ultrasound patient imaging as it provides a very inexpensive method to estimate coronary artery disease, including translation of a fat map to an estimate of artery plaque type.

In the CT or MRI imaging example, fat is determined from the imaging data based upon machine learning that was trained to find heart structures and label fat data in the imaging data. An acquired patient exam image plane is intersected with the prior developed average heart model from MRI or CT data via a spline-based fitting of patient image data that is surface fit to the average 3D model to identify fat. Preferred systems can also use the patient exam and system determined fat map estimate coronary artery disease, including translation of a fat map to an estimate of artery plaque type.

A preferred ultrasound exam image analysis processing uses spectral analysis to identify fat in an image plane. The fat map surface is then fitted to a 3D model and displayed via an interface that allows a practitioner to move through the model. The fitting is preferably via a trained deep learning network. Spectral signatures of fat are used from a database and the mapping can be smoothed as part of the fitting.

Preferred systems and methods can provide a CAT volume measurement system based on ultrasound alone. An ultrasound-based method for measuring CAT volume is used for each subject, resulting in pairs of volume measurements with one from the ultrasound-based system developed and one from the MRI. Agreement between the pairs of data is determined. Root mean square error (RMSE), the intraclass correlation (ICC), and the concordance correlation coefficient (CCC) can be calculated to consider both precision and accuracy for each pair of measurements and strong correlation with low error can be achieved with present methods.

Preferred methods and systems using ultrasound exam and training imaging address the relative sparsity of the ultrasound image planes when mapping to a heart model that was obtained from MRI and CT data. 3 PSAX image planes are commonly used, are easy to acquire, and have image planes that can be approximately orthogonal to the long axis of the 3D model. Using only 3 imaging planes can provide limited guidance on the deformation of the fat in the model to match the fat identified in the echocardiography. However, increasing the coverage of the surface of the heart can be achieved. The data from apical 2-chamber and 4-chamber views, and the data from the subcostal view, can be used to supplement the process of fusion, including the initial registration and the subsequent deformation.

Preferred embodiments of the invention will now be discussed with respect to experiments and drawings. Broader aspects of the invention can be understood by artisans in view of the general knowledge in the art and the description of the experiments that follows.

FIG. 1A illustrates a preferred method 100 for generating a 3D fat model of the heart, with options for acquiring patient exam image data from an ultrasound (step 112) or from one of an MRI or CT scan in step 102. In FIG. 1A, each step is indicated as training/exam, training, or exam to respectively indicate that the step is applicable to both training and exam, to training only or to exam only. In preferred systems, the machine learning continues to learn from patient exam data after being initial trained. Whether implemented in an ultrasound system or one of an MRI or CT system, the system has access to a trained deep learning network, which then during analysis of patient exam image data automatically finds the heart surfaces and fat of the acquired patient exam image data through the deep learning analysis in step 104. A 3D model of the heart is then fitted to a labelled image volume of the patient exam image data to include an identification of the fat in step 106. If applied to an MRI or CT system, then a spline-based fitting of patient exam image data is surface fit to the average 3D model to identify fat in step 110. If applied to an ultrasound system, then 2D ultrasound planes of patient image data are registered with the MRI or CT average heart shape (acquired during a learning phase) in step 108, providing known locations of fat from MRI or CT for labeling of fat in ultrasound for machine learning training. Learning is leveraged by either of steps 108 or 110. The learning for an ultrasound embodiment includes echocardiography that provides raw signals in step 112. A deep learning network finds heart surfaces in the 2D ultrasound from spectral analysis in step 114. Ultrasound 2D planes are then registered with average 3D heart image data (acquired from MRI or CT) in step 116. The deep learning network for ultrasound finds fat using spectral analysis in step 118. The fat thickness measurements across the heart surface model are used to make a fat map in step 120. A preferred optional step is to provide an estimate of arterial blockage by correlating the fat map to a database of coronary plaque obtained by intravascular ultrasound (IVUS) in step 122. This correlation can be used to provide an estimate of coronary artery disease in step 124.

Figure 1B:
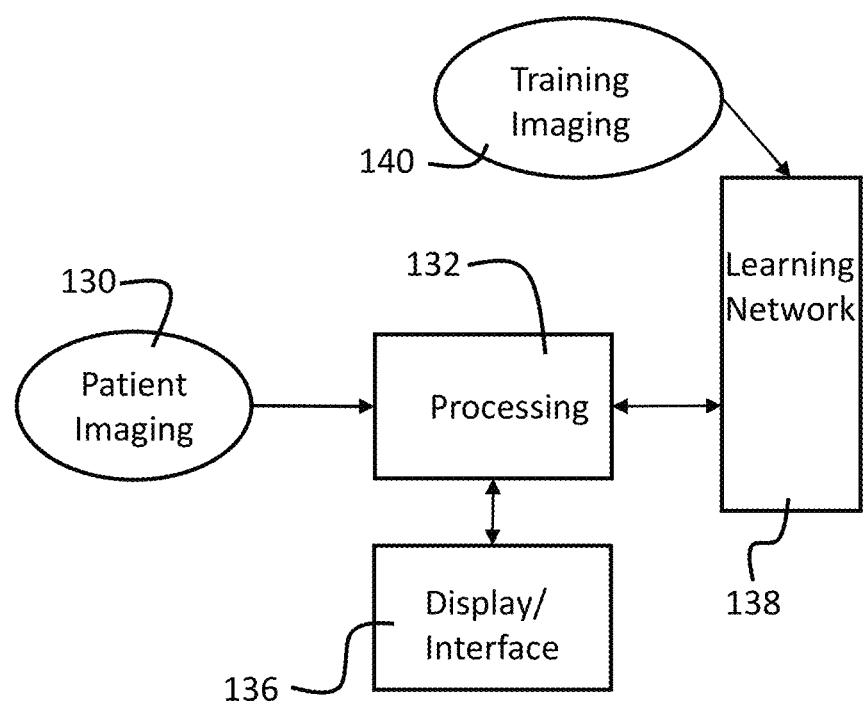
FIG. 1B is an example imaging system to implement the flowchart of FIG. 1.

FIG. 1B shows an example patient cardiac imaging system. A patient imaging device 130 can be an ultrasound or one of an MRI or CT imaging device. Processing 132 includes conventional image data processing to obtain image data from the device, and also includes software for the FIG. 1A processes. A display/interface 134 allows an operator to view imaging data and the fat maps and analysis produced by the FIG. 1A method, which relies upon a learning network 136 that is trained according to the FIG. 1A processes with training imaging data 138.

The basic FIG. 1A processes used trained deep learning to map heart fat from patient image data are better understood with respect to some preferred processes. These processes can be discussed now.

Preferred Process 1. Method of Creating a 3D Fat Model of the Heart from Cardiac MRI (Steps 102-120 and 112-118).

In a first preferred process, a method of creating a 3D fat model of the heart includes steps a-c of training and then steps d-g of analyzing patient exam image data:

a. Cardiac MRI data is first acquired using an MRI machine.
b. Manual tracing of cardiac MRI is performed using the labelled coronary artery data.
c. The manually-traced cardiac MRI data is used to train a deep fully convolutional network (or other machine learning network) to identify heart structures.
d. Cardiac fat pixels/voxels are labelled using the deep fully convolutional network.
e. An average heart shape model is fit to the labelled cardiac fat pixel/voxel data.
f. The average heart shape model fit to the labelled data is used to measure fat thickness across surface of the heart.
g. The measured fat thickness across the surface of the heart is used to create a 3D fat model of heart.

Preferred Process 2. Method of Creating a Cardiac Fat Map Using Patient Cardiac MRI or CT (Steps 102-110 and 120).

In a second preferred process, patient data is acquired and analyzed:

a. Cardiac MRI data from a patient is first acquired using an MRI or CT machine.
b. The coronary arteries are labelled using the MRI data acquired using an MRI machine.
c. The 3D fat model of heart is used in conjunction with the labelled coronary artery data to produce a fat map of the heart.

Preferred Process 3. Method of Creating a Cardiac Fat Map Using Echocardiography (Steps 112-118, 102-110, and 120).

The following steps are conducted:
a. The fat map of the heart obtained as discussed above is subject to a registration algorithm (e.g., Procrustes registration) and used to determine the optimal set of translation, scaling and rotation transformations to align the models and allow for the average cardiac fat map.
b. An average fat map is computed from the aligned 3D models obtained from the registration algorithm described immediately above.
c. The average fat map is used in conjunction with the 3D fat model as basis for a registration algorithm for the MRI-derived model with the ultrasound plane and is also used to incorporate the 3D fat model into an average shape model.
d. Echocardiography data for the heart is obtained.
e. Manual tracing of the 2D echocardiography data and manual selection of the region-of-interest is performed.
f. The spectral parameters are computed using the manually-traced 2D echocardiograph data and manually-selected region-of-interest.
g. The computed spectral parameters and the 3D fat model incorporated into the average shape model are used in conjunction with a trained, fully convolutional network for the purpose of fitting the average heart shape model to the labelled data.
h. The spectral parameters are used to build a random forest classifier. Other classifiers include, for example, neural networks and support vector machines.
i. The average heart shape model fitted to the labelled data and the random forest classifier are used to measure fat presence and thickness outside the surface outside the surface of the heart.
j. The measured fat presence and thickness outside the surface of the heart is used in multiple 3 parasternal short axis (PSAX) images to deform the 3D model.
k. The deformed 3D model is used to produce the cardiac fat map.

Preferred Process 4. Method of Assessing Cardiac Fat Volume Using Cardiac MRI and Echocardiography.

The 3D fat model of heart is used in conjunction with the fat map of the heart produced using either the Cardiac MRI method or the echocardiography data to assess cardiac fat volume.

Preferred Process 5. Method of Creating a Cardiac Fat Map and Assessing Cardiac Fat Volume (Steps 102-110 and 120) Using MRI.

The following steps are conducted:
a. An image of the heart is obtained using MRI.
b. The cardiac fat is segmented from the MRI fat-only image data using a series of image processing steps.
c. The labeled cardiac fat pixels in the image slices are used in conjunction with an advanced CAD software, such as Siemens NX, to model the heart.
d. The CAD software, such as Siemens NX, is used to produce a fat map of the heart and assess the fat volume of the heart.

Preferred Process 6. Method of Predicting Coronary Artery Disease Using the Cardiac Fat Map.

The following steps are conducted:
a. The cardiac fat map is used to quantify fat near the coronary arteries.
b. A supplementary imaging modality (e.g., intravascular ultrasound or intravascular optical coherence tomography) is used to obtain information about specific coronary plaque types.
c. The quantified fat near the coronary arteries is used in conjunction with the specific plaque information to train predictive algorithm.

Preferred Process 7. Method of Predicting Coronary Artery Disease Using Cardiac Fat Map Obtained from Cardiac MRI, Cardiac MRI or Echocardiography.

The following steps are performed:
a. The cardiac fat map is used to quantify fat near the coronary arteries.
b. The quantified fat near the coronary arteries is used in conjunction with trained algorithm to predict coronary artery disease.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and this can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1. Using Cardiac MRI to Model the Thickness and Distribution of Cardiac Adipose Tissue (CAT)

In this example, cardiac MRI data is acquired using an MRI machine such as the whole body 3.0 T MRI system (Vida, Siemens Medical Systems). The ECG-gated and respiratory-navigator-gated sequence is used to acquire volumes covering the entirety of the heart. Using volunteer subjects, the heart is imaged from apex to base at 1 cm increments in the cardiac short-axis. Volunteers provided the scan data, which will consist of two volumes, one from end-systole and one from end-diastole.

Figure 3:
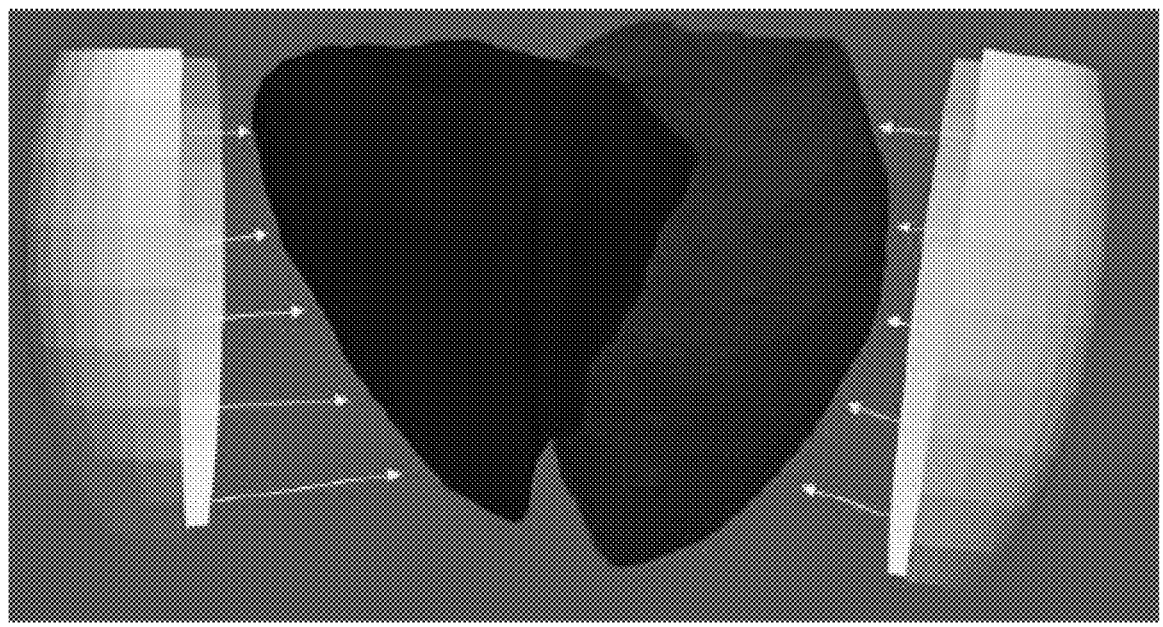
FIG. 3 provides an illustration of using two prolate-spheroid half-shells to map average fat thickness from the FIG. 2A-2D modelling technique onto an open-source heart model.

The cardiac image volumes of FIG. 2A can be segmented manually and 3D models of the fat can be created using the open-source 3DSlicer software, as shown in FIG. 2B. The thickness maps are generated as shown in FIGS. 2C and 2D. An open-source model that includes both the left and right sides of the heart can be used as the base on which to build the CAT model. The fat maps generated from the cardiac MRI data and manual segmentations can be used to compute an average thickness across the prolate-spheroidal coordinates ($\lambda$, $\varphi$) associated with the left and right sides. The mapping onto the open-source model can be performed by utilizing two prolate-spheroidal half shells that can be aligned manually with the base model, thereby providing the same 2D prolate-spheroidal coordinate mapping to each side of the heart and facilitating one-to-one correspondence between the fat maps and the surface of the model. At each location on the surface of the model, a normal can be computed and used with the fat thickness at that location. The resulting 3D points can be constructed into an average 3D fat surface model using the Delauney triangulation [Lee, D. T. et al., 1980]. Using both the fat map representation and building a triangulated surface, the variability in fat thickness can be accommodated. FIG. 3 provides an illustration of using two prolate-spheroid half-shells to map average fat thickness onto open-source heart model.

The 3D fat models are analyzed using cardiac-MRI-derived models and extended to produce fat maps from both the left and right sides of the heart. Two prolate-spheroidal surface segments, one for the right side and one for the left, were placed close to the inside surface of the 3D fat model. Normals to the surface were calculated and used to direct rays through the fat surface model. The intersection points of those rays with the surface were used to compute a fat thickness value for that coordinate pair in the prolate spheroidal coordinates ($\lambda$, $\varphi$) that represent the longitude and latitude. The fat thickness values across the 2D surface were then used to compute a Hammer projection, an equal-area mapping projection that reduces distortion when reducing a 3D surface to a 2D image map (FIG. 2C and FIG. 2D).

The present approach to 3D fat model construction provides a set of 2D coordinate pairs that parameterize the left and right sides of the surface of the heart, across which fat thicknesses are calculated. This mapping can be created with two prolate-spheroidal half-shells that are placed manually prior to fat thickness calculation. This is tedious and time consuming. A preferred approach is to register the two prolate-spheroid half-shells using the Iterative Closest Point (ICP) algorithm. After automated placement of the half-shells, the fat thickness calculation using the intersection of normals and the fat model can be performed in the same manner as is in the preliminary data.

After placement of the half-shells, the fat thickness calculation using the intersection of normals and the fat model can be performed. Each of the cardiac MRI scans acquired can be manually segmented or automatically segmented using the deep learning approach in Example 6 below. The resulting segmentations will include left ventricles, right ventricles, and fat. The ventricle segmentations can be used to aid in the fusion process. However, total volume can easily be computed from the fat segmentations and provide a suitable gold-standard data set with which to compare the ultrasound-derived volumes resulting from the new present approach. One approach is to produce two 3D models to be used during patient image analysis, one from end-systole and one from end-diastole, that represent the average CAT. These fat models can be incorporated onto the preexisting open-source model of the right and left sides of the heart and include the variation from a present set of training data scans.

Figure 4B:
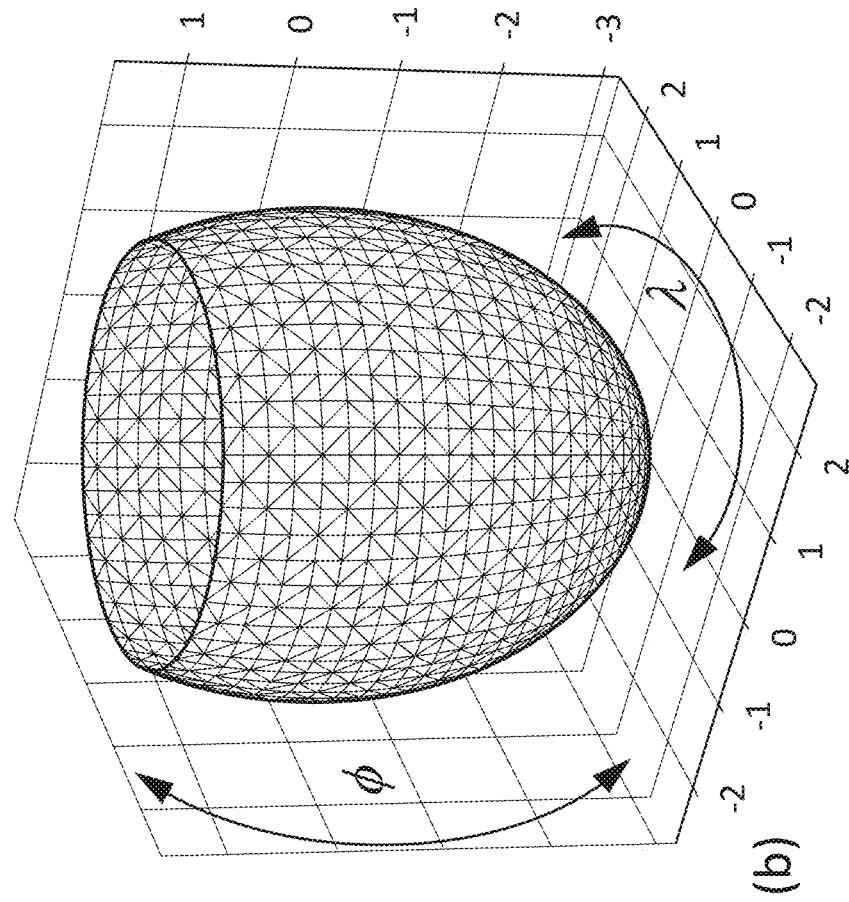
FIGS. 4A and 4B show an example polygon fat model, with points and triangle connectivity, is shown in (A) and a two-dimensional latitude and longitude ($\lambda$, $\varphi$) coordinate system using a prolate-spheroid is shown in (B).
Figure 4A:
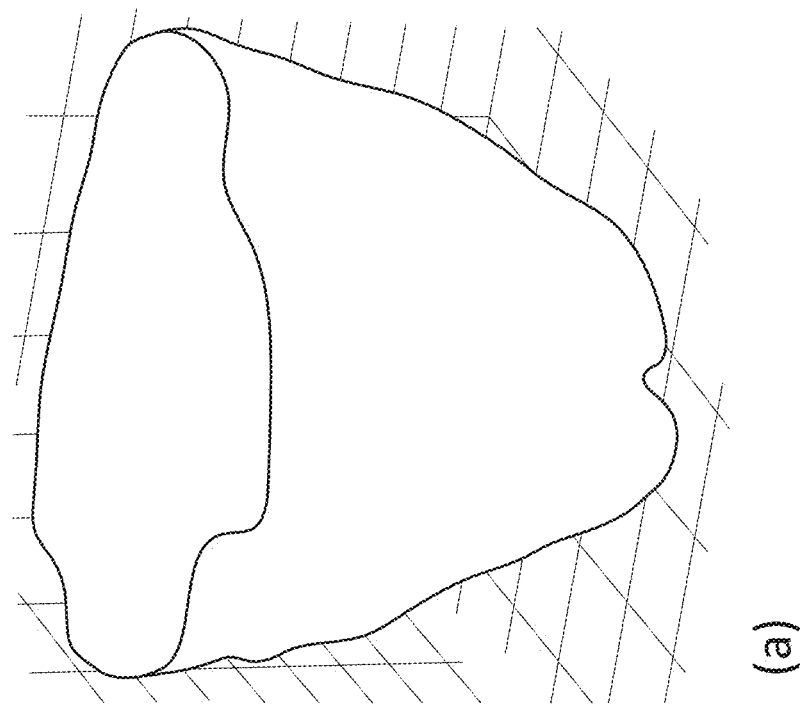

An alternative for automated registration of the prolate-spheroid half-shells is to use the fat thickness points to directly translate from 3D Cartesian coordinates (i.e., x, y, z) to a set of 2D prolate-spheroidal coordinates (i.e., $\lambda$, $\varphi$). This transformation can be calculated using the definition equations of prolate-spheroidal coordinates. A single parameterization (as shown in FIGS. 4A and 4B) would be used. However, in this approach, points on the "inside" of the fat model can be used to determine the appropriate latitude and longitude for that location. The corresponding triangles can be used to calculate normals that can intersect the fat model for the thickness calculation. Validation of the approaches can be performed in the same manner as with the preliminary data, by using the 3D printed models.

Figure 5:
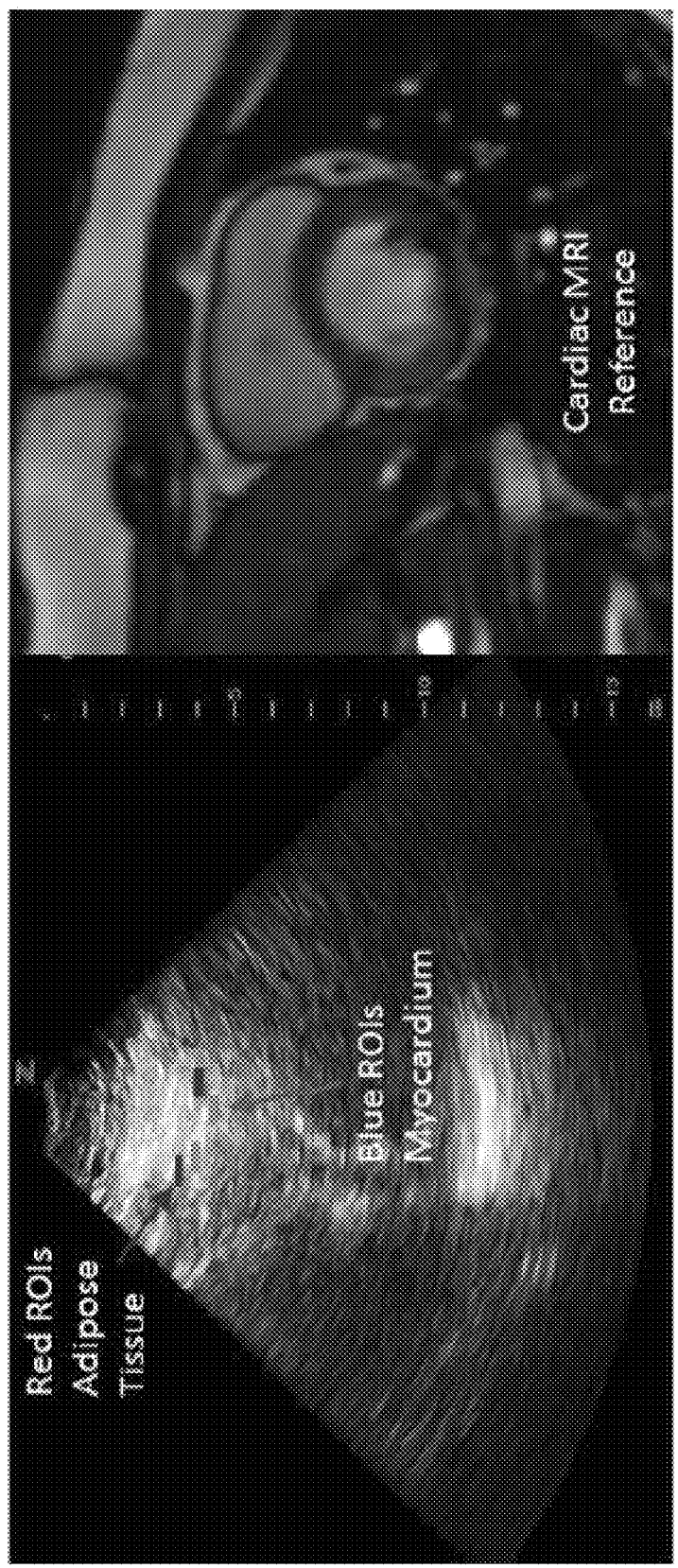
FIG. 5 shows an example of a short axis echocardiogram, with regions of adipose tissue and myocardium selected.

Example 2. An Automated Algorithm to Quantify and Characterize CAT Using Ultrasound Radiofrequency (RF) Backscattered Data An automated algorithm is provided to quantify and characterize CAT using ultrasound radiofrequency (RF) backscattered data. In this example, a Mindray Zonare ZS3 ultrasound system (Mindray North America, Mahwah, NJ) is used. The system is equipped with the cardiac P4-1c probe and the research software package for acquisition of the RF signals. The volunteer subjects for the cardiac MRI also underwent echocardiographic imaging with the modified system for RF signal acquisition. The echocardiography protocol included the acquisition of a standard set of image planes: a parasternal long axis (PLAX) image, and 3 PSAX images at the level of the mitral valve, papillary muscles, and near the apex. FIG. 5 shows an example of a short axis echocardiogram, with regions of adipose tissue and myocardium selected. The short axis cardiac MRI was used as reference when selecting the regions. For each image acquisition, the loops (and underlying raw data) recorded on the Zonare ZS3 system are stored and exported. The scan-converted images were reviewed, and regions-of-interest (ROIs) were identified in the CAT and in the myocardium. The ROIs are cross-referenced with the corresponding cardiac MRI image to ensure correct placement.

Figure 6:
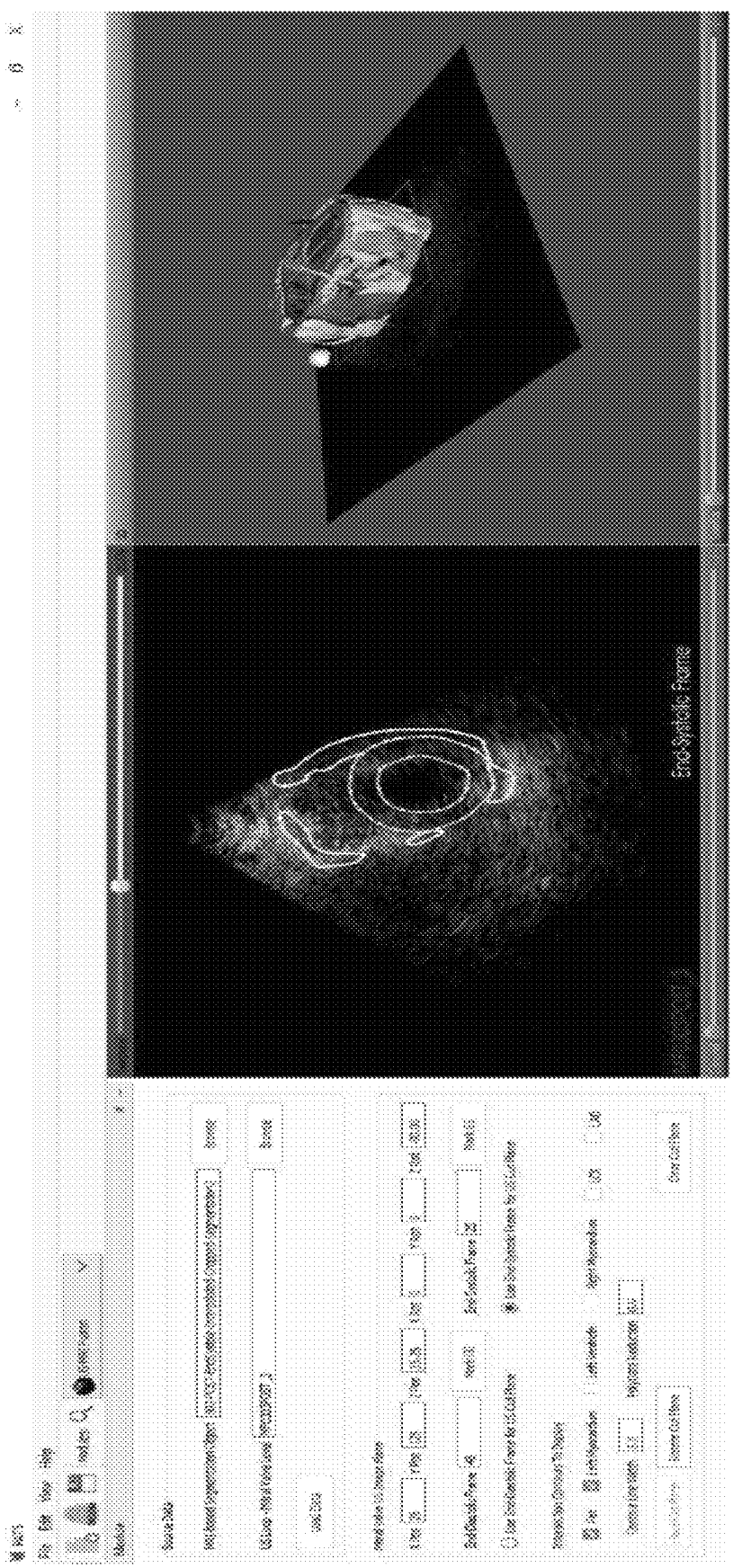
FIG. 6 shows a preferred user interface and screens of software of the invention that can use cardiac MRI to identify fat in ultrasound images. Left—user interface elements required for operation; Middle—example ultrasound image with contours from intersection of ultrasound image plane and MRI-derived 3D model; Right— MRI-derived 3D model and ultrasound image plane in same scene (white sphere denotes probe location).

Example ROIs, identified from the echocardiography, and confirmed with the MRI registration data, are shown in FIG. 6. The sections of the underlying raw RF signals that correspond to the ROIs selected, were identified and extracted for further processing. Because short-time signals are ill-suited for traditional Fourier-based techniques, an auto-regressive (AR) model was used to compute the frequency spectra for each of the short-record signals. The spectra for each line in each ROI are computed using an AR order corresponding to the number of samples in the ROI and averaged to form one spectra for the entire ROI, which was optimized to 15 via testing. In addition, the spectral data is also normalized using spectra from a tissue-mimicking phantom (Model 040GSE, CIRS, Inc., Norfolk, Virginia, 0.5 dB/cm-MHz side). This compensates for attenuation, diffraction, and the transmit and receive characteristics of the system. The depth and size of each ROI was used to obtain an ROI of the same depth and size from the data collected using the calibrated phantom. The spectra were calculated and averaged in the same way as with the tissue ROI data, resulting in one average PSD per ROI. The normalized PSD for each ROI was calculated by subtracting the reference phantom PSD of the same depth and size. A regression line was fit to the normalized spectra and 9 spectral parameters were computed.

These spectral parameters were used as the feature set to build a random forest classifier, a collection of classification trees that recursively partition the data based on the spectral parameters. Each tree is built with a random subset of the features and the resulting class is the tissue type that has the most votes from classification trees. As an example, fifty classification trees were used in this application. Data from 26 volunteer subjects were analyzed, resulting in 271 ROIs for CAT, 332 for myocardium, and 202 for blood. Seventy-five percent of the ROIs were used as training data and the remaining 25% were used as test data.

The main challenge in choosing the appropriate ROIs in the training image data is the identification of appropriate, gold-standard ROIs with known tissue types via visual identification of the layer of CAT in PSAX images. Collecting both the cardiac MRI and echocardiography from the same volunteers allows a unique approach to overcoming this limitation. Areas of CAT can be located on the ultrasound images by registering the ultrasound image plane with the 3D model derived from the associated cardiac MRI data. The endocardial boundary of the left ventricle can be traced manually (or automatically as provided in Example 14 below) in the parasternal short axis (PSAX) images ultrasound images. These contours from the ultrasound can serve as part of the validation for the segmentation algorithms. In addition, cardiac MRI can be manually segmented and the resulting surfaces form a 3D model, or automatically segmented via Example 6.

To fuse the two for identification of fat in the echocardiography, an image plane, representing the PSAX acquisition image plane, can be placed in the 3D scene. The LV contours resulting from this intersection of the plane and the model can be registered with the LV contours that were manually traced in the ultrasound. By aligning the two contours, the 3D position in space and the 3 rotational angles associated with the ultrasound imaging probe at the time of acquisition can be determined. The intersection of the fat from the MRI-derived 3D model and the registered image plane identifies locations of fat in the ultrasound images that may not otherwise be visible or identifiable in the traditional B-mode images. The registration can be performed using the ICP algorithm described in Example 13 for aligning the fat maps to the open-source heart model, but with the contour points instead of the surface points.

The process is illustrated in the screenshot shown in FIG. 6. The 3D scene on the right shows the 3D model derived from the MRI, the ultrasound image plane, and a small white sphere representing the location of the ultrasound probe at the time of imaging. The intersection of the image plane with the LV identified in the MRI images is shown as two labelled contours in the ultrasound image in the middle. In addition, the fat is illustrated in the 3D scene (colors are preferably used in the display to indicate fat though the image is grayscale in FIG. 6), also results in contours identifying fat in the ultrasound image. The registration can be performed using the LV as the basis, because it is the most easily identifiable object in both images. The underlying spectra, associated with the RF signals from the CAT as identified by this registration process, can be used to aid in training of the random forests and the deep learning models.

Figure 7:
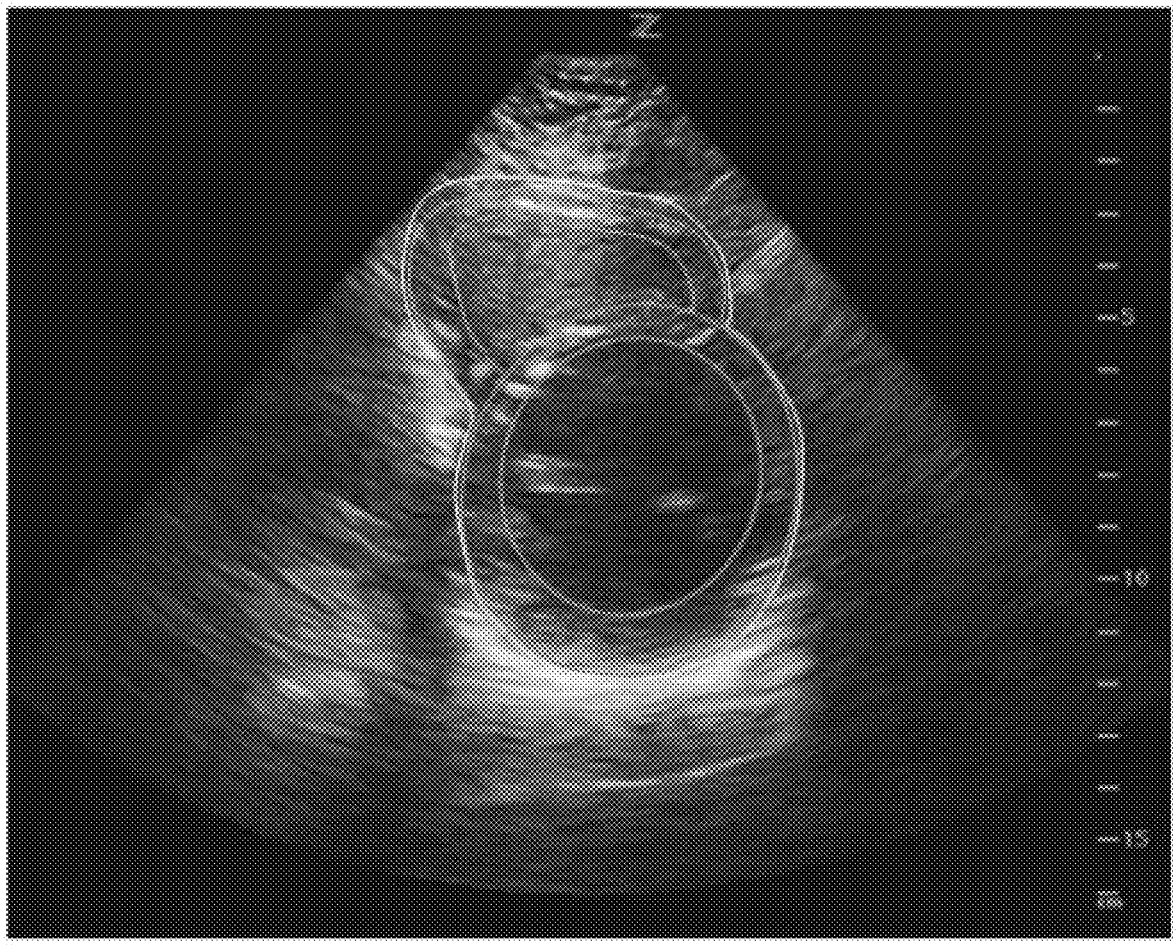
FIG. 7 shows an example of a preferred segmentation "template" structure, including initialization for left ventricle, right ventricle and adipose tissue (outer rings) if present.

To aid in registration of the ultrasound image planes with the MRI-derived 3D models, a semi-automated segmentation algorithm (or fully automated per Example 14) can identify the left ventricle, right ventricle, and CAT in the echocardiographic images. The inner and outer boundary of the left ventricle in PSAX views comprise two, concentric, closed contours. This approach targets the boundaries of the left ventricle with a set of dual contours, but also including the right ventricular myocardium as a modification. The first step of the semi-automated segmentation process is prompting a user to select points in the PSAX images to place the initial structure. An example, manually drawn set of boundaries can serve as the initial "template" for segmentation, is shown in FIG. 7. The second step of the process can be the optimization of the contours based on the expected shape, the radial edge content of the image data, and the tissue characterization algorithm based on spectral content of the raw data. The information derived from the spectral content can aid in identifying the boundary between blood and myocardium at the inner boundary and identifying the boundary between myocardium and any fat present on the outer boundary. This process is performed on the PSAX images acquired at the mitral valve level, the papillary muscle level, and the apex level, and on 2 image slices per loop from each—one at end-systole and one at end-diastole.

An alternative to the PSAX views is to use acquisitions from other acoustic windows. The first can be the subcostal view, where the probe is placed on the volunteer's abdomen and angled underneath the sternum and the rib cage, providing an image plane that penetrates the liver as the sound proceeds to the heart. The second can be an apical view—acquisitions can be made for both the traditional 4-chamber view and 2-chamber view from this acoustic window. The addition of these two views can provide more coverage of the myocardial surface. Should the segmentation of the PSAX images become challenging, the images from the subcostal and apical views can also provide orthogonal data to help guide segmentation in the PSAX views. One strategy is to initialize a structure in the apical 4-chamber view, which can be orthogonal to the PSAX views, and use the intersection of the contour from the apical view with the PSAX plane as a starting point or for additional shape constraint. Other strategies for mitigating segmentation challenges include the use of adjacent image slices from each recorded loop and the use of the correlation between image slices to aid in the process.

It is also possible to use an open-source model, supplemented with the 3D CAT model derived from using the cardiac MRI to model the thickness and distribution of the cardiac adipose tissue (CAT), to register the ultrasound imaging planes into the same coordinate set as the model. A surface-based registration algorithm can be used to align ultrasound image planes. The segmented CAT from the ultrasound imaging can be used to guide a deformation process to adjust the model and estimate the CAT volume under guidance from the 2D echocardiographic images.

Figure 8A:
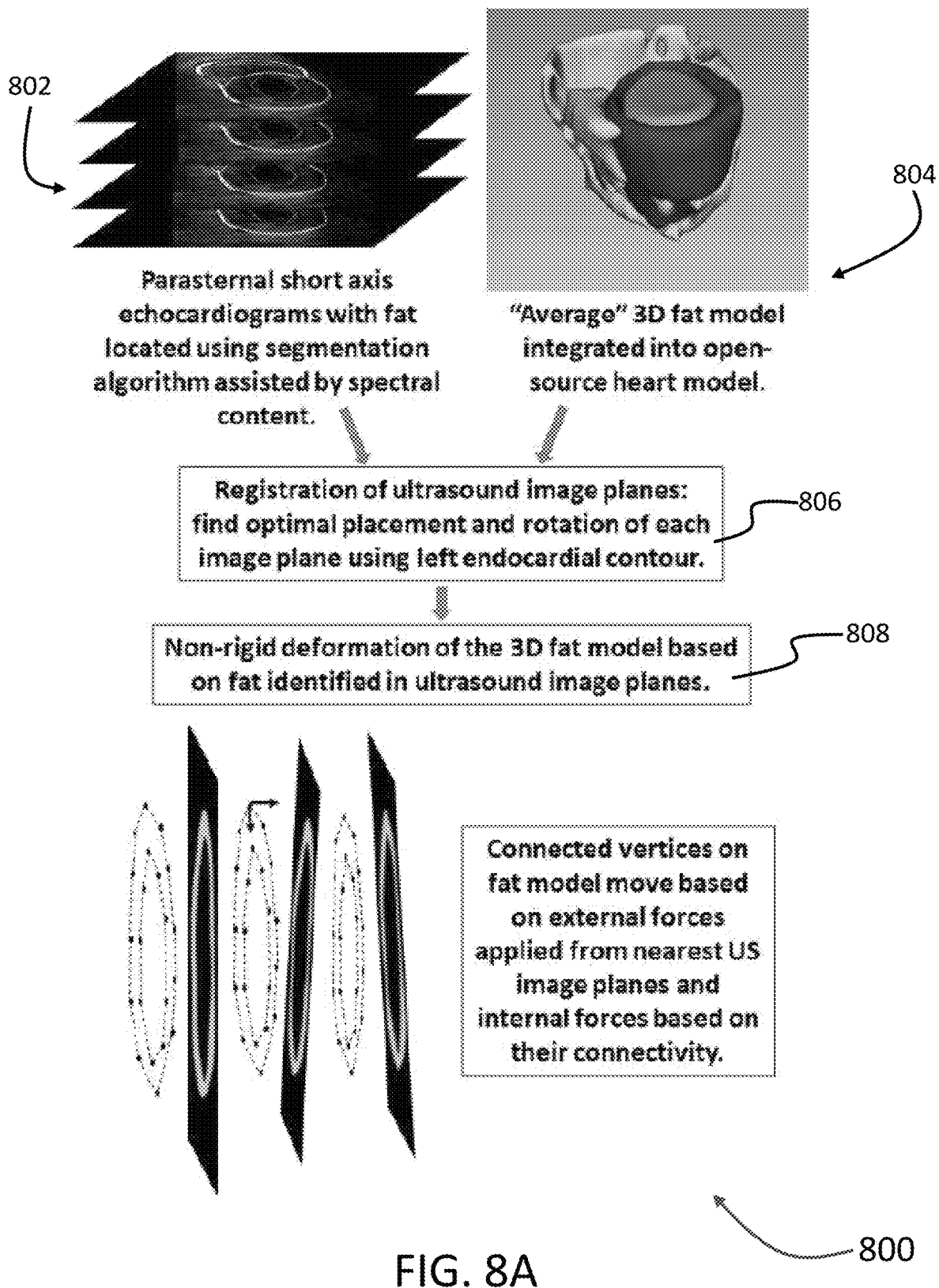
FIG. 8A shows a flowchart and illustration of preferred registration and fusion processes.
Figure 8B:
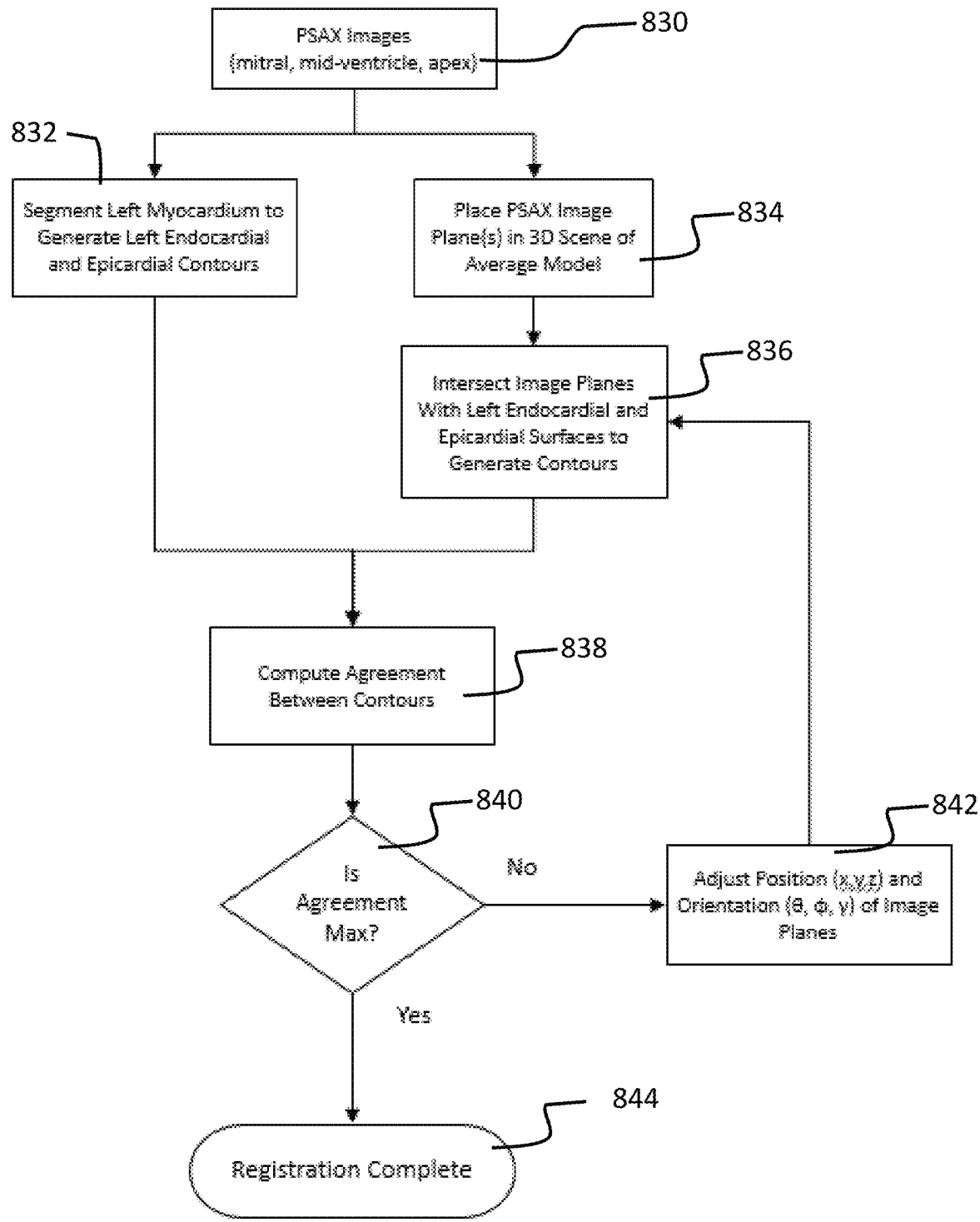
FIG. 8B shows a flowchart depicting the automatic registration algorithm using example parasternal short-axis (PSAX) ultrasound image.

FIGS. 8A and 8B illustrate a preferred registration process 800 and flowchart of the registration process 800. The process is illustrated with respect to parasternal short-axis (PSAX) view, but the algorithm operates with the same basic steps using other views such as parasternal long axis (PLAX), apical views, and subcostal views. The process of FIG. 8A includes a step 802 of obtaining patient data in the form of parasternal short axis echocardiograms and locating fat via the segmentation process of FIG. 8B, which is assisted by spectral content. Step 804 retrieves an average 3D fat model that has been integrated into an open-source heart model. Step 806 registers the ultrasound image planes to find optimal placement and rotation of each plane using the left endocardial contour from the 3D fat model and the patient data. Fitting is conducted in step 808 via non-rigid deformation of the 3D fat model based upon fat identified in the patient ultrasound image planes. Data is linked in step 800 to permit examination and manipulation of the images for display via connecting vertices on the fat model to move based upon external forces applied from the nearest ultrasound image planes and internal forces based upon their connectivity.

With regard to FIG. 8B, registration begins with the location of each of the 3 (or more) present image planes in step 830, namely mitral valve level, papillary muscle level, and apex level, will each involve the determination of 6 degrees of freedom–3 (x,y,z) coordinates for the location of the plane, and 3 angles of rotation ($\theta$, $\varphi$, $\gamma$) to provide the correct orientation. The segmented left endocardial contours provided in step 832 will serve as the main feature to use for registration by aligning the contours from the ultrasound image planes with the left endocardial surface of the open-source model. With the 3 PSAX image planes, and 6 degrees of freedom for each, there are a total of 18 parameters to place in step 834 the "search space" that require optimization. In step 834, the PSAX image planes are placed in the same 3D coordinate system as the average model. Intersected contours between the image planes and the average model are generated in step 836. The cost function for use in the registration algorithm can be based on point-to-point correspondence between the identified structures from the echocardiography and the model surfaces, as indicated by step 838. Many algorithms exist for minimizing cost functions and searching parameter spaces, but an ICP-based algorithm (iterative closest point algorithm) is preferred to solve the problem of sparse ultrasound planes requiring registration to a surface derived from 3D data. The agreement between the contours as computed in step 838 using ICP. The positions and orientations of the image planes are modified until the agreement between the contours is maximized (or the difference between the contours is minimized) in step 840. If the agreement is not minimized, the positions and orientations are modified in step 842. Then the contours are created again in step 836, their agreement is computed in step 838, and checked again in step 840. This process repeats itself until a minimum is reached and registration is complete 844.

After registration of the image planes to the model, the location of the fat in the image planes, as determined by the spectral analysis of the raw ultrasound signals, can be used to drive the deformation of the model using an active surface algorithm. The connected vertices of the fat model will iteratively move, based on external forces from the nearest ultrasound image planes and internal forces maintaining the connectivity of the model, until they converge to the "optimal" location. The optimization process for the deformation of the 3D average heart model can be an assessment of volume and distribution of CAT using only 2D echocardiography. This process can be repeated using both end-systolic and end-diastolic models for a more thorough characterization of the CAT dynamics.

Example 3. Three-Dimensional Modeling and Assessment of Cardiac Fat

In an experiment, the Cardiac technique was used to create sequences of registered set of in-phase (IP) and out-of-phase (OOP) image volumes to be used, to highlight adipose tissue by producing fat-only and water-only images. For the MRI acquisition, in this example coils were used to acquire MRI data from both the thoracic and abdominal cavities using a 3.0 T Skyra system (Siemens, Munich, Germany) and a multi-echo T1-weighted Volumetric Interpolated Breath-hold Examination (VIBE) 2-point Cardiac imaging sequence with a 20-second breath hold (TR/TE=3.97/1.23 ms, flip angle=9°). During image acquisition, subjects lay in a supine position, arms extended above their head, and support pillow beneath their knees. Image volumes with 120 slices (2.5 cm thick with 20% gap) and 320×260 pixels in each slice were acquired over a field-of-view (FOV) of 45 cm. Based on this geometry, the effective voxel size was 1.40625×1.40625×3.0 mm. The IP and OOP registered image volumes were used by the scanner software to reconstruct the fat-only and water-only images.

Figure 9:
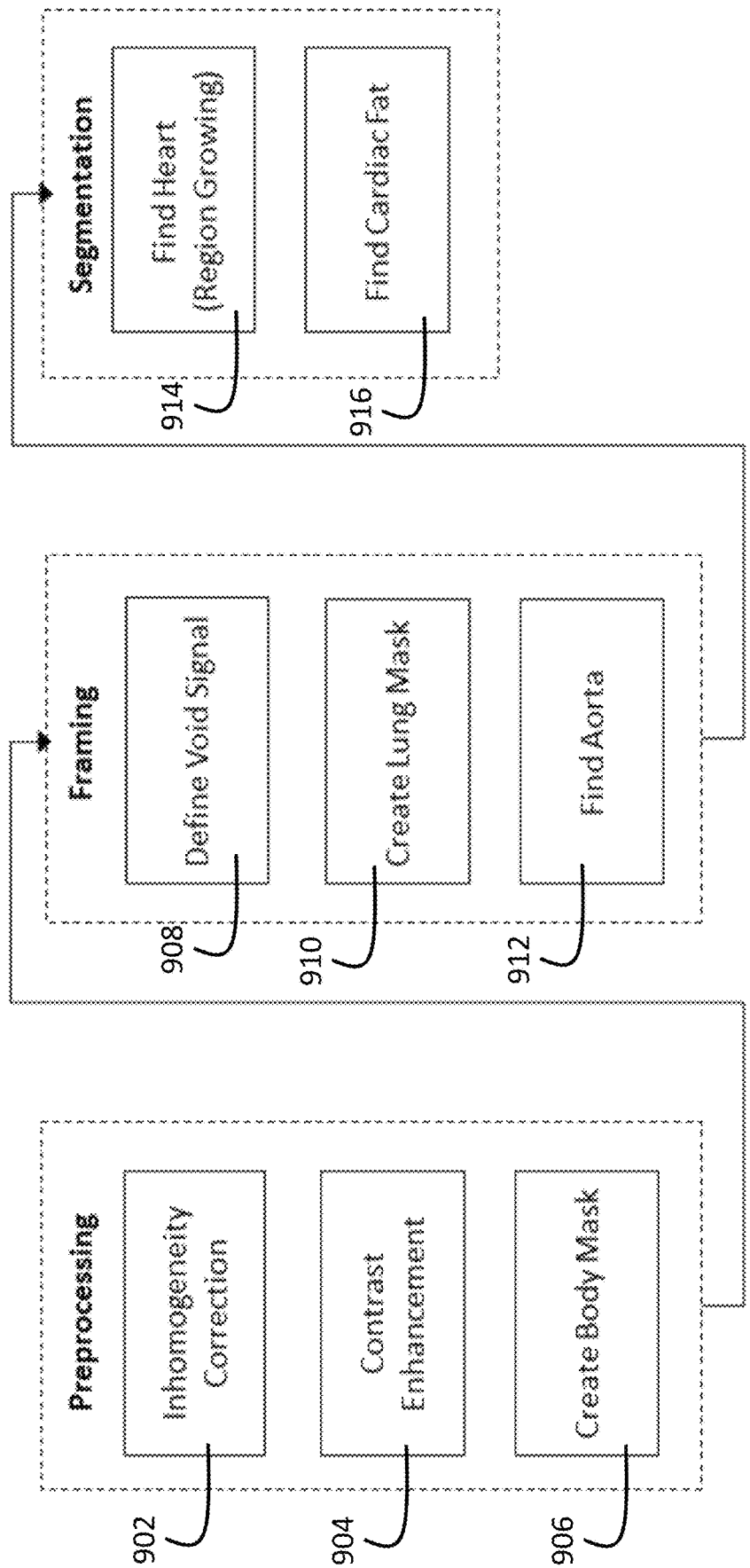
FIG. 9 shows a flowchart depicting a segmentation process for identifying the cardiac fat from Cardiac MRI image data.

In FIG. 9 cardiac fat segmentation of the Cardiac MRI images is performed on a slice-by-slice basis in three main steps: (1) preprocessing of the image data, (2) framing of the heart and the cardiac fat by identifying the lungs and aorta, and (3) segmentation of the heart and the cardiac fat. In step 902, the inhomogeneity field is estimated using a grayscale morphological closing operation with a large (~25% of the image size) circular structure element. After the inhomogeneity field was removed from the data, a histogram is calculated and then smoothed via median filtering. The smoothed histogram was used to enhance the contrast of both the water-only and fat-only images in step 904. The peak intensity was identified and assumed to be foreground. Values above this intensity were clipped and the remaining range was remapped to 256 gray levels, although a different number of levels can be used depending on the desired sensitivity. The final step in pre-processing was the use of the median-filtered histogram to determine a threshold for foreground and background signal intensities. The threshold was used to create a binary image from both the enhanced water-only and fat-only images. Then, a mask image was created from each using the corresponding water-only or fat-only threshold. The two masks were added together to create the body mask in step 906 and binary morphology was used to fill any internal holes.

In steps 908 and 910, an optimal threshold (via Otsu's method) was computed from the corrected image and used to create a binary mask for the lungs. The aorta was identified using a repeated series of binary dilation and fill operations beginning with a seed point in step 912. The lung mask and aorta were used to frame in an area for segmentation of the heart. A seed point, defined as the centroid of the region between the lungs and aorta, was used to locate the heart in step 914. However, at slices near the apex of the heart, the lungs are not present in the image slices. Therefore, in this set of slices, because the lungs are no longer in the images and they can't be used to frame the heart, the water-only image that has grayscale information from the diaphragm, liver, and heart was used to compute a Bayesian threshold between the higher gray-scale distributions of the diaphragm and liver and the lower distribution of the grayscale intensity of the heart. The convex hull of the resulting segmented heart was dilated to create a mask for the identification of the cardiac fat. Pixels in the fat-only image mask in the dilated convex hull region were labeled as CAT in step 916. Finally, contours outlining the CAT in each 2D image slice were extracted. The method provides segmentation of both the heart and the cardiac fat.

The contours extracted from the segmented heart were imported into NX10 (Siemens PLM Software, Plano, TX) and used to build the 3D heart models although other similar software can be used. First, a spline was fit to the in-plane contours, approximating the data points, but smoothing the shape and providing structure. The tradeoff between the closeness of fit to the data points and the smoothness of the spline contour was adjusted manually for each set of contours from each image slice. Through-plane guide curves were also extracted from the original data points (every 15 degrees) and used to give the model structure along the direction of the long axis. The process was repeated using the cardiac fat contours to create the model of the adipose tissue.

An algorithm for analyzing the quantity and distribution of cardiac fat uses the individual heart and fat models as inputs. The two major branches of the algorithm are a formulation of the average heart surface model and the computation of the average fat thickness across the surface of the heart for each data set. An average heart model can be created using Procrustes analysis, which determines the optimal set of translation, scaling, and rotation transformations to align a set of landmarks or points. The heart models were represented in polygonal format with a set of vertices and triangular faces. Given X as the set of vertices from one model and Y as the set of vertices from another, Procrustes analysis aims to minimize the following in a least-squares sense where $\|X\|$ is the Euclidean norm of X:

$$D(X,Y)=\|Y-\alpha X\beta+\delta\|^2 \quad (1)$$

X and Y are 3×k matrices (for three-dimensional Procrustes analysis) where k is the number of vertices. α is the scaling component (a scalar), β is the reflection and rotation component (a k×k matrix), and δ is the translation component (a 3×k matrix). Each of these, α, β, and δ are solved for via Procrustes analysis. Once the individual matrices for each model (α, β, and δ) were computed, they were applied to the heart models to scale, rotate, and translate them for alignment. After each of the heart models were registered, the average surface was computed by taking the mean location of each of the corresponding vertices from the heart models.

The other branch of the process involved the computation of the distribution of cardiac fat thickness across the surface of the heart for each individual model created. For this step, an iterative closest point (ICP) registration algorithm was used to determine the appropriate rotation and translation matrices. Traditional ICP algorithms involve a similar construct as is shown in Equation (1), but without the scaling component. In this algorithm, the optimal rotation and translation matrices are determined using an iterative approach where corresponding points between the reference model and the data model are determined using a distance metric for each iteration. The difference between the reference points and the model points, as modified by the present rotation and translation matrices, is minimized iteratively in a least-squared sense until the convergence criteria are met or a maximum number of iterations is reached. To limit the influence of outliers, it is preferred to re-weight the least-squares problem for each iteration. The translation and rotation matrices determined for each individual model (based on the same reference model for each) were applied to the vertices of the fat model to align them and create a common frame of reference for fat thickness computation.

Once registered to the common frame of reference, the thickness of fat was calculated across the surface of the heart. The sampling strategy for the locations of fat thickness was based on a spherical parameterization (θ, φ) where θ represents the azimuthal angle (angle from positive x-axis) and φ represents the elevation angle (angle from the x-y plane). The points on the fat model were translated so that the origin of the 3D coordinate system was at the centroid of the model points. Then, for each pair of angles for θ from 90° to −90° and for φ from 0° to 360°, a ray was cast from the origin in the direction indicated by the pair of angles. To compute the fat thickness map for the (θ, φ) parameterization, intersections of the ray with the fat model were calculated. The models were represented as a set of vertices and triangular faces and the required intersection points were determined using a ray/triangle intersection algorithm. The ray can be represented as follows:

$$R(t)=O+tD \quad (2)$$

where R is the set of (x,y,z) coordinates of the ray vector, O is the origin, D is the set of (x,y,z) coordinates of the ray direction, and t is the distance along the ray. In the formulation used here, the directions, D, of each ray to use for the parameterization map were determined by converting from spherical to Cartesian coordinates using the following equations:

$$x=r\cos(\varphi)\cos(\theta) \quad (3)$$

$$y=r\cos(\varphi)\sin(\theta) \quad (4)$$

$$z=r\sin(\varphi) \quad (5)$$

where r is chosen to ensure that the Cartesian point is sufficiently distant from the origin to be outside potential model surface intersections. Locations across the planar surface of each individual triangle are given by the following equation:

$$T(u,v)=(1-u-v)V_1+uV_2+vV_3 \quad (6)$$

where u and v are the barycentric coordinates and $V_1$, $V_2$, and $V_3$ are the three vertex locations of the triangle. The intersection between the ray and any given triangle, therefore, can be determined by setting Equations (2) and (6) equal to each other, rearranging the terms, and then solving the system of linear equations.

The fat deposits near the base of the heart and the ostia of the right coronary artery (RCA) and the left main coronary artery create non-trivial surface topologies in the fat models. They are not "connected" surfaces, meaning that there can be some points on the surface model that are not connected by a path along the surface to other points on the model. In other words, there can be multiple "objects" associated with the model surface. The fat thickness at any given (θ, φ) location was calculated as the total, accumulated thickness of adipose tissue that the ray traveled through as it passed through the model. Ray/triangle intersections, in Cartesian coordinates, were taken in pairs to calculate the adipose tissue thickness along that particular angle defined by the (θ, φ) location. The Cartesian coordinates of each point were used to compute adipose tissue thickness for each pair of intersections, as in the following equation:

$$R_{fat}=\sqrt{x_2^2+y_2^2+z_2^2}-\sqrt{x_1^2+y_1^2+z_1^2} \quad (7)$$

Where the adipose tissue thickness $R_{fat}$, in mm, was recorded for the fat map based on the (θ, φ) spherical parameterization.

This process was repeated for all 10 models, and the resulting maps were used to compute an average fat thickness. The last step involved applying the average fat thickness values to appropriate locations on the average heart model. The mapping of locations of the average fat thickness to the average heart surface model was performed using the (θ, φ) spherical parameterization. For each vertex on the model, the x, y, and z Cartesian coordinates were converted to spherical coordinates using the following equations:

$$\theta = \arctan\left(\frac{y}{x}\right) \quad (8)$$

$$\varphi = \arctan\left(\frac{z}{\sqrt{(x^2+y^2)}}\right) \quad (9)$$

Where the (θ, φ) coordinate pair was used as in index into the average fat map and the closest value was used as the fat thickness for that location on the heart surface. Bilinear interpolation was used to determine fat thickness values for shading of the model between vertices.

Example 4. Classification of Cardiac Fat Using Spectral Analysis of Ultrasound Radiofrequency Backscatter For the fourth example, the echocardiography images and their corresponding raw radiofrequency (RF) signals data can be obtained using a portable ultrasound machine such as the Mindray Zonare ZS3 machine with a P4-1c phased array transducer. The heart images are imaged via the ultrasound machine using six different views of the heart: parasternal long-axis view, parasternal short-axis views of the mitral valve, papillary muscles, and apex, subcoastal view, and apical view. Each view of the heart was imaged twice resulting in twelve B-mode image loops and corresponding RF data files for each participant. The RF data was obtained simultaneously from the Zonare machine during echocardiography for all the six views in harmonic imaging mode with a center frequency of 3.5 MHz. The data was stored and retrieved from the machine using a Linux terminal. As an example, eighty frames of RF data were collected to correspond to the B-mode image loops.

From the RF data obtained during echocardiography, gray-scale images are reconstructed using the raw data acquired for each view for each subject as described further with respect to Example 5 below. These images are used to manually identify specific ROIs that correspond to the three target tissues, i.e., CAT, myocardium, and blood. Automatic identification of ROIs can be conducted via the process above described with respect to FIG. 6 or via the spline-based modeling approach described by examples 7, 8, and 9 below. The reconstructed image is inverted along the longitudinal axis. In this embodiment, each of these images contain 201 RF scan lines. As an example, eighty frames of RF data were collected for each B-mode image loop, one frame was selected that best represented the target tissue types for the ROI selection. In example, a total of 175 ROIs were selected that included CAT, myocardium, and blood regions. The size of each ROI was based on the thickness of the tissue; therefore, the number of samples in each ROI is different. The portions of the RF signals passing through each of these ROIs were extracted from the RF data for spectral analysis.

Next, the RF data lines extracted from the ROIs were used for the calculation of spectral parameters. An autoregressive (AR) model is used for PSD estimation and spectral analysis. More specifically, Yule-Walker equations were used to compute the PSD estimates of the RF lines. The ROIs are small and the RF signals for the ROIs do not have very many samples. In ultrasound, depth corresponds to the timing of the signal and are therefore the RF signals analyzed are short in time. The AR model order was set to be the same as the number of RF samples in each specific ROI that's being used to determine the region of RF signals that are process. The PSD estimates of each RF line in an ROI were averaged to obtain one PSD estimate per ROI. In this example, from these estimates, thirteen spectral parameters were calculated for three different bandwidth ranges of 3 dB, 6 dB, and 20 dB. The thirteen parameters calculated in this example are as follows: (1) maximum power (dB), (2) frequency of maximum power (MHz), (3) mean power (dB), (4) negative slope in dB/MHz (least squares regression of PSD), (5) y-intercept on the negative slope (dB), (6) positive slope in dB/MHz (regression of PSD), (7) y-intercept on the positive slope (dB), (8) mid-band power (dB), (9) mid-band frequency (MHz), (10) the depth of the ROI (cm), (11) power at 0 MHz (dB), (12) integrated backscatter of the entire power spectrum (dB), and (13) integrated backscatter of the power spectrum present in a bandwidth (dB). Each of these parameters were used to generate random forest classifier for classification. Other parameters can be considered as well.

Random forests are machine learning techniques that repeatedly partition the data until a sample is identified as belonging to a class. Each tree in a random forest starts branching out with a subset of features and samples. As there are thirteen spectral parameters used as predictors, the trees are generated with a random subset of three features. The data is evaluated for possible partitions at each node based on the split resulting in the largest decrease of Gini impurity. The branch nodes are repeatedly split into left and right children nodes using the chosen split criterion until no further splits are possible. The last node is known as the leaf node and indicates the class. An unknown sample is evaluated for each split criterion and navigated through the branch nodes until it reached a leaf node that indicated the class of the sample. The final prediction of a random forest is the majority vote of all the trees in the forest. The spectral parameters calculated from the average PSD estimates were used to generate random forest classifiers to identify the target tissue types.

In this example, the parameters calculated from the 175 ROIs were used to generate three random forests for the three bandwidth ranges. Seventy percent of the data was used to train the classification trees and the remaining thirty percent data was used as test data. Out-of-bag (OOB) error was computed each time a forest was created. OOB error gives the measure of the prediction error for each sample used in the generation of the trees. Using this measure helps optimize the performance of the classifier. The classification trees are generated from a subset of the samples which enables calculating the prediction error of the trees on the samples that were not included in the generation of the trees. Based on this approach, the number of classification trees was selected to be fifty. Predictor Importance is another measure that gives the relative importance of each predictor or spectral parameter in generating a forest. From the samples that were not used in the generation of a tree, the prediction accuracy of the predictors is calculated. Then, these values are shuffled randomly for a specific predictor keeping all the other values constant. The decrease in the prediction accuracy is computed from the shuffled data and the average decrement of prediction accuracy across all the trees is shown as the importance of that predictor. This measure was also calculated for each random forest generated.

Example 5. Spectral Analysis of Ultrasound Backscatter for the Identification of Cardiac Fat The fifth example is identical to the fourth example except that in-phase and quadrature components (IQ data) was obtained by demodulating the RF data. This has the effect of shifting the frequency spectrum, centered at 3.5 MHz as RF data, down to a center of 0 MHz as IQ data. Using IQ data for processing in the system has the advantage of requiring lower sample rates and less memory than RF data. The IQ demodulation does not affect the shape of the frequency spectrum, only its center frequency. The raw data for this study, post-beam-formation and post IQ demodulation, was stored onto a separate acquisition system during the imaging sessions. The acquisition system operated a Linux terminal that issues the acquisition commands to the Zonare ultrasound system and the data was later retrieved for processing.

Figure 10A:
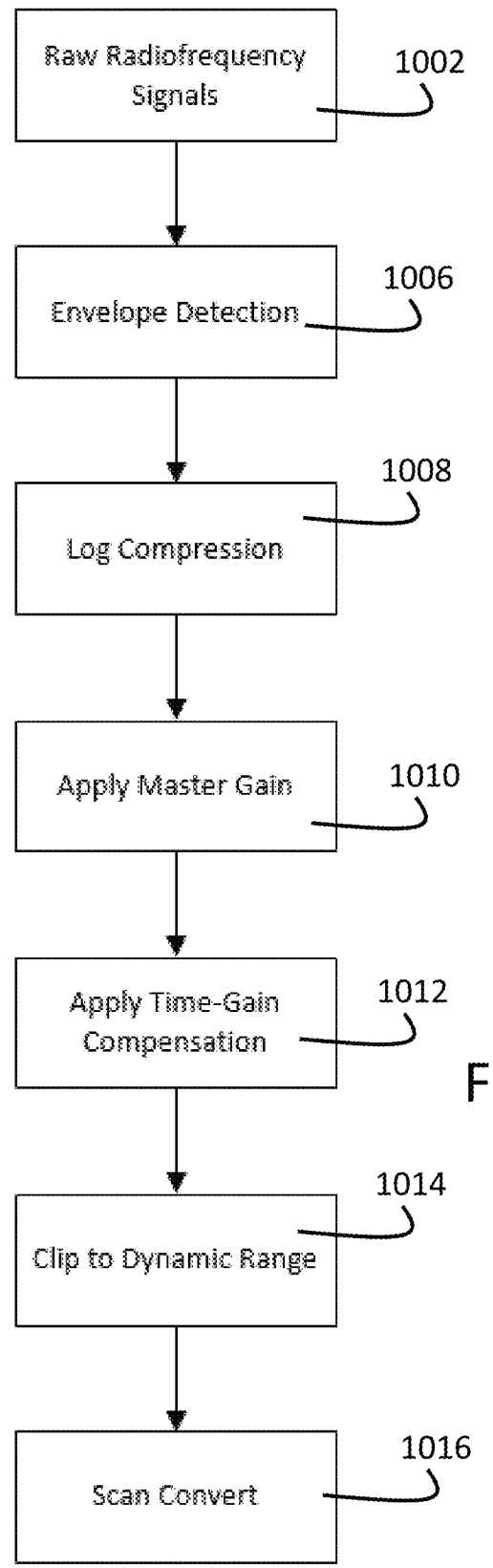
FIG. 10A shows a flowchart depicting the operation of software implementing a preferred method of the invention to reconstruct the gray-scale B-mode images from the raw data acquired for each view for each subject.
Figure 10B:
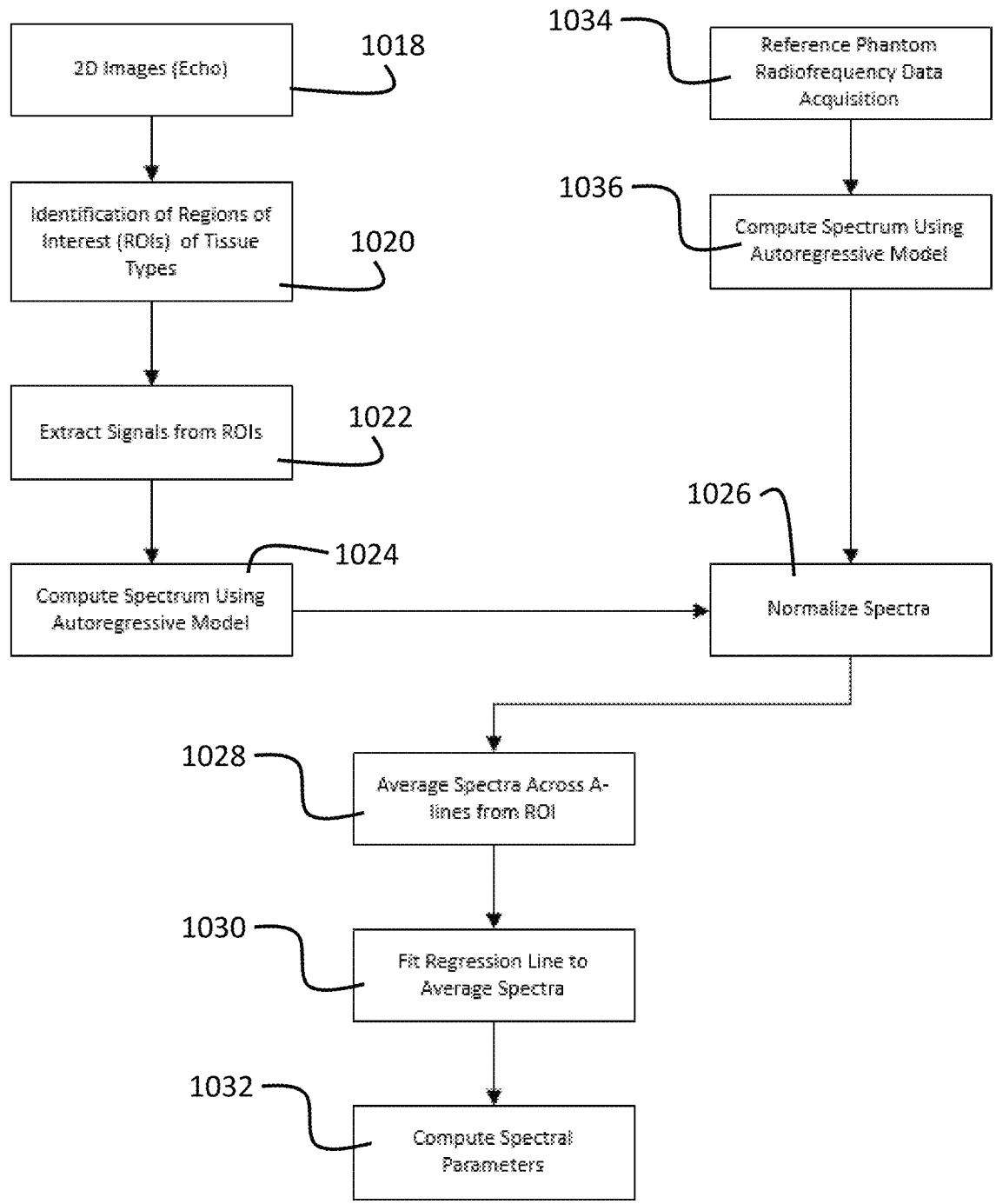
FIG. 10B shows a flowchart depicting the operation of the software implementing a preferred method of the invention to compute spectral parameters during exam imaging and/or during training of machine learning.

Software was written to reconstruct the gray-scale B-mode images from the raw data acquired for each view for each subject. FIGS. 10A and 10B show a flowchart depicting the operation of the software. The raw gray-scale images in step 1002 contained 201 raw A-lines whereas the number of samples depended on the depth of each image. The raw signals were processed on a line-by-line basis, including envelope detection 1006, log compression 1008, master gain 1010 and time-gain-compensation 1012, and dynamic range clipping 1014 to extract signals. The image frames in the recorded loop were presented in both native rectangular format and in their traditional B-mode scan converted format from a conversion in step 1016.

Figure 11:
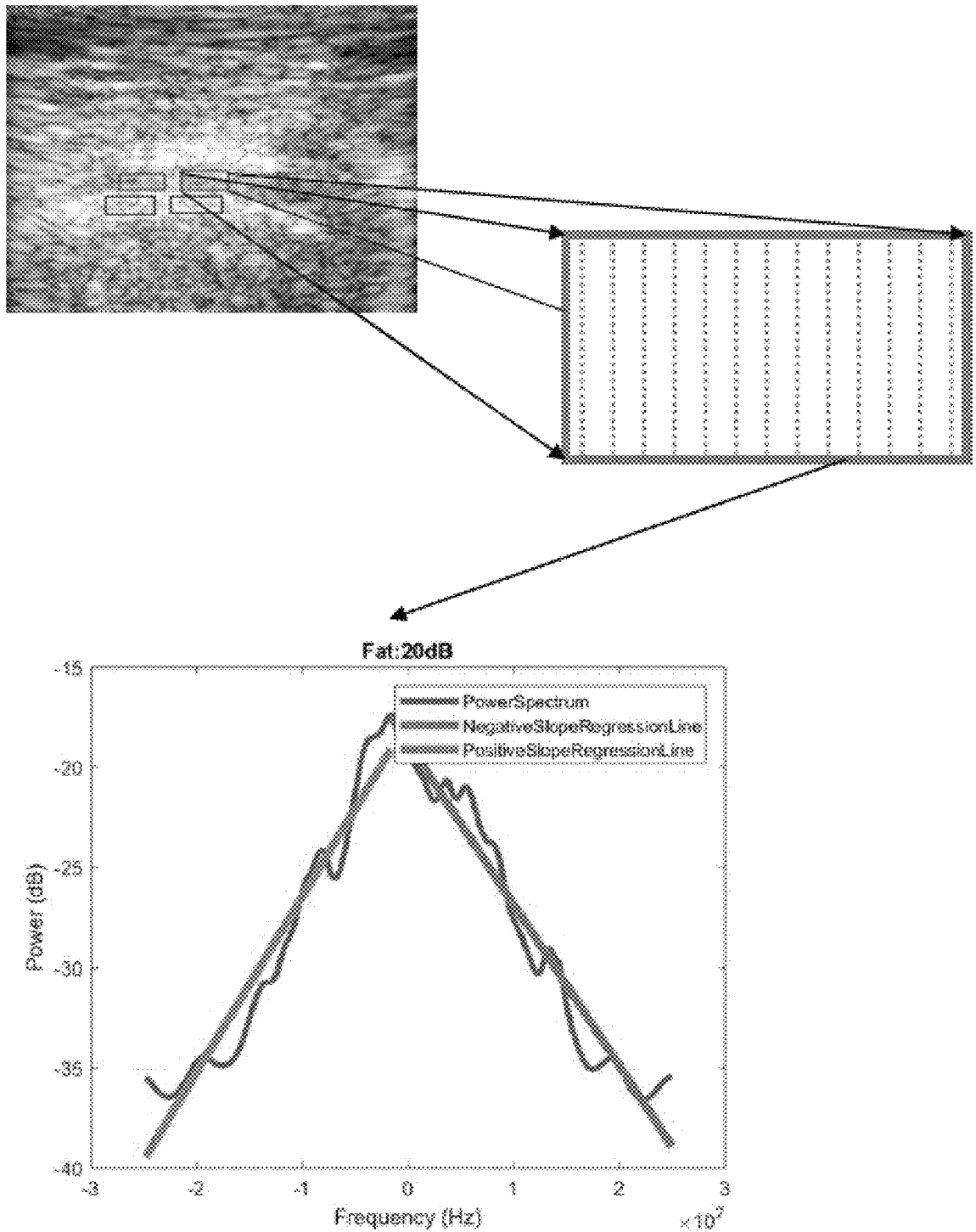
FIG. 11 shows an example operation indicating the raw signal A-lines that pass through a small Region of Interest (ROI) and the resulting average frequency spectrum for that ROI.
Figure 12A:
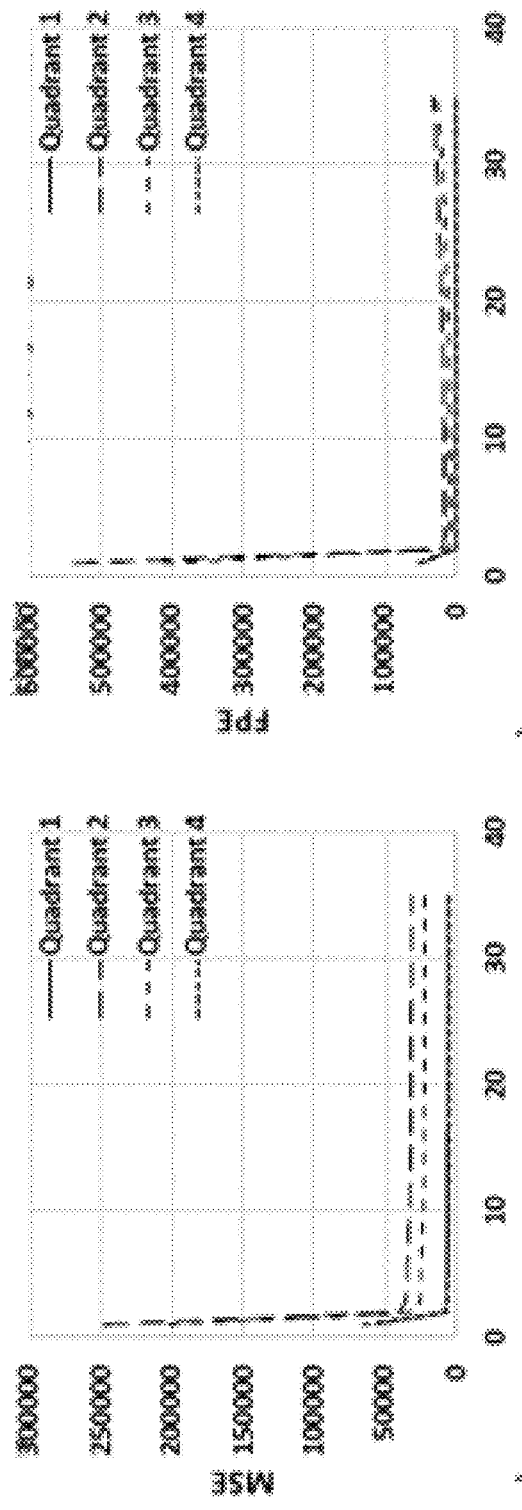
FIGS. 12A-12D show the mean of the cost functions across each set of ROIs versus AR order.
Figure 12B:
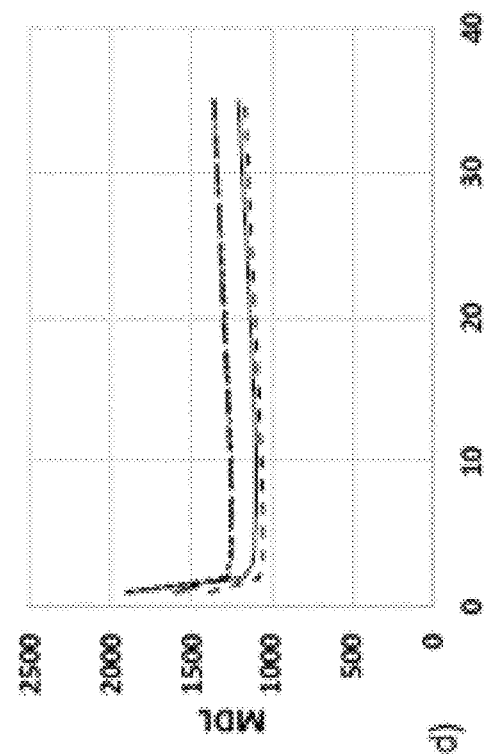
Figure 12C:
Figure 12D:
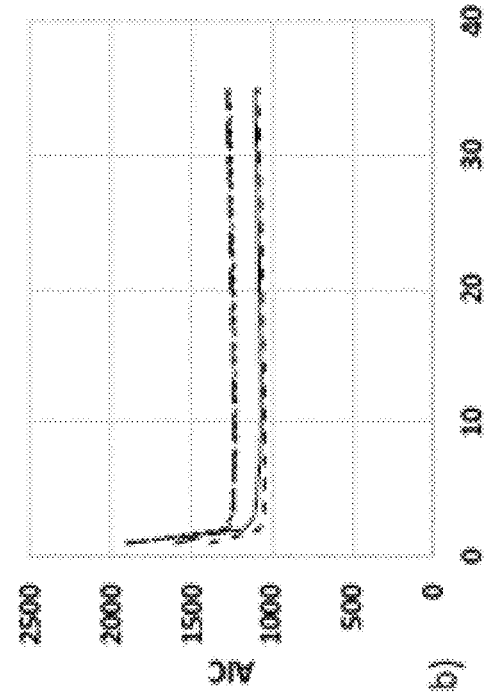

From the reconstructed images, regions-of-interest (ROIs) that target fat, muscle, and blood were manually selected. As mentioned above, automatic identification of ROIs can be conducted via the process above described with respect to FIG. 6 or via the spline-based modeling approach described by examples 7, 8, and 9 below. While also using the recorded video-loop on the Zonare system as a reference, a user reviewed the reconstructed images in the user interface. Each image loop contained 80 reconstructed images in step 1018. The user identified image frames from the loop where small homogeneous regions can be located with high confidence. The specific ROIs for fat, muscle, or blood where then selected 1020 from display by clicking the top-left and bottom-right corners of an ROI in the rectangular, non-scan-converted image. A total of 805 ROIs were identified, including 271 ROIs for fat, 332 ROIs for muscle, and 202 ROIs for blood. The ROIs were selected only in areas on the images with a known tissue type and therefore the sizes depended on the thickness of that tissue type. The segments of the raw signal lines corresponding to the ROIs were extracted 1022 from the raw data for further processing, as shown in FIG. 11. In each of the rectangular ROIs, the column-wise or the vertical data represents the scan lines of the transducer whereas the row-wise or the horizontal data represents the raw A-line signals in the ROI. In the raw data, the ROIs are therefore rectangular, but in the correct geometry of the scan-converted B mode images, the ROIs have a sector shape dependent on the size of the ROI selected. Indicated ROIs can be illustrated by rectangles in a displayed image.

The scan lines extracted from the ROIs were analyzed using software. An example A-line traverses through three identified ROIs, one of each tissue type, is considered. The first step in the signal processing was to convert the IQ data back to its original RF format. The process of modulating complex IQ data back to its original RF representation involves upsampling the data, by a factor of nine in the case of the Zonare system, and then modulating the baseband IQ signal back to an RF bandpass signal using Equation (10) shown:

$$x[n] = \text{Real}\{(x_{IQ}[n])e^{j2\pi f_{demod}t[n]}\} \quad (10)$$

where x[n] is the sampled RF signal, $x_{IQ[n]}$ is the sampled complex IQ signal, $f_{demod}$ is the modulation frequency (3.5 MHz in this case), and t[n] is the sampled time vector derived from the original sample frequency (50 MHz in this case). The spectral features were computed 1024 from the frequency spectrum of the short signal-segments extracted from the ROIs. An AR model of a random process is shown in Equation (11):

$$x[n] = -\sum_{k=1}^{p} a[k]x[n-k] + e[n] \quad (11)$$

where p is the AR order, a[k] are the AR coefficients, and e[n] is a white noise random process. The present value x[n] is represented as a weighted sum of past values, where the weights are the AR coefficients. The input is modeled as white noise (e[n]) that has variance $\sigma^2$. The power spectral density (PSD) of the all-pole AR model can be estimated as shown in Equation (12):

$$PSD_{AR}(f) = \frac{\sigma^2}{\left|1 + \sum_{k=1}^{p} a[k]\exp(-j2\pi fk)\right|^2} \quad (12)$$

where PSD is the power spectral density as a function of frequency (f), $\sigma^2$ is the variance of the white noise, and a[k] are AR coefficients, and p is the AR order of the model. The AR-based PSD in this application was calculated using an alternative relationship between the AR coefficients and the autocorrelation function that leads to the Yule-Walker system of equations shown in their augmented form in Equation (13):

$$\begin{bmatrix} R_{XX}(0) & R_{XX}(-1) & \ldots & R_{XX}(-p) \\ R_{XX}(1) & R_{XX}(0) & \ldots & R_{XX}(-p+1) \\ \vdots & \vdots & \vdots & \vdots \\ R_{XX}(p) & R_{XX}(p-1) & \ldots & R_{XX}(0) \end{bmatrix} \begin{bmatrix} 1 \\ a_1 \\ \vdots \\ a_p \end{bmatrix} = \begin{bmatrix} \sigma^2 \\ 0 \\ 0 \\ 0 \end{bmatrix} \quad (13)$$

where $\sigma^2$ is the variance of the white noise, and RXX is the autocorrelation calculated from the signal. These equations can be solved recursively using the Levinson-Durbin algorithm, incrementally computing the AR parameters $\{a_{p1}, a_{p1}, \ldots, a_{p1}, \sigma^2\}$. In this framework, the variance of the noise $\sigma^2$ is equal to the modeling error in the spectral estimate, given by Equation (14):

$$\sigma(p)^2 = \frac{1}{N-p}\sum_{k=p+1}^{N}(x_p[k] - x_d[k])^2 \quad (14)$$

where p is the AR order, $\sigma(p)^2$ is the MSE as a function of order, and N is the number of samples used for analysis.

Several methods exist to estimate optimal order, including Akaike's Information Criterion (AIC), Final Prediction Error (FPE), and the Minimum Description Length (MDL). Each is a function of the MSE, but includes a mechanism for penalizing for increasing order. They are shown in Equations (15-17) below:

$$FPE = \frac{N+p+1}{N-p-1}\sigma(p)^2 \quad (15)$$

$$AIC = N\ln[\sigma(p)^2] + 2p \quad (16)$$

$$MDL = N\ln[\sigma(p)^2] + p\ln N \quad (17)$$

where p is the AR order, $\sigma(p)^2$ is the error as a function of order, and N is the number of samples used for analysis. This approach was used to determine a range of AR orders to evaluate.

To understand whether the range of orders to assess was related to the size of the ROI, the ROIs were split up into four quadrants. The median number of samples (99) and median number of A-lines were used to delineate the four quadrants. The number of ROIs in each quadrant were 315, 145, 246, and 99, respectively, in quadrants one through four. The mean of the cost functions across each set of ROIs versus AR order is shown in FIGS. 12A-12D. The smallest ROI had 36 samples, and since the order cannot be larger than the number of samples, the maximum order investigated was chosen to be 35. The order penalty appeared to have minimal impact after the initial drop in MSE. Based on these findings, a range of orders from 5 to 35 (in increments of 5) were investigated.

Figure 13:
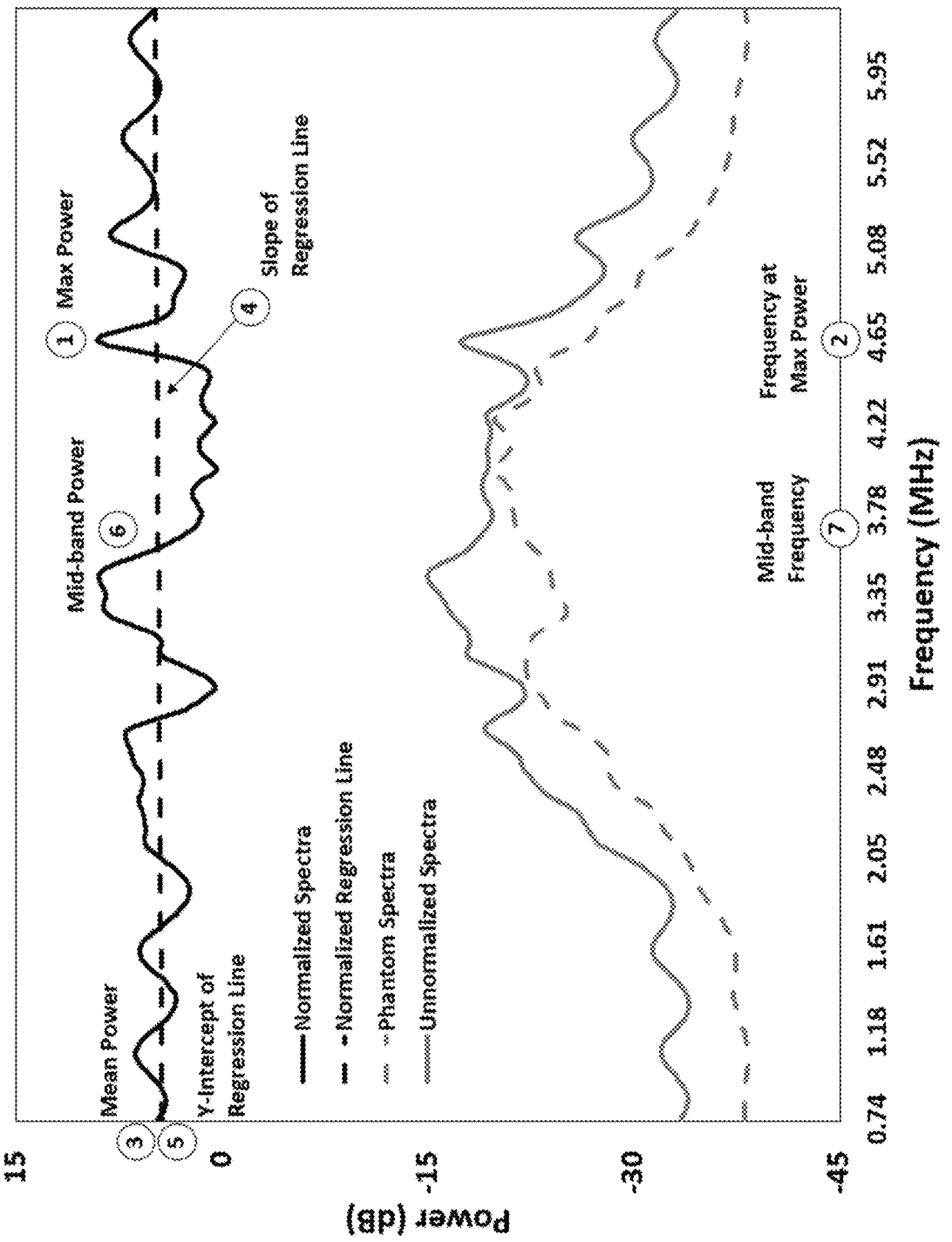
FIG. 13 shows an example power spectral density (PSD) analysis with the corresponding regression lines.

Features derived from the unnormalized power spectrum and can be used to classify three cardiac tissue types—fat, muscle, and blood. Optimal AR order can be determined, and is facilitated by incorporating the conversion of the IQ data back to RF because it increases the sample rate of the signals. Experiments included collection of reference data from a tissue-mimicking phantom (Model 040GSE, CIRS, Inc., Norfolk, VA, 0.5 d 1 B/cm-MHz side), which was used to compensate for attenuation, diffraction, and the transmit and receive characteristics of the system. The depth and size of each ROI was used to obtain an ROI of the same depth and size from the data collected using the calibrated phantom. The normalized PSD for each A-line signal was calculated 1026 (FIG. 10B) by subtracting the reference phantom PSD of the same depth and size from the unnormalized PSD also shown in FIG. 13. The normalized spectra are averaged for the ROI 1028 (FIG. 10B). A regression line is fit to the average normalized spectrum 1030 and the spectral parameters are computed 1032 (FIG. 10B). The spectral parameters are illustrated in FIG. 13.

Spectral analysis was performed for both the normalized and unnormalized PSDs. For the unnormalized PSDs, thirteen parameters were calculated as follows: (1) maximum power (dB), (2) frequency of maximum power (MHz), (3) mean power (dB), (4) negative slope in dB/MHz (least squares regression of PSD), (5) y-intercept on the negative slope (dB), (6) positive slope in dB/MHz (regression of PSD), (7) y-intercept on the positive slope (dB), (8) mid-band power (dB), (9) mid-band frequency (MHz), (10) the depth of the ROI (cm), (11) power at 0 MHz (dB), (12) integrated backscatter of the entire power spectrum (dB), and (13) integrated backscatter of the power spectrum present in a bandwidth (dB). These unnormalized spectral features can be used to characterize tissue types and were selected here as the primary set of features. The same basic set of features was used for the normalized PSDs, but with only one slope and one y-intercept because only one regression line was fit to each normalized PSD. Experiments indicate that the 20-dB bandwidth has the most promise. Therefore the 20-dB bandwidth was used for computation of the spectral features in the experiments. An example PSD with the corresponding regression lines is shown in FIG. 13.

Random forests facilitate insights into the predictive power of individual features. The forests are built using classification trees, a machine learning algorithm where data is partitioned repeatedly until a sample is identified as belonging to a particular class. Each tree starts with a subset of the features, typically the square root of the number of total features. As an example, 11 features were used for the normalized data and 13 were used for the unnormalized data. Therefore, 3 randomly selected features were used at each node. The data is evaluated for possible partitions at each node based on the split resulting in the largest decrease of Gini impurity. The branch nodes are repeatedly split into left and right children nodes using the chosen split criterion until no further splits are possible. The last node is known as the leaf node and indicates the class. An unknown sample is evaluated for each split criterion and navigated through the branch nodes until it reached a leaf node that indicated the class of the sample. The final prediction of a random forest is the majority vote of all the trees in the forest.

Each time the training data are sampled to create one of the classification trees, there is a set of samples not used—these are called the "out-of-bag" (OOB) samples. The error in prediction for these OOB samples is called the OOB error and can be used to optimize parameters to be used for the classification. In the current study, the OOB error was computed for an increasing number of trees used in the random forest. More trees can begin to minimize error, but a plateau can be reached. Beyond the plateau, additional trees included in the random forest only increase computational cost and do not decrease error. With this in mind, after testing, 30 classification trees was chosen as the nominal value for each random forest built after an evolution from 50 to 30 trees by looking at OOB error. The OOB error was also used to compare the predictive importance of the spectral parameters. In a classification tree, if a feature is not important, permuting the values of that feature within the data will not impact the prediction accuracy. The OOB error is calculated before and after permuting the data for each feature and the difference between OOB errors is averaged across all trees in the forest. This results in a relative predictive importance for each feature.

Assessment of classification techniques or machine learning algorithms typically involves the random separation of the data into training and test sets. However, rather than using a single randomized split into training and test data, a more robust validation approach called Monte Carlo cross-validation (MCCV) strategy was adopted. It involves repeated randomizations into training and test sets containing 75% and 25% of the data, respectively. A new random forest is built using each set of training data and tested with the corresponding test data for that randomization. The accuracy (A), sensitivity (Se), and specificity (Sp) values were calculated for each of the random forests based on the derived spectral parameters in the Monte Carlo process. Youden's Index (YI=Se+Sp−1), a metric that takes both sensitivity and specificity into account, was also calculated for each MCCV sample. The difference between means for both accuracy and YI were also computed, including the 95% confidence intervals and p values for level of significance.

An additional question associated with this study was whether the ability to differentiate tissue types would be robust to the size of the ROIs available. To understand this factor directly, an additional "leave-one-out" cross validation was performed on the random forest classification. Each ROI in the database was iteratively set aside as the test ROI and the remaining ROIs were used to create a random forest. The test ROI was used as input to the random forest and the output classification was compared to the known tissue type, noting the number of A-lines and number of samples available for that ROI. This process was repeated for the entire database and the number of correct and incorrect classifications were recorded versus the number of samples in the ROI and versus the number of A-lines in the ROI.

Example 6. Use of Two-Dimensional and Three-Dimensional Deep Learning Architecture for Segmentation of Adipose Tissue (Cardiac Fat) in Cardiac Magnetic Resonance Images A sixth example involves the use of 3-dimensional (3D) convolutional neural network (CNN) and 2-dimensional (2D) CNN for the purpose of classifying cardiac adipose tissue (CAT). Both models use a U-Net architecture to simultaneously classify CAT, left myocardium, left ventricle, and right myocardium. In this example, cardiac MRI data was collected using a 3.0 T MRI system (Vida, Siemens Medical Systems). This system implements a 3D black blood turbo spin echo (TSE) sampling perfection with application-optimized contrast using different flip angle evolution (SPACE) sequence. The MRI scans were ECG and respiratory-navigator-gated across the entire heart in 1-cm increments along the cardiac short axis. The planar resolution of this system was approximately 1.47×1.47 mm. The scans obtained with the MRI system were acquired in cine loops that captured the entire cardiac cycle from one slice location in a sequence of images. Image frames from each of these cine loops were extracted from two key phases in the cardiac cycle—end-diastole, when the heart is fully expanded, and end-systole, when the heart is fully contracted. The image frames from those times in the cardiac cycle were concatenated into end-systolic and end-diastolic volumes for each scan.

The volumes obtained from extracting still-frame data from the cine loops were loaded into the open-source medical imaging software 3DSlicer where the CAT, left myocardium, left ventricle, and right myocardium were manually segmented by three separate observers to provide labelled data to train the deep learning networks. In this example, a total of 350 slices from 35 volumes from each cardiac phase were segmented by each observer. Several models were trained in this study using various combinations of these segmentations. Separate models for each cardiac phase were trained first using the segmentations of a single observer. New models for each cardiac phase were then trained using randomly chosen segmentations from one of three observers for each volume to understand the effects of bias within a model. Lastly, a single model was trained using randomized segmentations from both cardiac phases to determine if a single, multi-phase model trained using all data is more accurate and robust than separate models for each phase trained with less, but more specific, data.

The individual slices in each original scan volume were used as individual inputs to train the 2D models in this study, while each volume acted as an individual input to train the 3D model. Both the slices and volumes underwent Z-score intensity normalization. The equation for Z-Score intensity normalization is shown below in Equation (18), where μ and σ represent the global mean and standard deviation in the given slice or volume respectively, and I and $I_Z$ represent the original and Z-score normalized intensity for the given pixel or voxel respectively.

$$I_Z = \frac{I - \mu}{\sigma} \tag{18}$$

Figure 14:
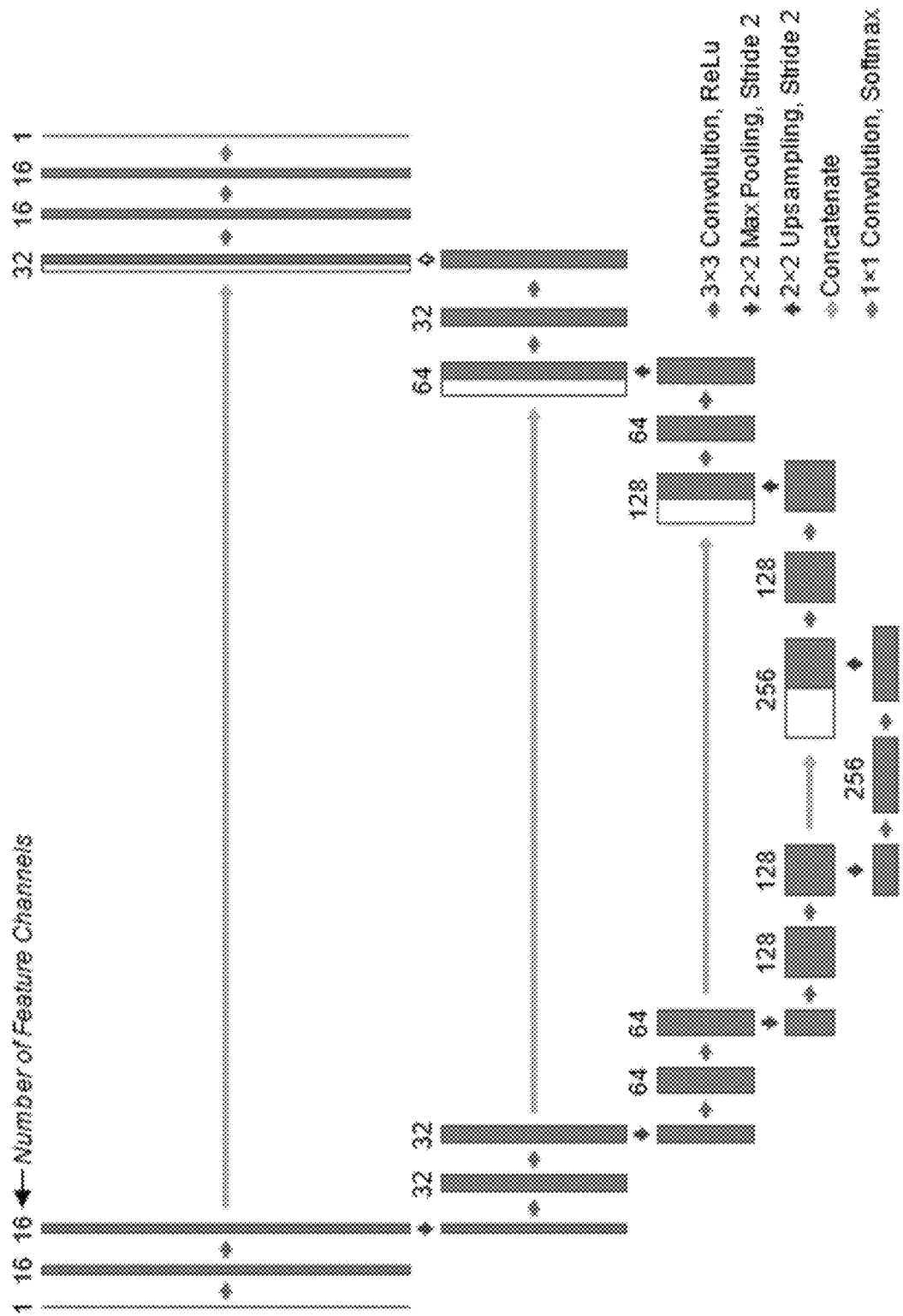
FIG. 14 shows an example 2D U-net architecture trained in experiments for automatic segmenting of patient heart image data.

The 2D U-net architecture used in this study is comprised of an analysis and synthesis path with a depth level of 5 as shown in FIG. 14. The slices from the scan volumes were resampled to a resolution of 64×64 and used as the input data to train the neural networks. Resampling to a square shape allows the networks to more easily perform convolutions, which are typically defined by square kernels, on the input data. Of the 350 image slices per cardiac phase, 85 percent were randomly selected and used for training the models. The remaining slices were saved for testing model performance after training was complete. Of the given model's training set, a randomly selected 10% of these scans were held out at each training iteration (epoch). This partition, known as the validation set, was used to evaluate the model's performance at each epoch. This is done to avoid bias in the model. The input data is transformed into a feature map which undergoes two 3×3 convolutional layers, a rectified linear unit (ReLu) activation function, and a 2×2 max pooling layer at each step of depth in the analysis path. The first step uses 16 feature channels. These models use a stride of 2, which doubles the number of feature channels at each analysis step. After 5 steps, the feature map enters the synthesis path. At each synthesis step, the feature map is upsampled by a factor of 2 in each dimension using nearest neighbor interpolation. The number of feature channels are halved before undergoing two more 3×3 convolutional layers and a ReLu. After 5 synthesis steps are completed, the final feature map undergoes a 1×1 convolution with a softmax activation that reduces the number of feature channels to the number of labels to be predicted. The final shape of the output data is 64×64×5. Each 64×64 layer corresponds to a probability map for a given label. The models were trained on two NVIDIA RTX 2070 Super graphics processing units (GPUs) linked together using an NVLink bridge to combine their processing power without the need for additional code. This GPU system was set up to leverage cuDNN, a dedicated library of deep-learning specific functions that greatly accelerate the training and performance of deep learning network. The 2D models' architecture and training specifications are listed in Table 2.

TABLE 2

2D and 3D model specifications and hyperparameters

| Parameter | 2D Model Architecture | | 3D Model Architecture | |
|---|---|---|---|---|
| | End Diastole | End Systole | End Diastole | End Systole |
| Training/Testing Split (%) | 80/20 | 80/20 | 80/20 | 80/20 |
| Training/Validation Split (%) | 80/20 | 80/20 | 80/20 | 80/20 |
| Training Batch Size | 5 | 5 | 1 | 1 |
| Validation Batch Size | 5 | 5 | 2 | 2 |
| Initial Learning Rate | 0.001 | 0.001 | $5 \times 10^{-4}$ | $5 \times 10^{-4}$ |
| Patience (Epochs) | 10 | 10 | 10 | 10 |
| Learning Rate Drop Factor | 0.5 | 0.5 | 0.5 | 0.5 |
| Early Stop (Epochs) | 10 | 10 | 50 | 50 |

Figure 15:
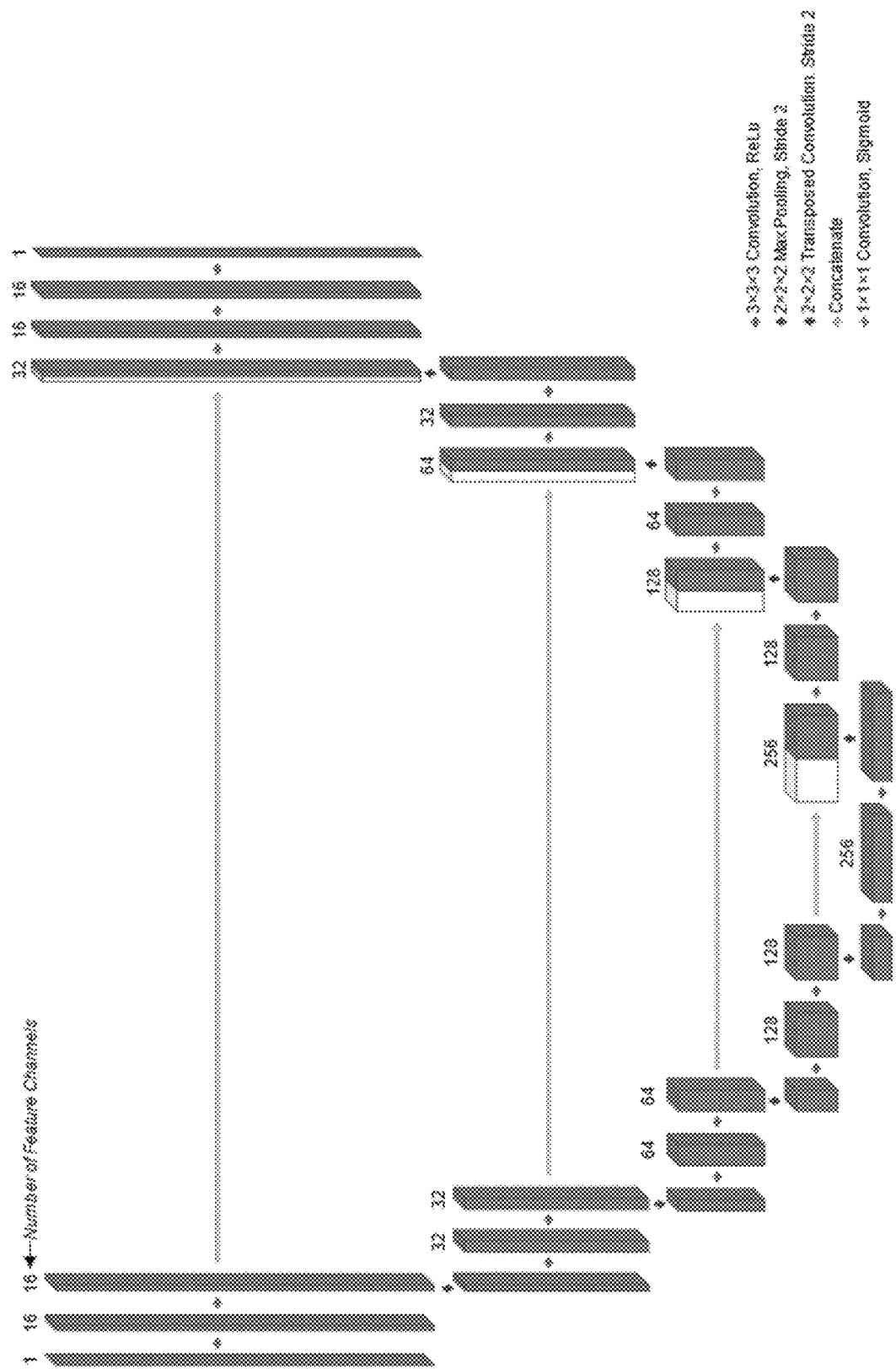
FIG. 15 shows an example 3D U-net architecture trained in experiments for automatic segmenting of patient heart image data.

The specific 3D U-Net architecture used in this example has an analysis and synthesis path with a depth level of 5 resolution steps as shown in FIG. 15. The scans used as the input data to train the networks were resampled to a resolution 64×64×64 voxels using nearest neighbor interpolation. Resampling to a cubic shape allows for easier volumetric processing as the convolutions in these neural networks are all set to be cubic filter sizes. The training split was 80 percent; the remaining 20 percent was used to test the synthesized models' performance. The validation sets used to evaluate the models' performance at each epoch was a random 20 percent of the training data. The input data at each step in the analysis path is passed as a feature map through two 3×3×3 convolutional layers and a ReLu activation function followed by a 2×2×2 max pooling layer. The first step in the analysis path uses 16 feature channels; this number is doubled at each consecutive analysis step. After the 5 analysis steps, the data then enters the synthesis path. At each step in this path, the feature map undergoes a 2×2×2 transposed convolution and reduces the number of feature channels by a factor of 2. This data is then concatenated with the feature map from the analysis step of the same depth as the current synthesis step. After concatenation, the data undergoes two more 3×3×3 convolutional layers and a ReLu. A 1×1×1 convolution with a sigmoid activation function was used to reduce the final output of the U-net to a feature map with the same number of output channels as labels. The final shape of the output predictions from this U-Net architecture is 64×64×64×5, such that each 64×64×64 layer contains a probability map for each class for every voxel in the input volume. These models were trained with the same GPU-based system used to train the 2D multiclass U-net model. Specifications of the 3D model design and training process are listed in Table 2.

The measure used to calculate the 3D models' loss and tune its weights was the Dice similarity coefficient and Dice loss. The Dice coefficient is defined below in Equation (19):

$$DSC = \frac{2|A \cap B|}{|A| + |B|} \tag{19}$$

Dice loss is calculated below in Equation (20):

$$\text{Dice Loss} = 1 - DSC \tag{20}$$

In the context of medical imaging, the Dice coefficient is a statistical measure of overlap between a manual segmentation (ground truth) and an automated segmentation as predicted by a model. The Dice coefficient is one of the most commonly used statistics used for validation in medical imaging. The 3D models' Dice loss was calculated for each individual predicted class as shown in FIG. 16A and as a weighted total of all predicted classes for both training and validation data at each epoch as shown in FIG. 16B. A single-class Dice coefficient is calculated as shown below in Equation (21).

$$DSC(Class_n) = \frac{2[\text{Truth }(Class_n) \cap \text{Prediction }(Class_n)]}{\text{Truth }(Class_n) + \text{Prediction }(Class_n)} \tag{21}$$

The overall Dice loss is then calculated as shown below in Equation (22). For an unweighted Dice loss calculation, all class weights are equal to 1. This model used a weighted average where the weights were calculated for each class based on relative frequency in a sample. This is a commonly used technique to combat bias in validation metrics due to class imbalance.

$$\mathcal{L}_{Dice} = 1 - \frac{\sum_{i=1}^{n} (DSC_i) * (\text{Class Weight}_i)}{\sum_{i=1}^{n} (\text{Class Weight}_i)} \tag{22}$$

While the Dice coefficient is a good predictor of segmentation accuracy, it cannot fully describe all the spatial detail needed to determine the quality of an automatic segmentation. The Dice coefficient inherently does not highly penalize incorrect labels that are not in the region of overlap between the predicted and manual segmentations. Furthermore, numerical validation statistics do not reflect incorrect or incomplete spatial label placement. A Dice coefficient has no way of showing model predictions that are anatomically impossible, such as CAT that does not touch the heart walls, or myocardium that is not fully connected. For full visual context, all MRI data was passed to the model for segmentation and the resulting predicted segmentations, slice-by-slice for each volume, were plotted next to the corresponding manual segmentations of all three observers with their respective overall and class-wise Dice coefficients when compared to the model's prediction. Most studies that implement the DSC use the traditional, pixel-wise method, where correctly labelling the background contributes to the DSC score. However, since much of the cMRI segmentation data in this study is the background of the image (referred to in this study as "void"), it is relatively easier for the model to find the void space when compared to smaller, more complex-shaped cardiac structures. To remove any potential bias in the validation statistics, the Dice coefficient for only the given cardiac structures was also calculated and shown for every observer's segmentation in comparison to the model's prediction.

To avoid bias from a single observer, this experiment compared the model's segmentations to that of three different observers using the Williams Index. This statistical measurement is used to compare a specific measurement from one "rater" (in this case, the predicted segmentations from the 2D and 3D models) to a set of ground truth measurements collected from other raters (in this case, the manual segmentations from each observer). Furthermore, to measure the impact of using a single observer's segmentation to train models, each model was re-trained using a randomly chosen observer segmentation for each scan's ground truth.

Example 7. Interpolating and Parameterizing the Heart Surface Using the Direct Fit of Tensor-Product B-Spline Surface to Labeled Cardiac MRI Tissue Types The seventh example discusses the methodology for obtaining a two-dimensional (2D) parameterization of the outside surface of the heart after the different tissue types, including left myocardium, left ventricle, right myocardium, and cardiac fat, have been labeled by the segmentation process using the three-dimensional (3D) deep convolutional network discussed in Example 6. The thickness of the fat is measured at each parameterized location, normal to the outside surface of the heart. Previous work used a spherical parameterization, but this approach induced errors in fat thickness measurement because the heart is not perfectly spherical in shape. In addition, the previous approach required the extraction of fat contours from labeled pixels and the import of those contours into Siemens NX for use in 3D model creation. The tedious and manual nature of this process is impractical and not feasible in a manner fast enough for a routine setting. The present parameterization described in this example is that of a 2D spline surface that can be fit to the outside of both the left and right sides of the heart surface as determined by the 3D deep convolutional network labeling. It can be done automatically and allow fat thickness assessment and mapping in a fraction of the time.

Figure 17:
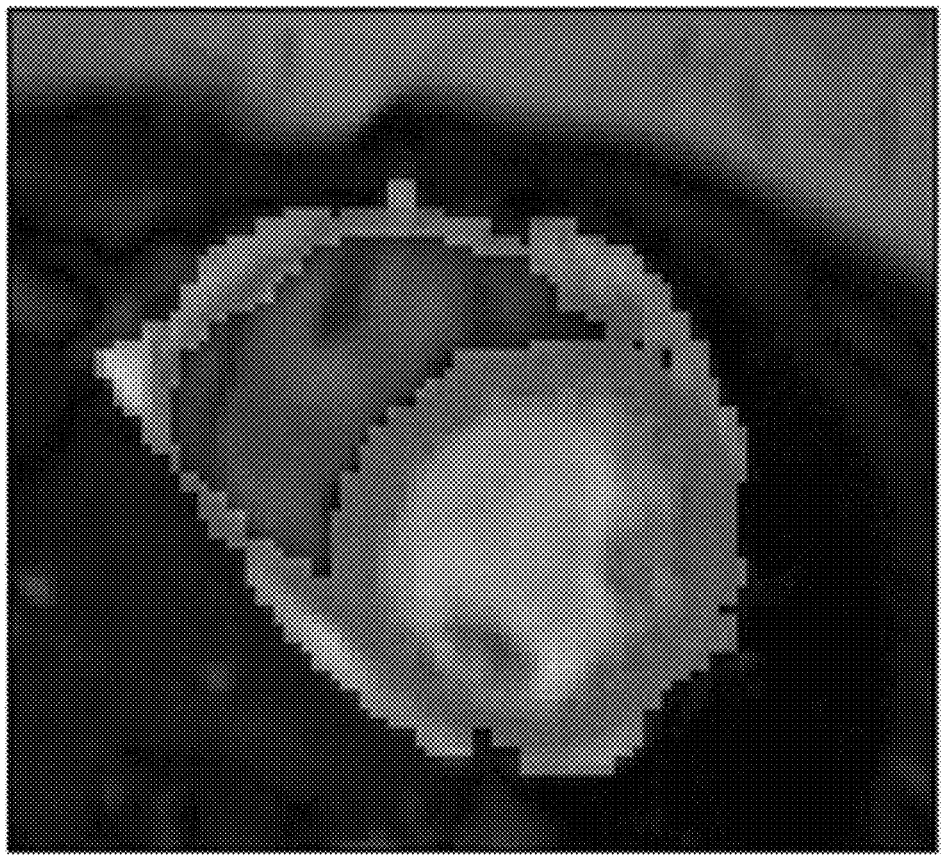
FIG. 17 is an example labeled cardiac MRI resulting from the 3D deep convolutional network.
Figure 18C:
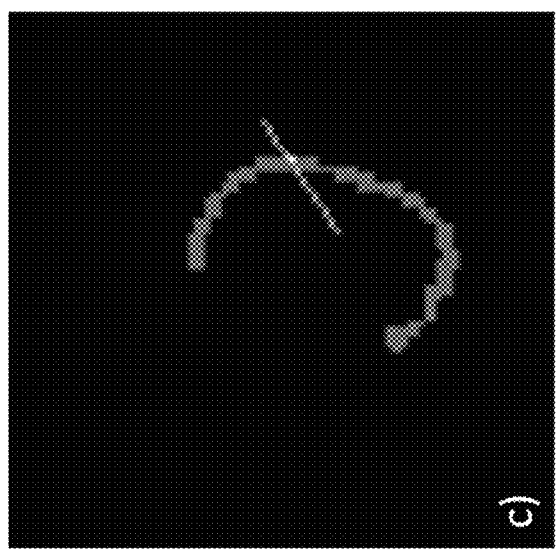
FIGS. 18A-18C show a process to identify "outside points" in heart image data by identifying the centroid of the right myocardium pixels and casing a ray outward at angles from zero to 360°.
Figure 18B:
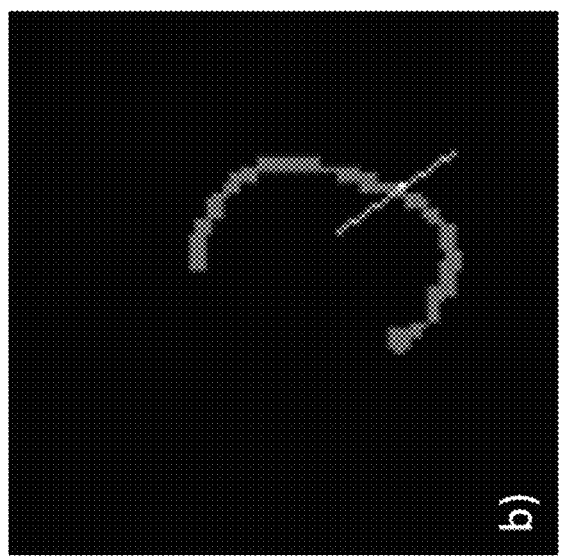
Figure 18A:
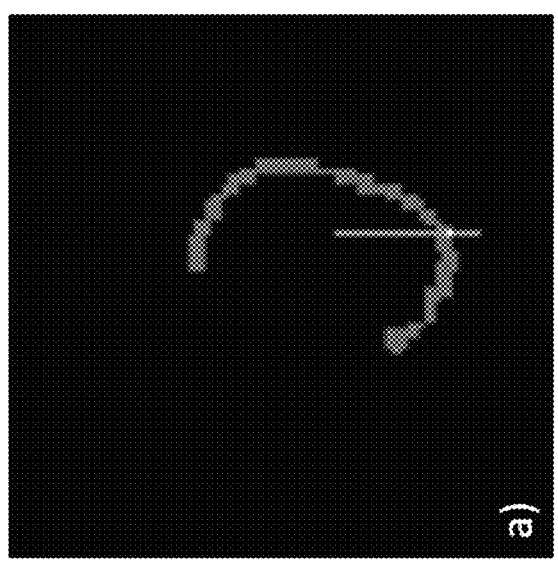
Figure 19A:
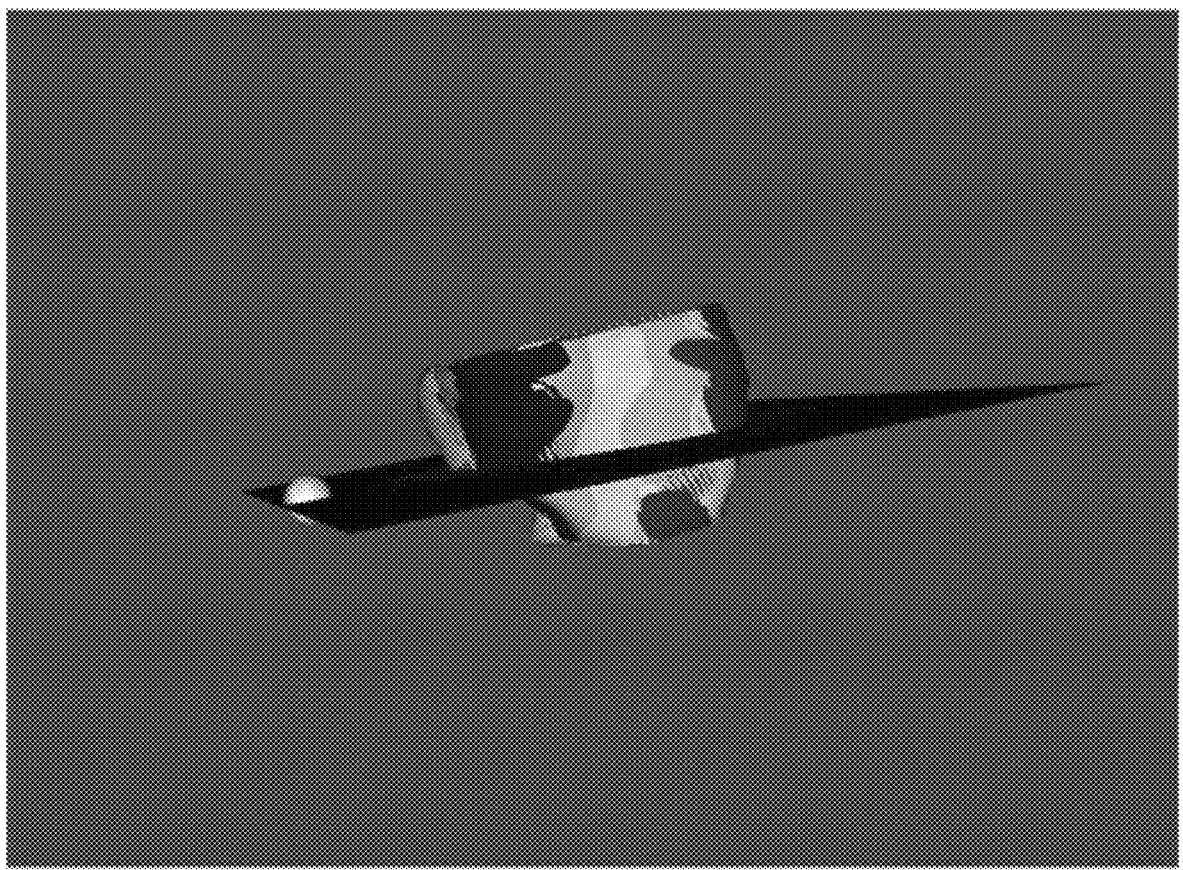
FIGS. 19A-19B show how degree of overlap between the intersection contours and traced contours (from FIGS. 18A-18AC) can be used to locate the correct placement and orientation of the ultrasound image plane with respect to the 3D heart geometry, as represented by the MRI-derived model.
Figure 19B:
Figure 20A:
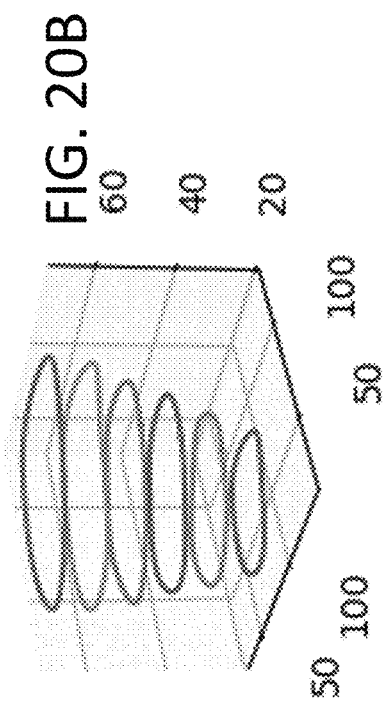
FIGS. 20A-20D show data points and spline construction from the FIGS. 18A-18C identification process.
Figure 20C:
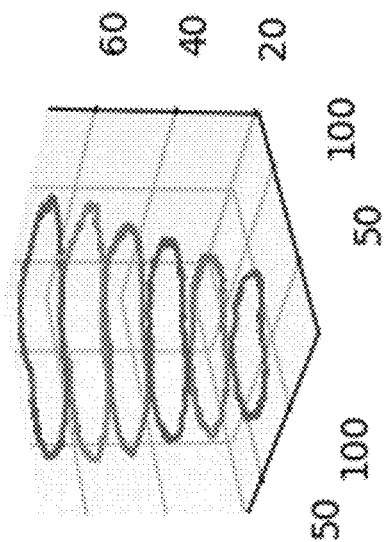
Figure 20B:
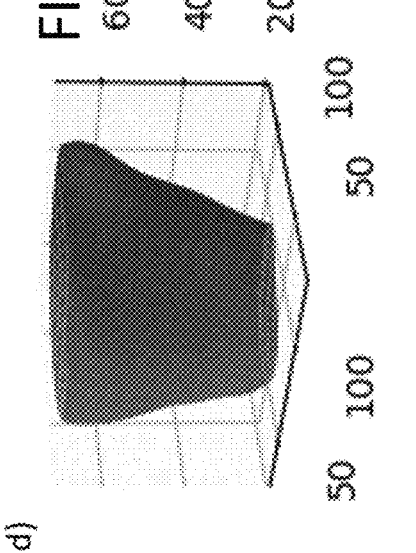

The first step in fitting the tensor-product B-spline surface to the outside of the heart surface is the extraction of contour data points from the labeled pixels in each of the image slices of the image volume. FIG. 17 shows an example labeled cardiac MRI resulting from the 3D deep convolutional network. The intended outside surface for fat thickness measurement encompasses both the left myocardium (shown in in lower right-hand labelled chamber in FIG. 17) and the right myocardium (shown in upper left-hand labelled chamber shown in FIG. 17). To identify the "outside points" the centroid of the right myocardium pixels is identified and a ray is cast outward at angles from zero to 360°. An outside point is identified as the last intersected left or right myocardium pixel that the ray intersects at each angle outward from the centroid point. An illustration of this process for the right ventricle is shown in FIGS. 18A-18C and an example of the outside points from both the left and right ventricles for each image slice in a scan is shown in FIG. 20A. FIGS. 19A-19B show how degree of overlap between the intersection contours and traced contours (from FIGS. 18A-18AC) can be used to locate the correct placement and orientation of the ultrasound image plane with respect to the 3D heart geometry, as represented by the MRI-derived model. FIG. 20B shows resampled FIG. 20A data, and FIGS.

20C and 20D the correct placement and orientation of the ultrasound image plane with respect to the 3D heart geometry, as represented by the MRI-derived model via a control point mesh and a 3D spline surface.

The process for extraction of outside points is repeated for each image slice in the volume, resulting in a series of outside points, representing the outside surface of the heart encompassing both the left and right myocardium. However, these points are not sampled uniformly in each direction, mainly due to the 1-cm-spacing between short-axis image slices. To determine a smooth surface for the heart model from this data, a tensor product B-spline surface is fit to the outside sample points. The B-spline surface fit accomplishes two main objectives, it will allow mapping of a 2D parameter space to the 3D coordinates of the object and it will provide interpolation and smoothing between the anisotropic sampling of the outside surface points between slices.

As a precursor to the 3D surface fitting, the data points extracted and derived as "outside" points for each image slice as described above required resampling to have the same number of points on each image slice. A 2D closed B-spline curve was fit to these points and used for smoothing and resampling. A B-spline curve is defined as a linear combination of a set of basis functions where the coefficients are the coefficients for these basis functions, as shown in Equation (23):

$$P(t) = \sum_{i=0}^{n} b_i N_{i,d}(t) \quad (23)$$

where d is the degree of the curve and the basis functions N, and $t_0, \ldots, t_m$ is a knot vector defined on the interval $[t_d, t_{m-d}]$. The number of knots is m+1 and the number of control points is n+1. The number of knots and control points are related by m=n+d+1. The basis functions $N_{i,d}(t)$ are defined recursively as noted below in Equations (24) and (25), using the example knot vector t:

$$N_{i,0}(t) = \begin{cases} 1 & t \in [t_i, t_{i+1}) \\ 0 & \text{otherwise} \end{cases} \quad (24)$$

$$N_{i,d}(t) = \frac{t - t_i}{t_{i+d} - t_i} N_{i,d-1}(t) + \frac{t_{i+d+1} - t}{t_{i+d+1} - t_{i+1}} N_{i+1,d-1}(t). \quad (25)$$

If the knot vector has repeated values and a 0/0 condition is encountered, it is assumed that 0/0=0.

For the curve fitting process, the points on the curve, P(t) in Equation (23) above, are known and the location of the control points b to best fit these data points are not known. To perform the curve fitting, a knot vector $t_0, \ldots, t_m$ is assigned, but an additional parameter value along the curve is required for each data point. They are calculated based on the cumulative arc length as you traverse the data points around the curve and assigned to the variable $\tau_0, \ldots, \tau_k$ for each of the $P_0, \ldots, P_0$ data points. Based on this formulation, Equation (26) can be used to solve for the control points b using a least-squares process. For k data points and n control points (with n<k), the collocation matrix A can be created as shown in Equation (26):

$$\begin{bmatrix} P_o \\ P_1 \\ \vdots \\ P_k \end{bmatrix} = \begin{bmatrix} N_0(\tau_0) & N_1(\tau_0) & \ldots & N_n(\tau_0) \\ N_0(\tau_1) & N_1(\tau_1) & \ldots & N_n(\tau_1) \\ \vdots & \vdots & \ddots & \vdots \\ N_0(\tau_k) & N_1(\tau_k) & \ldots & N_n(\tau_k) \end{bmatrix} \begin{bmatrix} b_0 \\ \vdots \\ b_n \end{bmatrix}. \quad (26)$$

The control point matrix can then be solved for using the pseudo-inverse of the collocation matrix A as shown in Equation (27):

$$b = (A^T A)^{-1} A^T P \quad (27)$$

To ensure that you obtain a closed B-spline curve fit to the data points, there are an additional 'd' control points at the end that must equal the first 'd' control points where $b_{n+1}=b_0$, $b_{n+2}=b_1$, up to $b_{n+d}=b_{d-1}$. To guarantee the last 'd' control points equal the first 'd' control points, the collocation matrix must be constrained as shown for an example cubic B-spline closed curve fit in Equation (28):

$$\begin{bmatrix} P_o \\ P_1 \\ \vdots \\ P_k \end{bmatrix} = \begin{bmatrix} N_0(\tau_0)+N_{n+1}(\tau_0) & N_1(\tau_0)+N_{n+2}(\tau_0) & N_2(\tau_0)+N_{n+3}(\tau_0) & N_3(\tau_0) & \ldots & N_n(\tau_0) \\ N_0(\tau_1)+N_{n+1}(\tau_1) & N_1(\tau_1)+N_{n+2}(\tau_1) & N_2(\tau_1)+N_{n+3}(\tau_1) & N_3(\tau_1) & \ldots & N_n(\tau_1) \\ \vdots & \vdots & \vdots & \vdots & \ddots & \vdots \\ N_0(\tau_k)+N_{n+1}(\tau_k) & N_1(\tau_k)+N_{n+2}(\tau_k) & N_2(\tau_k)+N_{n+3}(\tau_k) & N_3(\tau_k) & \ldots & N_n(\tau_k) \end{bmatrix} \begin{bmatrix} b_0 \\ \vdots \\ b_n \end{bmatrix}. \quad (28)$$

An example closed B-spline curve fits of the outside points from each of the image slices is shown in FIG. 20B. The control points that are calculated for the B-spline fit for the outside points on each image slice are resampled to have the same number of points by recalculating them using Equation (23). For a tensor product B-spline surface fit to the outside points derived from all the image slices, we extend Equation (23) to encompass the basic relationship between the 2D parameterization and the 3D surface points as shown in Equation (29):

$$P(u, v) = \sum_{i=0}^{m} \sum_{j=0}^{n} b_{i,j} N_{i,d}(u) N_{j,e}(v). \quad (29)$$

Where P are the surface points as a function of the (u, v) parameterization of the surface and have x, y, and z components for the 3D coordinates. b are the control points of the spline surface and also have x, y, and z components for the 3D coordinates. They are an (m+1) by (n+1) network of control points in the u and v directions, respectively. A series of "knots" would be defined for both directions of the parameterization: $s_0, \ldots, s_p$ for the u parameterization direction and $t_0, \ldots, t_q$ for the v parameterization direction. The knots of a spline surface are the boundaries between the basis functions N(u) and N(v). The degree of the basis functions can be set differently for each direction if desired and is noted by d and e in Equation (7) above. The basis functions are defined the same as in the 2D curve fitting case shown above in Equations (24) and (25).

The points detected that represent the outside of the left and right myocardium roughly form a cylinder-type shape with the "top" and "bottom" open (see FIG. 20B). For the B-spline surface to represent this shape correctly, the number of knots in the u direction is p+1 and is related to the number of control points for that direction by p=m+d+1 where m+1 is the number of control points and d is the degree of the basis functions. To close the surface in this direction using the degree d basis function, there are an additional d control points at the end that must equal the first d control points, similar to the closed 2D case described above.

Using the grid of parameterized data with M columns and N rows, the mesh of control points of the surface can now be determined. Using Equation (30) and letting $A_i(u_r)=N_{i,d}(u_r)$ for r=0, ..., M and $C_j(v_s)=N_{j,e}(v_s)$ for s=0, ..., N, yields the matrix equation shown below:

$$P=AbC^T \quad (30)$$

where P is the (M+1) by (N+1) matrix of data points, A is the (M+1) by (m+1) collocation matrix for u, and b is the (m+1) by (n+1) matrix of control points, and $C^T$ is the (n+1) by (N+1) collocation matrix for v. Using this matrix equation, the control points b can be obtained using the same strategy as in the 2D case with pseudoinverse matrices of A and $C^T$ as shown in Equation (31):

$$b=(A)^{-1}P(C^T)^{-1}. \quad (31)$$

Figure 20D:
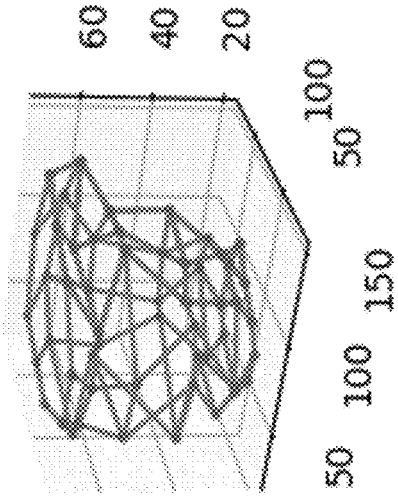

Equation (31) is used for x, y, and z coordinates and the first three columns of control points are repeated as three additional columns at the end to ensure the appropriate closed behavior in the u direction. An example surface fit of the outside points is shown in FIG. 20B, where the control point mesh is shown in FIG. 20C and the resulting tensor product B-spline surface is shown in FIG. 20D.

To obtain closed tensor product B-spline surfaces for the left endocardium surface and the left epicardium surface, the same strategy of a cylindrical-style surface fit can be used. However, the process for determining the P data points to be is more straightforward for those surfaces because the endocardial and epicardial boundaries of the left myocardium are often nearly circular in cross-section. The points are determined by extracting boundary contours from the labeled left myocardium pixels in each image slice. After that, the same surface fitting process is applied to both the endocardial and epicardial surfaces.

Example 8. Interpolating and Parameterizing the Heart Surface Using Registration of Average Heart Model Shape to Labeled Cardiac MRI Tissue Types As an alternative to the methodology described in Example 7, if the labeled tissue types are inconsistent, noisy, or have large gaps, the direct fit of the tensor-product B-spline surface can be unwieldy and not reflect the heart shape in a manner suitable for fat thickness measurement and mapping. To help mitigate that scenario, a second approach was developed that involves an intermediate step of fitting a previously-developed average shape model to the labeled pixels in each of the image slices of the image volume.

Figures 21A, 21B:
FIGS. 21A-21B show a process in which an average heart shape model placed in the 3D coordinate system of the labeled image data and the intersection of the shape model surfaces with the cardiac MRI image planes.

The agreement between the average shape model and the labeled data is assessed using the left myocardium because it is the most consistently correct labels. First, the average shape model is placed in the 3D coordinate system of the labeled image data and the intersection of the shape model surfaces with the cardiac MRI image planes are used to generate contours outlining the anatomical structures in the image planes as shown in FIGS. 21A and 21B. The intersected contours from the shape model left myocardium are filled-in with pixels for comparison to the left-myocardium-labeled pixels from the convolutional network (see FIGS. 22A and 22B). The shape model is modified with affine transformations, included translation, rotation, and scaling, to maximize the agreement between the left myocardium resulting from the shape model intersection and the left myocardium from the convolutional network. The agreement is measured using Dice similarity coefficient (DSC), as shown by Equation (32):

$$DSC = \frac{2|A \cap B|}{|A|+|B|} \quad (32)$$

where A is the number of pixels of left myocardium from the intersected shape model and B is the number of pixels of left myocardium from the convolutional network output. To determine the appropriate set of affine transformations to place the average shape model in the 3D data, there are 9 parameters required, including x, y, and z components for each of scale, translate, and rotate. The global optimization problem was formulated by using an objective function by adding together the DSC across each of the image slices in the volume, as shown below in Equation (33):

$$f = \frac{1}{N}\sum_{i=0}^{N-1}(1-DSC_i) \quad (33)$$

where $f$ is the objective function to minimize and N is the number of image slices in the volume. A simulated annealing algorithm that identifies the global minimum is then used to determine the optimal 9 affine transformation parameters. After the average shape model is fit to the labeled data, a tensor-produce B-spline surface is fit to the outside points of the shape model in the same manner as described in Example 7 to provide the same 2D parameterization of the outside surface of the heart.

Figures 23A, 23B, 23C:
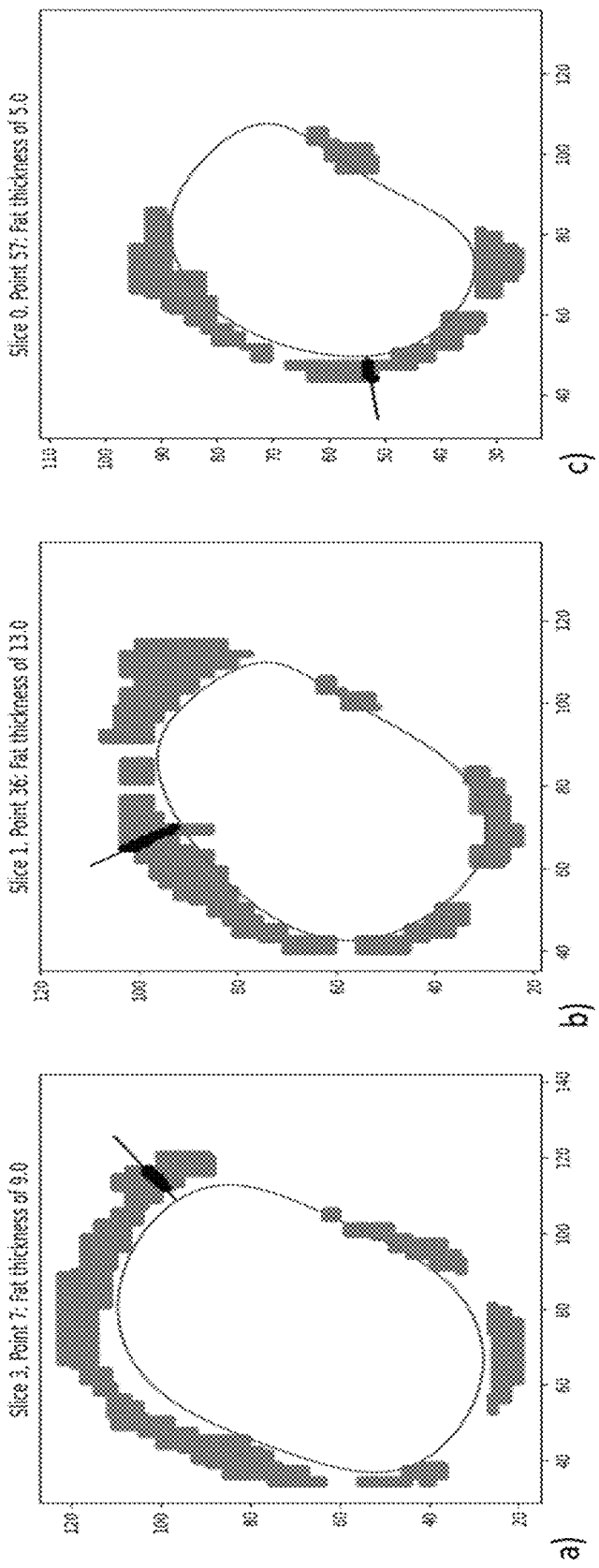
FIGS. 23A-23C show that a vector is created normal to the intersected contour and the fat thickness at that location is determined to be the number of labeled fat pixels that a line in the direction of that normal vector intersects, as illustrated for several different image slice contours and parameterization locations.

Example 9. Mapping Fat Thickness and Integrating the Fat Model into the 3D Average Model For the ninth example, the tensor-product B-spline surface parameterization from Example 7 provides a 2D coordinate system for locating specific points on the surface of the left or right myocardium. The MRI image planes, spaced 1 cm apart throughout the volume, provide the labeled cardiac fat pixels, that are used to measure the fat thickness. The intersection of the MRI image plane and the tensor-product B-spline surface model of the heart, both left and right sides, yields contours in the image plane that define the surface locations corresponding to that image plane. The B-spline parameterization in the direction around the contour is used to make fat thickness measurements at known locations. At each of the positions around the contour, a vector is created normal to the intersected contour and the fat thickness at that location is determined to be the number of labeled fat pixels that a line in the direction of that normal vector intersects, as illustrated for several different image slice contours and parameterization locations in FIGS. 23A-23C. These measurements are taken at positions around the contour for each image plane where there is an intersected contour.

Figure 24B:
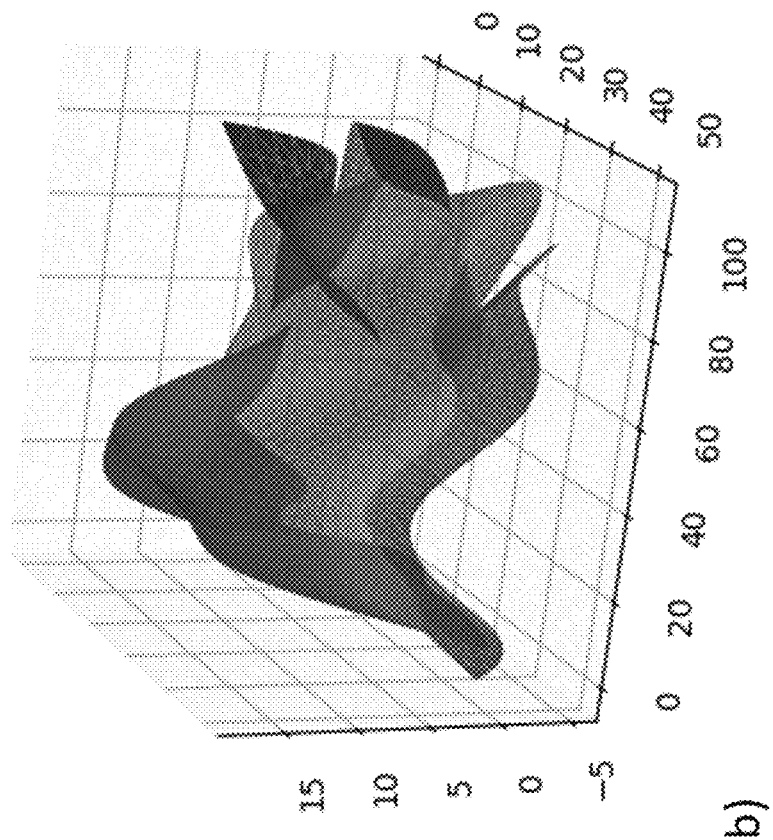
FIG. 24A-24B respectively show (A) an example 3D stem plot, showing the thicknesses at different locations in a 2D parameterization around the 3D surface of the heart and (B) an illustration of the fat surface fit to the 2D parameterization of the fat thickness measurements.
Figure 24A:
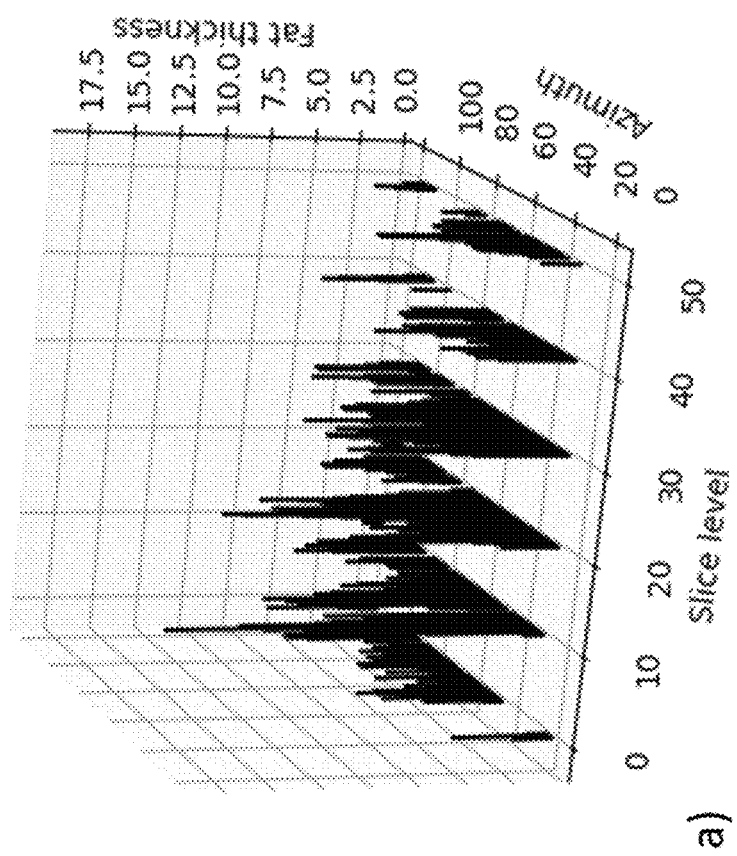
Figures 25A, 25B, 25C:
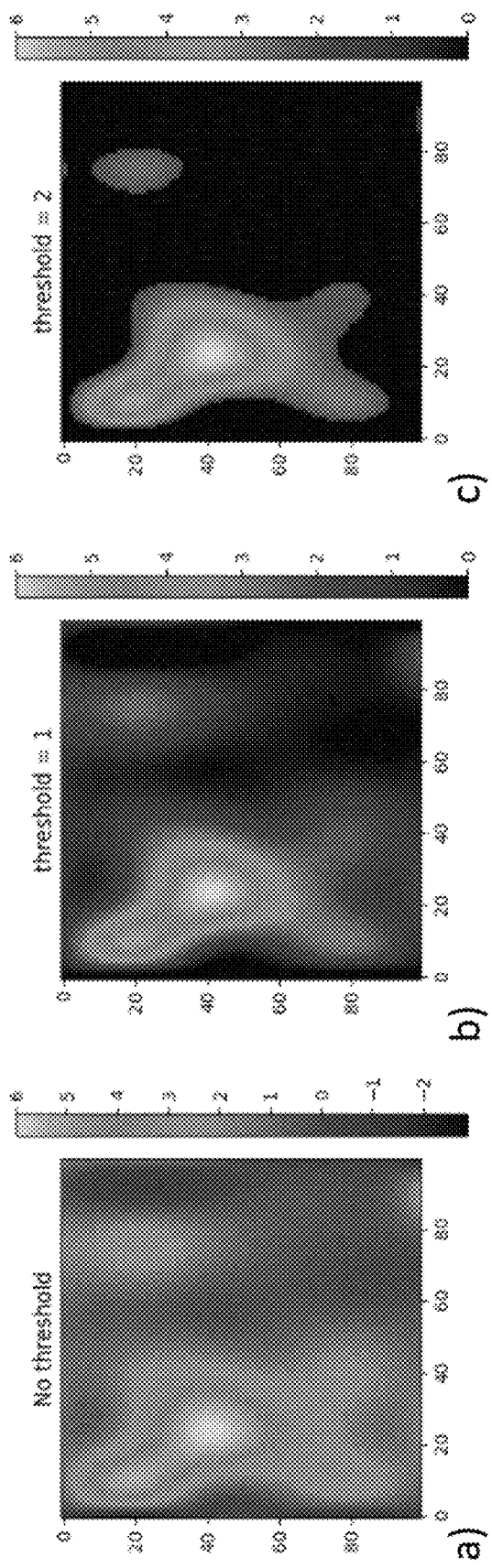
FIGS. 25A-25C show example fat maps presented in a color-mapped (grayscale) format and in a color-mapped (grayscale) format with optional thresholds for minimal fat thicknesses.

The resulting thickness measurements are sparse, particularly in the direction along the image slices (1 cm apart). An example 3D stem plot, showing the thicknesses at different locations in the parameterization is shown in FIG. 24A. To determine a smooth representation and interpolate those sparse samples, the next step is to fit another tensor-product B-spline surface to the fat thickness measurements in the 2D coordinate system of the parameterization of the outside heart surface. The topology in this case is different than that described in Example 7, which formulated the surface fitting problem in a cylindrical format with one direction closed on itself and the other open. The surface fit in this case is open in both directions, but clamped to the ends, i.e., the surface extends all the way to the last data points in both the u and v directions. To clamp the surface in both directions, the knots at the beginning and end of the knot vector must be repeated d+1 times for a degree dB-spline surface. The resulting surface reflects the topography of the fat thickness across the outside surface of the heart, parameterized in two directions, one moving around the circumference of the heart and one moving along the axis of the heart. An illustration of the fat surface fit to the 2D parameterization of the fat thickness measurements is shown in FIG. 24B. FIGS. 25A-25C show example fat maps presented in a color-mapped (grayscale in the figures) format and in a color-mapped (grayscale) format with optional thresholds for minimal fat thicknesses.

The approach to creating a parameterized fat mapping around the surface of the heart described in Example 7 can be performed on numerous 3D cMRI scans, resulting in a fat map for each scan. An average fat map can be computed simply by averaging the fat maps across the different (u, v) coordinate pairs in the parameterization. A tensor-product B-spline spline surface fit, as described in Example 7, can be performed on the average shape model, providing a (u, v) parameterization around the outside of both left and right sides of the heart. The (u, v) parameterization of the average fat map and the (u, v) parameterization of the outside surface of the shape model provide the connection that can be used to integrate the average fat thickness to the average shape model.

To formulate the average fat surface model as a 3D polygon data structure, new 3D fat points at each (u, v) location are required. They are computed by using the normal vector to the shape model at that location and generating the new point at a location along that vector, but at the distance away from the surface as indicated by the fat thickness measurement. The set of fat points are then triangulated into the polygonal surface representation using a Delaunay triangulation.

Example 10. Locating the Path of the Coronary Arteries Down the Heart Surface by Fitting the B-Spline Curve to Points Selected in Sparse Image Slices For the tenth example, the coronary arteries are embedded in the layer of cardiac fat and are observable in the cardiac magnetic resonance images (cMRI). One approach to identifying the path of the coronary arteries down the surface of the heart would involve the user identifying the location of the coronary artery in several image slices from the volumetric scan. The location of the coronary arteries in the image slices, along the length of the scan, forms a curve in three-dimensional space. The x and y locations of the coronary artery locations in the image planes, combined with the z location of those specific image planes, forms the (x, y, and z) coordinates of sample points along the path of the coronary artery in three dimensions. To interpolate a curve along the path of the coronary, a 3D B-spline curve can be fit to the sample points that are entered by the user or determined automatically via the 3D Unet in Example 6. A B-spline curve is defined as a linear combination of a set of basis functions where the coefficients are the coefficients for these basis functions, as shown in Equation (34):

$$P(t) = \sum_{i=0}^{n} b_i N_{i,d}(t) \tag{34}$$

where d is the degree of the curve and the basis functions N, and $t_0, \ldots, t_m$ is a knot vector defined on the interval $[t_d, t_{m-d}]$. The number of knots is m+1 and the number of control points is n+1. The number of knots and control points are related by m=n+d+1. The basis functions $N_{i,d}(t)$ are defined recursively as noted below in Equations (35) and (36), using the example knot vector t:

$$N_{i,0}(t) = \begin{cases} 1 & t \in [t_i, t_{i+1}) \\ 0 & \text{otherwise} \end{cases} \tag{35}$$

$$N_{i,d}(t) = \frac{t - t_i}{t_{i+d} - t_i} N_{i,d-1}(t) + \frac{t_{i+d+1} - t}{t_{i+d+1} - t_{i+1}} N_{i+1,d-1}(t). \tag{36}$$

If the knot vector has repeated values and a 0/0 condition is encountered, it is assumed that 0/0=0.

For the curve fitting process, the points on the curve, P(t) in Equation (34) above, are known and the location of the control points b to best fit these data points are not known. To perform the curve fitting, a knot vector $t_0, \ldots, t_m$ is assigned, but an additional parameter value along the curve is required for each data point. They are calculated based on the cumulative arc length as you traverse the data points around the curve and assigned to the variable $\tau_0, \ldots, \tau_k$ for each of the $P_0, \ldots, P_0$ data points. Based on this formulation, Equation (37) can be used to solve for the control points b using a least-squares process. For k data points and n control points (with n<k), the collocation matrix A can be created as shown in Equation (37):

$$\begin{bmatrix} P_o \\ P_1 \\ \vdots \\ P_k \end{bmatrix} = \begin{bmatrix} N_0(\tau_0) & N_1(\tau_0) & \ldots & N_n(\tau_0) \\ N_0(\tau_1) & N_1(\tau_1) & \ldots & N_n(\tau_1) \\ \vdots & \vdots & \ddots & \vdots \\ N_0(\tau_k) & N_1(\tau_k) & \ldots & N_n(\tau_k) \end{bmatrix} \begin{bmatrix} b_0 \\ \vdots \\ b_n \end{bmatrix}. \tag{37}$$

The control point matrix can then be solved for using the pseudo-inverse of the collocation matrix A as shown in Equation (38):

$$b = (A^T A)^{-1} A^T P. \tag{38}$$

In addition, each of the (x, y, and z) coordinates that are calculated as the interpolated and smoothed path in 3-space also correspond to (u, v) coordinate pairs in the 2D parameterization as described in the fat modeling procedures (Example 9). This set of (u, v) coordinate pairs defines a path in the parameterized fat map.

Figure 26B:
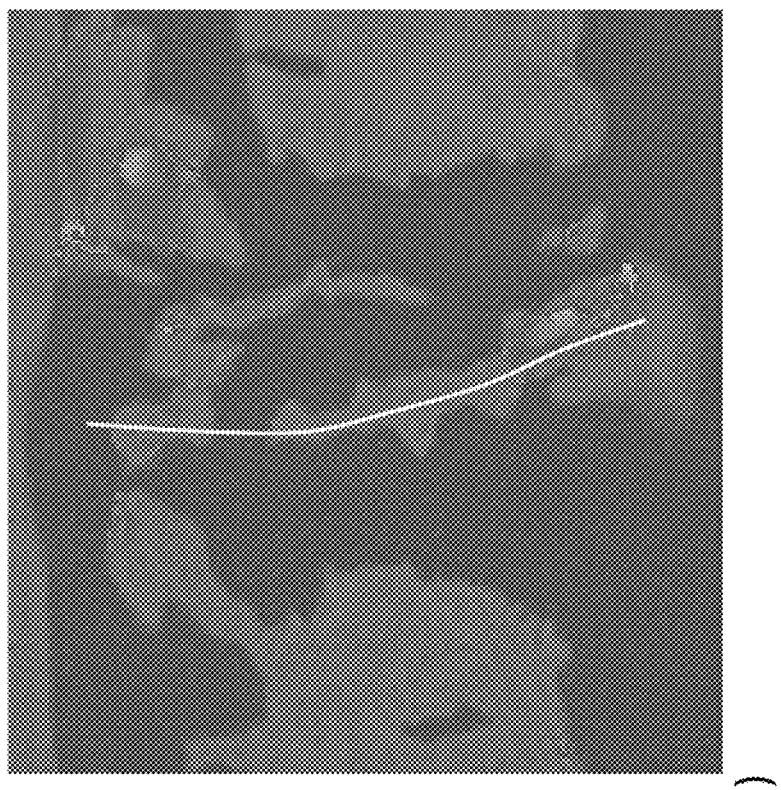
FIGS. 26A-26B illustrate a set of (u, v) coordinate pairs that define an artery path in a parameterized fat map.
Figure 26A:
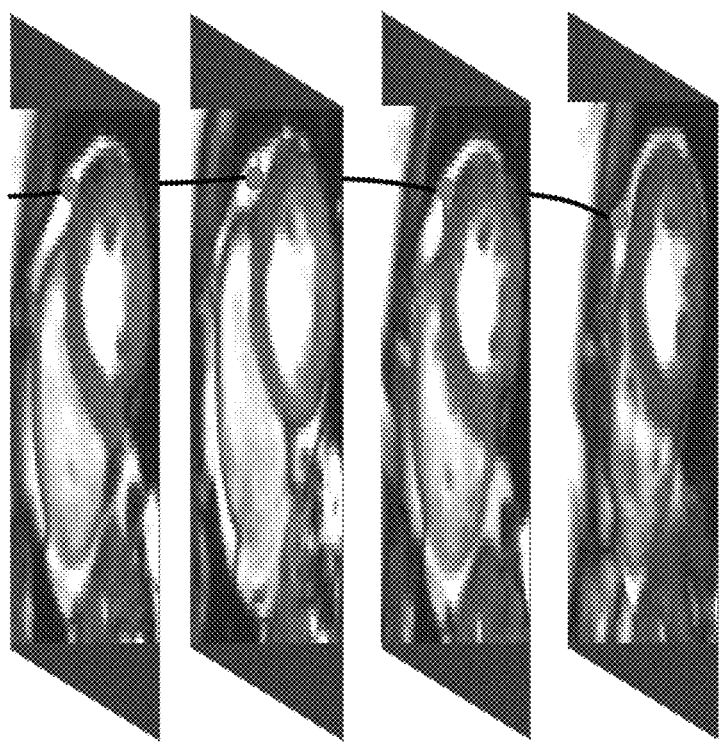
Figure 27:
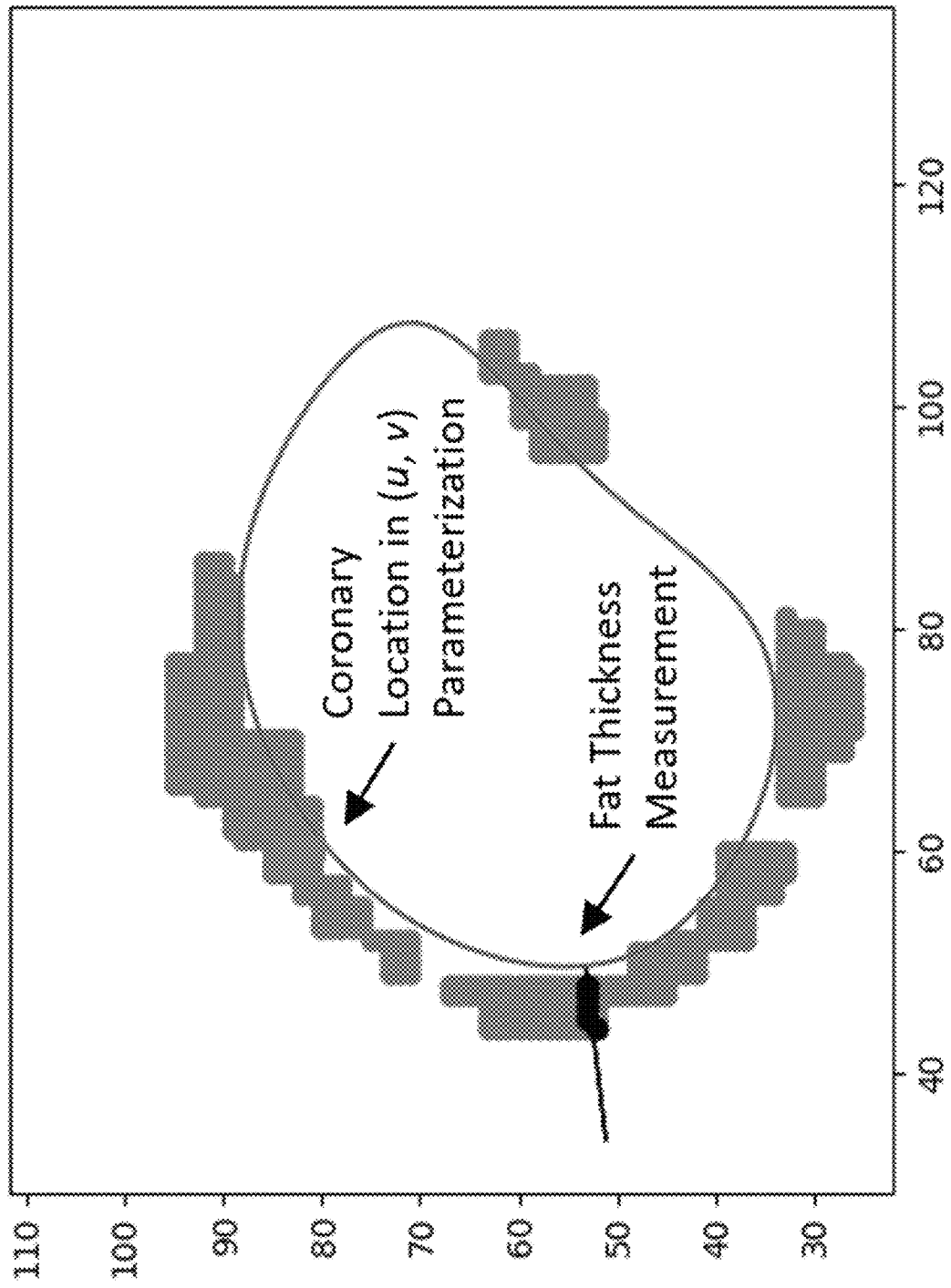
FIG. 27 shows a selected slice of heart image data with fat thicknesses and coronary location identified.

Example 11. Locating the Part of the Coronary Arteries Down the Heart Surface by Ray Intersection with Labeled Voxels For the eleventh example, the second approach to identifying the path of the coronary artery down the surface of the heart is reliant on consistently identified coronary artery locations in the transverse cMRI images, as shown in FIGS. 26A and 26B. The method for measuring fat thickness (described in Example 9) can also be used to locate the coronary arteries through the labeled pixels, as shown in an example slice in FIG. 27. Using this approach, the location of the coronary artery points can also be determined in the (u, v) parameterization of the fat map and outside surface of the heart in each image slice of the scan. Interpolating and smoothing the (u, v) coordinate pairs in the parameterization would also produce a coronary path in the fat map as shown FIG. 26B. A clamped B-spline curve can be used to perform this fitting, interpolating, and smoothing, like the 3D curve fit described above in Example 10, but restricted to the (u, v) 2D coordinate system and using the u and v parameterization variables that correspond to location on the heart surface as the components of the b and P.

Example 12. Quantifying the Local Fat Volume Along the Coronary Artery Path

Figure 28B:
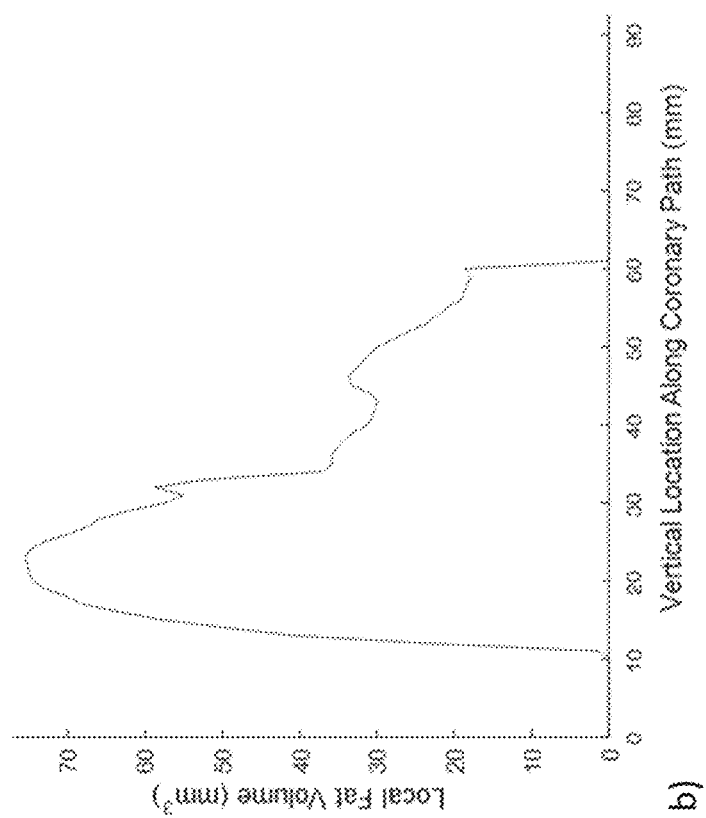
FIG. 28A-28B show (A) a fat map with coronary location information and (B) a plot of local fat volume versus coronary vertical location.
Figure 28A:
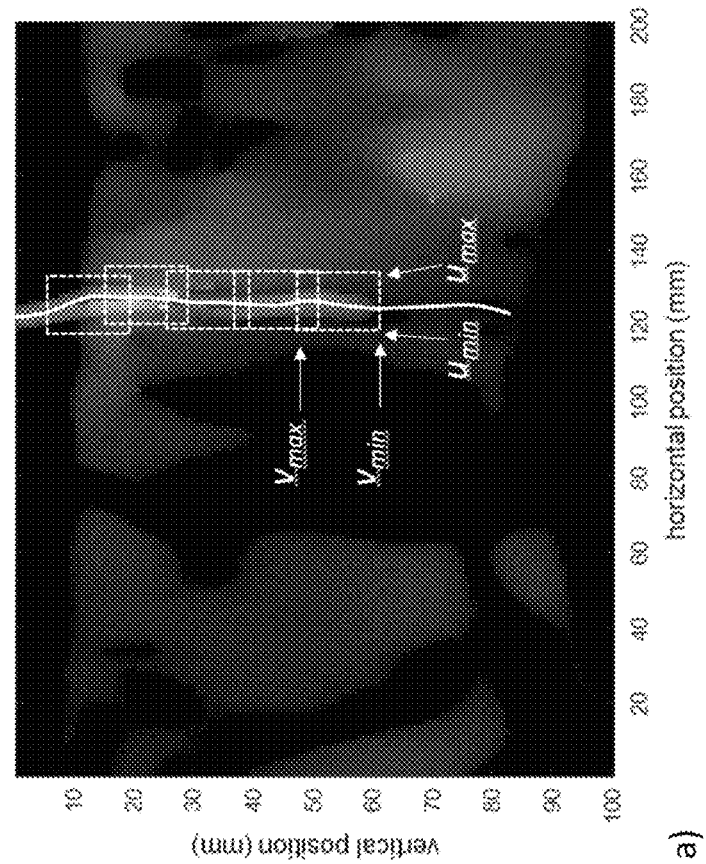

For the twelfth example, after determination of the coronary path down the surface of the heart, indicated by the curve fit in the (u, v) parameterized coordinate system, the next step is to calculate the volume of cardiac adipose tissue in close proximity to the coronary artery. FIG. 28A shows a fat map, where the fat thickness is indicated in the shades (the image is grayscale, but colors are preferred for indications of the fat thickness, such as shade of green for fat), the location of the coronary is a different shade (preferably a different color, e.g., purple), and the path of the coronary down the surface of the heart is indicated by the white curve. FIG. 28B shows a plot of local fat volume versus coronary path length. Local regions for measurement of fat volume in proximity to the coronary artery are indicated by the dashed white boxes. The fat thickness map can be represented as a function of fat thickness versus the (u, v) parameterization—f(u, v). Given this 2D fat thickness function, the local fat volume along the length of the coronary artery path, g(s), where u(s) and v(s) are computed by the B-spline curve fit described in Example 10 above can be computed as shown in Equation (39):

$$g(s) = \int_{v_{min}}^{v_{max}} \int_{u_{min}}^{u_{max}} f(u(s), v(s)) du dv \qquad (39)$$

where $v_{min}$ and $v_{max}$ define the bottom and top of the rectangular region of integration and $u_{min}$ and $u_{max}$ define the horizontal bounds of the region of integration.

Figures 29A, 29B:
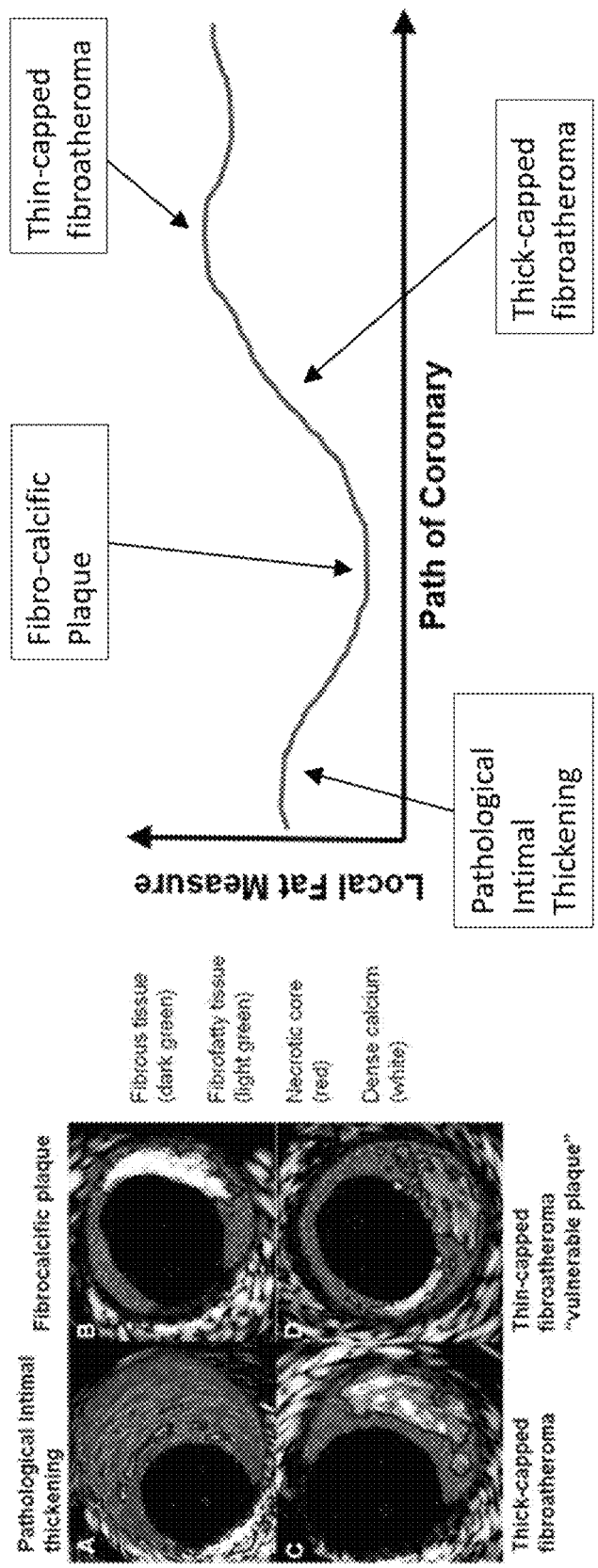
FIGS. 29A-29B illustrate an example use of classification algorithms, including convolutional networks or traditional neural networks (among others), trained to predict the plaque type from only the fat map.

The fat map and the local fat map quantification can also be used as a prediction for the specific presence and type of coronary artery disease (CAD). For example, if intravascular ultrasound (IVUS) images are used to identify the presence of plaque and the plaque type (vulnerable vs. not vulnerable), then a pattern in the fat map and the local fat plot (FIGS. 28A & 28B) can be trained to identify the location and type of coronary plaque. Coronary plaque characterization algorithms performed on the IVUS data can be used to classify plaques into one of several different plaque phenotypes. If the IVUS data is available in patients that undergo cardiac MRI, the link between the fat map, including the local fat measurement, and the plaque type can be established. Classification algorithms, including convolutional networks or traditional neural networks (among others) can be trained to predict the plaque type from only the fat map. Example coronary plaque types are shown in FIG. 29A and possible indications of them in the local fat plot are shown in FIG. 29B.

Example 13. Quantifying the Local Fat Volume Along the Coronary Artery Path

For the thirteenth example, an alternative approach for providing the registration algorithm for the MRI-derived model with the ultrasound plane. This example focuses on a process which leverages the visibility of CAT in MRI to bolster the effectiveness of echocardiography in identifying CAT given the high signal-to-noise-ratio (SNR) of MRI makes it an invaluable tool for identifying CAT. This process is comprised of four primary steps, which are as follows:

1. Extraction of tissue type information from MRI volume data;
2. Development of continuous 3D representation of the patient's heart muscle and CAT;
3. Registration of patient ultrasound data with 3D MRI-derived heart model; and
4. Tissue type labelling in ultrasound and training of tissue classifier.

The first of these steps is facilitated using a 3D UNET convolutional neural network. The UNET performs image segmentation on MRI slice data, identifying regions belonging to four tissue categories: left myocardium, left ventricle (blood), right myocardium, and cardiac fat.

Figure 30:
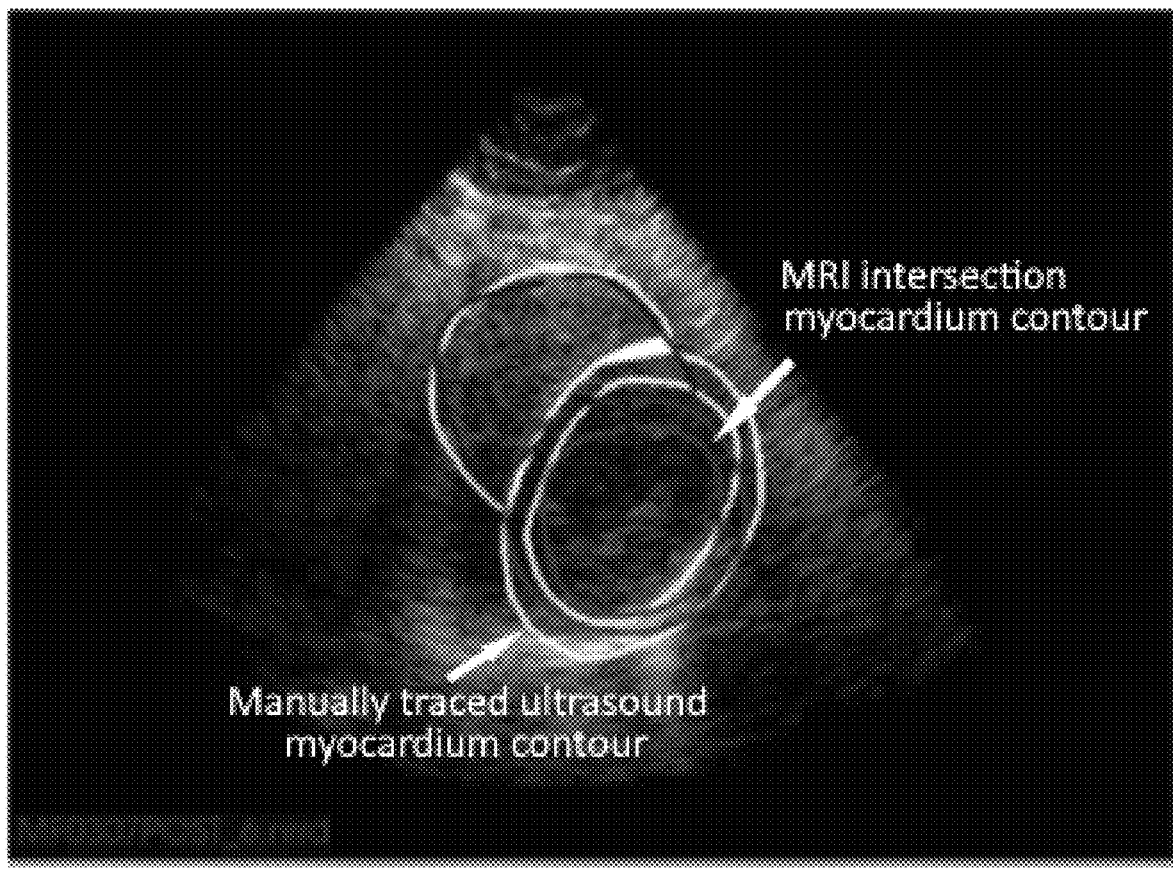
FIG. 30 shows MRI contours generated by intersecting the MRI model with the ultrasound plane.

The 3D UNET segmentation labels become the basis for creating a smooth 3D representation of the patient's heart. The goal is to perform image registration between the MRI and ultrasound, and to use the labelled MRI to label corresponding regions in the ultrasound. The segmented MRI data alone are insufficient for this purpose because of the significant anisotropy of the MRI volumes. The MRI data are comprised of slices which are acquired at 1-cm intervals along the vertical axis, meaning that segmentation information is not explicitly available in the regions between slices. Echocardiography requires that ultrasound scans be acquired by placing the transducer between the ribs of the patient, leading to images which typically cannot be aligned perfectly with the corresponding MRI slice data. As such, any attempt at registering the two data sets and labelling regions in the ultrasound will require interpolation of the MRI volume to address this anisotropy. This interpolation is accomplished using B-spline modelling. Using the UNET labels as its input, this method achieves a direct 3D surface fit by means of a 2D B-spline parameterization. The CAT thickness at each location on the surface of the heart is also assessed for each MRI slice by quantifying segmented fat normal to the surface at regular intervals (an example slice is shown in FIG. 30), and B-spline interpolation is leveraged to make fat thickness predictions for locations between slices. A custom 3D triangulation routine is then used to generate a 3D representation of the CAT in relation to the surface of the heart, even in locations between MRI slices for which segmentation information is not explicitly available.

Once the MRI has been leveraged to generate a sufficiently detailed 3D representation of the anatomy of the patient, image registration is used to establish spatial correlation between the MRI-derived model and a 2D ultrasound plane from the same patient. This registration is facilitated using the outlines of the left and right ventricles, which can be visually identified in images of both modalities. The left and right ventricles are traced in the ultrasound scans by a human observer or identified automatically as described in Example 14, while the MRI contours are generated by intersecting the MRI model with the ultrasound plane (FIG. 30). The geometry of this plane is described in terms of the set of translations and rotations in 3D space that are necessary to simulate the location of the ultrasound probe relative to the heart during image acquisition. The intersection creates a set of contours representing the left myocardium, right myocardium, and cardiac fat, which are superimposed onto the ultrasound plane. The degree of overlap between the intersection contours and traced contours may then be used to locate the correct placement and orientation of the ultrasound image plane with respect to the 3D heart geometry. The agreement between the contours is quantified using a difference metric which integrates contour centroid and curve length information for each tissue type. A gradient-based optimization algorithm is used to minimize this difference metric, indicating a reasonable and actionable registration of the two data sets.

Figure 31:
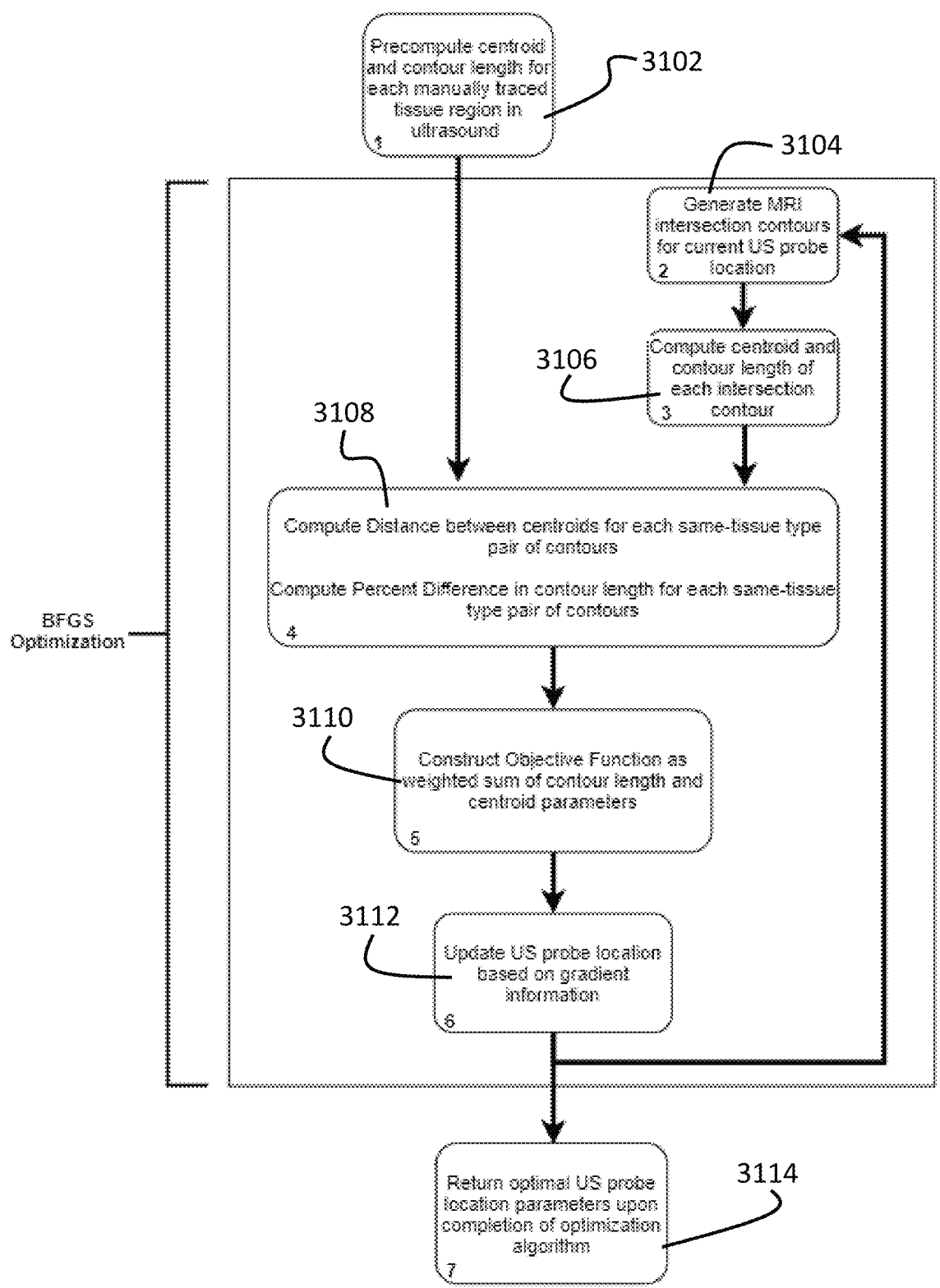
FIG. 31 is a flowchart of a preferred intersection process for intersecting ultrasound data with an MRI model.

FIG. 31 is a flowchart of a preferred process for alignment of ultrasound imaging data with a model MRI heart image. The begins with a step 3102 of the computation of the length and centroid locations of each manually traced or automatically identified ultrasound contour. This step is performed only once before optimization occurs, as the traced contours will not change during the optimization process. Next, the MRI-derived model is intersected with the ultrasound plane, whose location is described in terms of a set of translations and rotations in 3D space. This yields a set of contour points for each tissue type which characterize each tissue type region in the MRI relative to the ultrasound plane as shown in step 3104. For each of these tissue type contours, the contour length and centroid locations are computed in the same manner as the manually-traced ultrasound contours as shown in step 3106. Each pair of same-tissue type contours is then compared using two primary metrics. The first metric uses the distance between centroids of same-tissue contours to quantify the "closeness" of the contours to one another. If the distance between centroids is small, it can reasonably be inferred that the contours have a significant degree of overlap. The percent difference in length between same-tissue contours is used as the second metric. The percent difference is used to quantify the relative sizes of the contours, while removing dependence on the absolute sizes of the contours as shown in step 3108. Once these two metrics have been computed for each tissue, they are integrated into a single objective function to be minimized by the optimizer as shown in step 3110. Optionally, the metrics for each tissue type can be assigned multiplicative weights to favor specific tissue types more heavily during optimization. Steps 3104 through 3112 are preferably performed iteratively during a Broyden-Fletcher-Goldfarb-Shanno (BFGS) gradient optimization algorithm. The algorithm uses the above steps to compute the objective function to assess the degree of overlap between the two data sets. The Jacobian of the objective function is evaluated and used to determine a new set of ultrasound probe location parameters to test as shown in step 3112. Steps 3104 through 3112 are then repeated to assess whether the agreement between the data sets is improved. This process repeats until a sufficiently close alignment has been achieved, at which point the algorithm terminates and the optimal US probe location parameters needed to replicate this alignment are obtained as shown in step 3114.

When such a registration has been achieved, the MRI-derived tissue type contours superimposed on the ultrasound plane can be used to label regions within the ultrasound as belonging to a given tissue type. Of particular interest is the labelling of regions of CAT. It is then possible to extract the radiofrequency data from these regions, from which spectral parameters can be calculated. These spectral features are then used to train a tissue classifier, such that it is possible to identify CAT in ultrasound scans for which no corresponding MRI data is available.

Example 14. Ultrasound Segmentation Using Spectral Parameters

For the fourteenth example, an alternative approach for using MRI data to create a 3D representation of a patient's heart and the associated cardiac adipose tissue for use with cardiac ultrasound data from the same patient, as well as machine learning techniques, to bolster the effectiveness of ultrasound in locating and quantifying fat in situations where use of MRI is not feasible.

The development of the 3D representation of a patient's heart and the associated cardiac adipose tissue from the MRI data requires the segmentation of different tissue types from a set of 3D MRI scans. The MRI scans are gated at 1-cm increments along the cardiac short axis and looped through the cardiac cycle. The 3D volumes used are extracted from two points in the cardiac cycle loop, end-systole and end-diastole. The heart and the cardiac adipose tissue of the imaged patient are then manually segmented in the open-source medical imaging software 3DSlicer.

These manually segmented volumes were utilized to train a 3D neural network to identify and segment the critical parts of the patient's heart such as the left myocardium, right myocardium, left ventricle, and associated cardiac adipose tissue. The specific type of network used was a convolutional neural network with a U-Net architecture. This is a layered architecture using an encoder and a decoder. The network used in this case had 5 encoder levels, each consisting of two convolutional layers and a max pooling layer. Each convolutional layer used a kernel size of 3×3×3 and a Rectified Linear Unit activation function. The first encoder level implemented 16 filters for feature extraction. The number of filters doubled at each successive encoder layer. The decoder mirrored the number of levels of the encoder. Each decoder level implemented a transposed convolution layer, a concatenation with the output from the corresponding encoder level, and two more convolutional layers. A final 1×1×1 convolution was performed, ensuring the correct shape of the output prediction volumes generated by the network.

Figure 32:
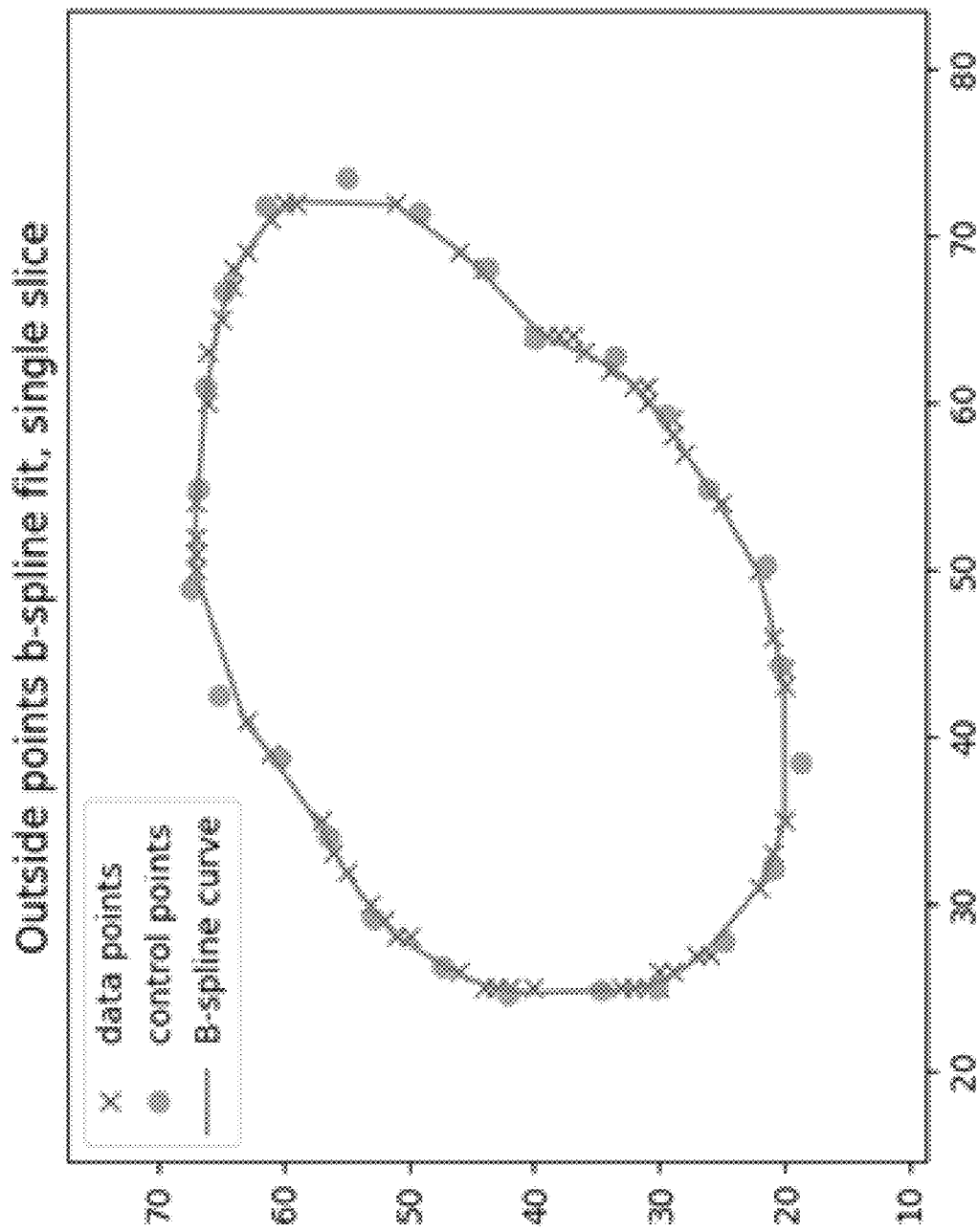
FIG. 32 shows how a U-Net determined set of points that form a contour which traces the shape of the heart muscle on each slice. The data points are indicated with an X and the control points of the best fit 2D closed B-spline curve are indicated with the dot. The best fit curve is also shown.

The set of segmentation labels produced by the U-Net provide an assessment of the patient's cardiac anatomy. However, the MRI slice planes exist only at 1-cm intervals along the vertical axis. As such, the segmentation labels must be leveraged to produce a continuous 3D representation of the patient's cardiac anatomy which interpolates between successive slice planes. This process begins with the extraction of right and left myocardium segmentation labels representing the outside surface of the heart. These points form a contour which traces the shape of the heart muscle on each slice, as seen in FIG. 32.

Once the outside points have been identified, they are used to generate a 3D B-spline model of the patient's heart. B-spline modelling provides a way of smoothly interpolating between points on a single slice, as well as interpolating the gaps between slices. FIG. 32 shows a 2D B-spline fit representing a single slice of the model. The X's represent the data points derived from the segmentation labels. From here, the data points are parameterized, and a set of control points (represented by dots in the image) defines the path of an interpolating curve (solid line) that passes through each of the data points. This process is repeated on data derived from each MRI slice, and then the 3D B-spline fitting algorithm described in Example 7 is used to interpolate between the slices. The result is a model which is closed in the parameterization direction around the heart, but open in the vertical parameterization direction.

Figure 33:
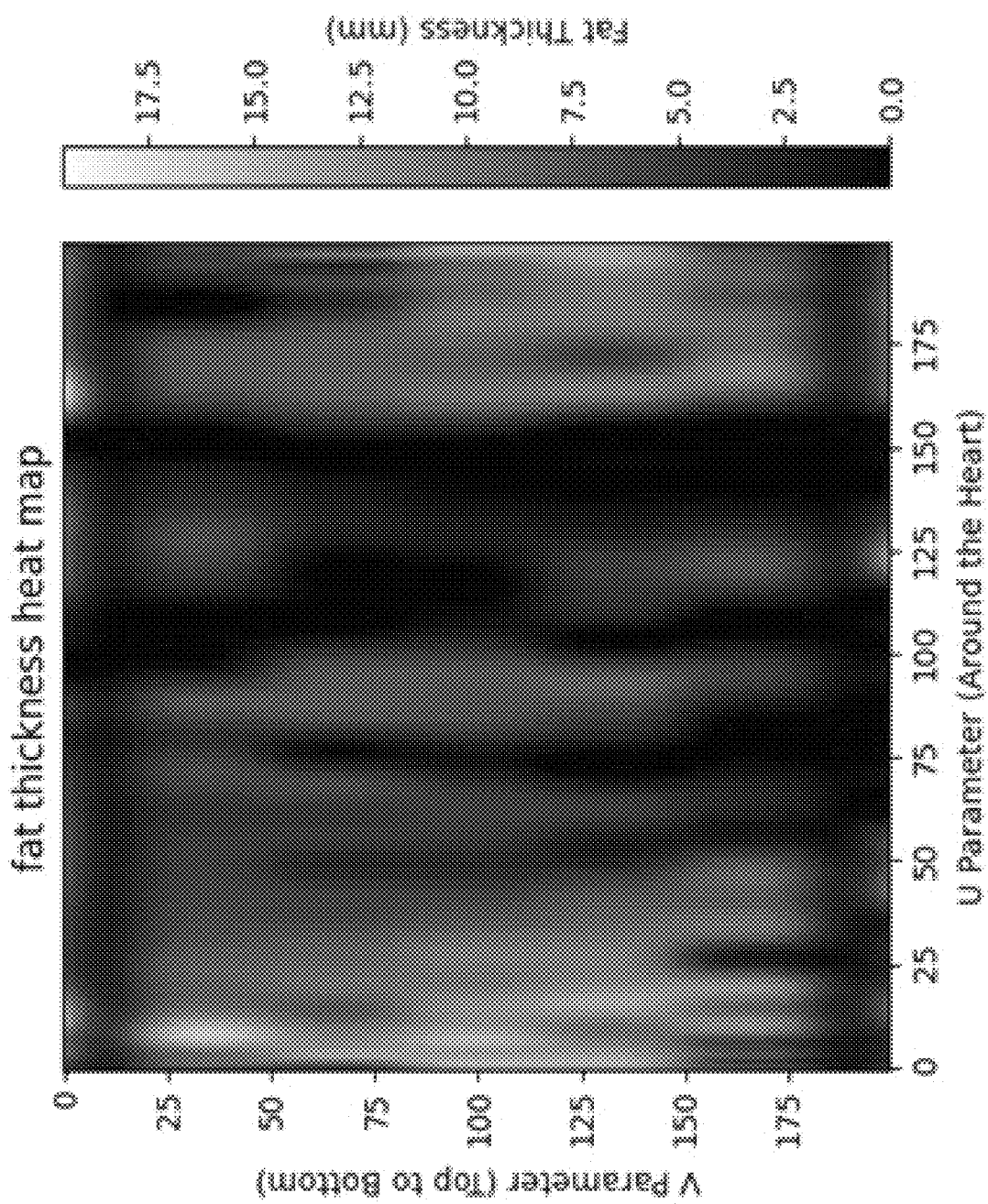
FIG. 33 is a heat map of parametric fat thickness based upon an interpolated representation of the fat thickness between input MRI slices.

Once a 3D representation of the exterior of the patient's heart has been generated, the thickness of fat around various points on the heart's surface is sampled by assessing the quantity of fat labels adjacent to the surface at each location on an MRI slice. An additional B-spline fit is then applied to these thickness measurements to provide an interpolated representation of the fat thickness between input MRI slices used to produce a parametric fat thickness map like the one seen in the heat map of FIG. 33. The vertical axis represents the "height" of the parameter location on the heart, while the horizontal axis indicates the location when rotating around the surface of the heart. The thickness of the fat at a given parameter location is denoted by the color of the pixel at that location.

Figure 34A:
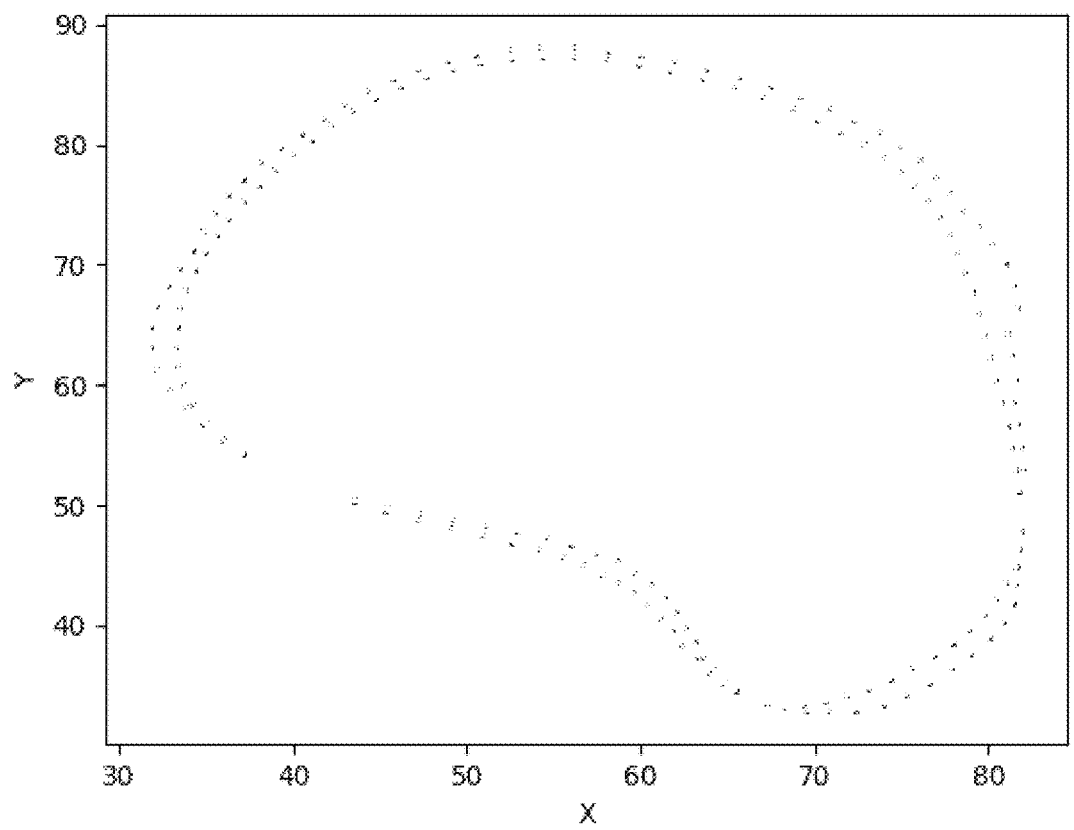
FIGS. 34A and 34B, respectively, show a set of example fat points from one MRI slice (FIG. 34A) and a set of fat points from a sequence of MRI slices with two example spanning lines demonstrating triangulation of the fat points (FIG. 35B).

A fat thickness assessment for each parameter location can be used to generate a continuous 3D surface representation of the patient's cardiac fat. For the MRI-derived model to be used effectively in MRI-ultrasound image registration and CAT region labeling, it must be possible to "slice" the model such that a set of intersection contours are produced. As such, the CAT thickness measurements are translated into a set of 3D points in a way that produces this outcome. The parameter space is separated into slices by considering each v parameter value individually. For a 100×100 parameterization, this equates to 100 slices consisting of 100 fat thickness measurements each. For each nonzero CAT thickness measurement in a given slice, two 3D points are generated. The first of these is simply the myocardium surface point corresponding with that measurement, while the second point is created by traveling away from the surface along the normal vector path a distance that is equivalent to the thickness. Repeating this process for each location with a nonzero CAT thickness produces a set of points which, when connected as contours, enclose regions of CAT. Consecutive nonzero thickness measurements are taken to be part of the same contour. Conversely, areas where no CAT is present indicate separations between distinct regions of fat on the same slice. FIG. 34A indicates a typical slice, containing multiple contours whose interiors represent non-contiguous regions of CAT.

Figure 34B:
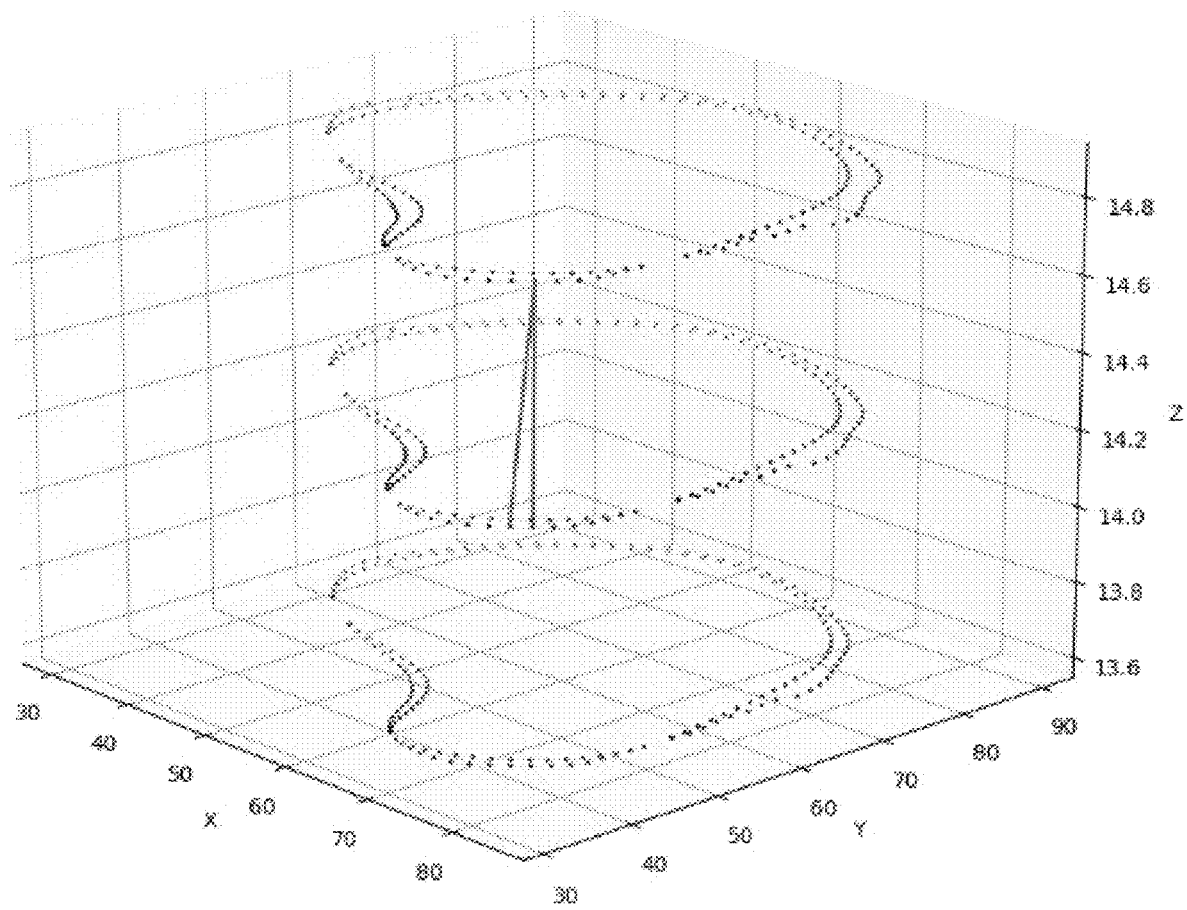
Figure 35:
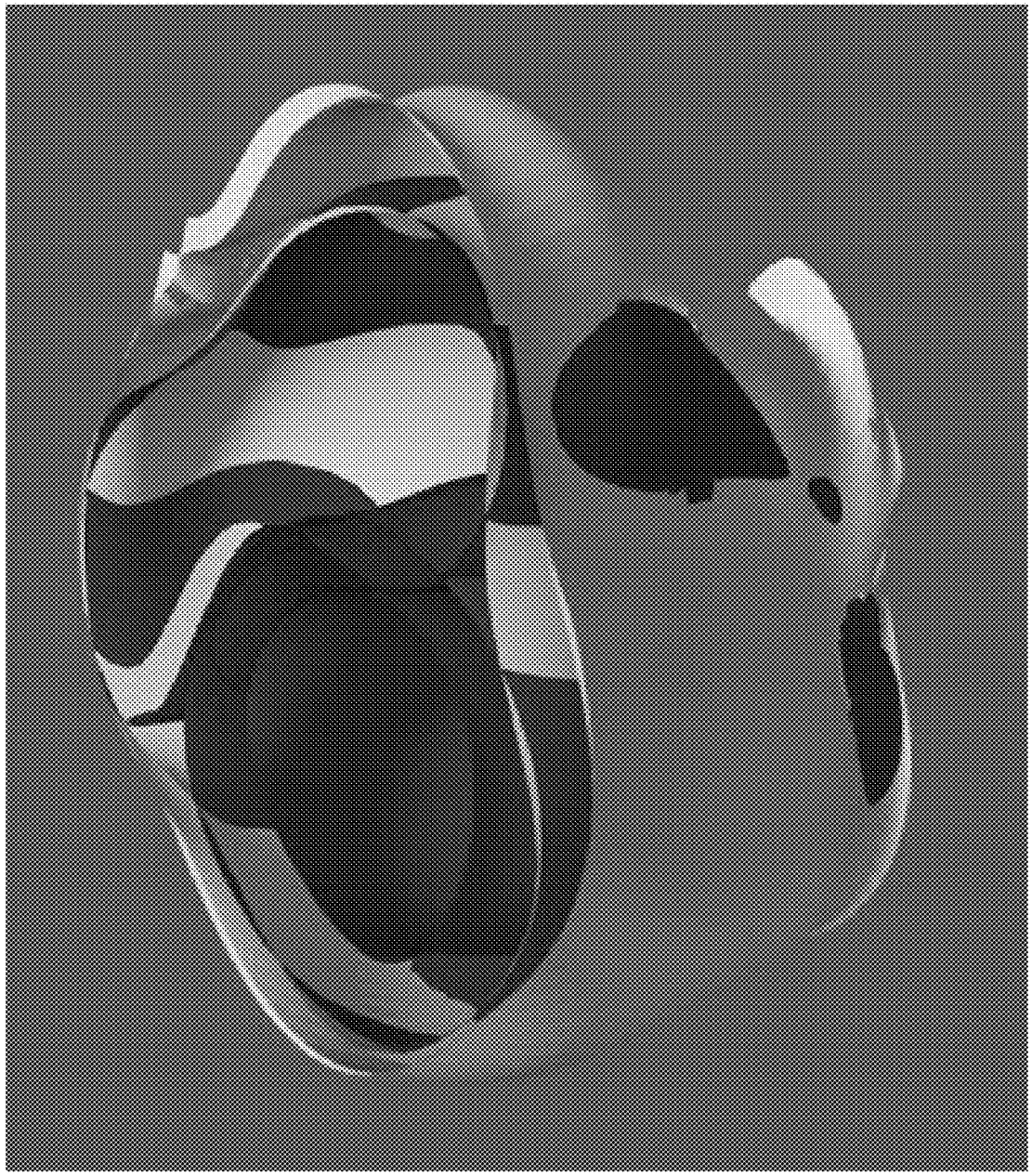
FIG. 35 shows an example fat surface displayed in conjunction with the 3D myocardium surface to accentuate the relationship between the heart and its associated cardiac fat.

Iteration of the above process for each of the v parameter slices produces a set of parallel planes containing CAT contours. The lines which connect the points of these contours (yellow lines in FIG. 34A) comprise some of the lines needed to triangulate the points and form a closed surface. However, many of the lines necessary for the triangulation connect points between successive slices. Lines of this type shall be referred to as spanning lines (vertical straight lines connecting slices in FIG. 34B). These spanning lines may be generated through spatial comparison of the points from two consecutive slices. This is facilitated by creating a KD-Tree with the points from a single v parameter slice. The KD-Tree is a data object which enables efficient querying and comparison of points within an n-dimensional space. When the KD-Tree is queried with the points from an adjacent slice, one can quickly determine the closest point matches between slices. Connecting these points provides some of the necessary spanning lines, with most of the resulting lines being nearly or exactly vertical. In the desired triangulation, a typical triangle consists of a vertical spanning line, a diagonal spanning line (the hypotenuse), and a contour line. The vertical spanning line is connected to one end of the contour line. As such, the diagonal spanning line connects the other end of the contour line to the adjacent slice point, completing the triangle. Performing this process for every v parameter slice will produce the set of triangles needed to represent a patient's CAT anatomy in 3D. This fat surface can then be displayed in conjunction with the 3D myocardium surface to accentuate the relationship between the heart and its associated cardiac fat, as shown FIG. 35.

For network training purposes, identifying and segmenting cardiac tissues using echocardiography can be conducted via manual tracing with support of ultrasound cine loops which record motion of the cardiac muscles during scanning. For each scan, a person familiar with cardiac echocardiography identifies three contours, including the left epicardium, left endocardium, and right ventricle. These contours are used to register the ultrasound image plane with the MRI-derived 3D model by through matching of the structures of the left ventricle and left and right myocardium. Based on this registration, the fat that's identified in the cardiac MRI can be used to help train an algorithm to find it in the ultrasound.

Delineated contours from the ultrasound that can be used to link to the MRI-derived model are generated into a label mask using a flood filling technique and binary image subtraction. In the label mask, colors are assigned, e.g., the colors of green, purple and orange are respectively assigned to the left myocardium, left ventricle and right ventricle, respectively.

B-Mode images that are manually traced are originally created from processing raw IQ data with 596 samples per A-line and 201 A-lines. They are scan-converted to the Cartesian domain. Hence, a reverse transformation of the label mask to polar domain is performed which then, used as ground truth label for neural network later.

One of the advantages of raw IQ data is availability of abundant frequency content that can be useful to analyze and extract into many additional spectral features, which can be used to identify cardiac fat that is otherwise not visible in the traditional B-mode image. These additional spectral features can be combined with the normal B-mode pixel intensity to form a multi-dimensional image which is used as input for training of the convolutional neural network in the polar domain. To extract spectral features from raw IQ data, a window of pre-defined size, i.e. 9 rows×3 columns, slides across the entire matrix of IQ data. For ROIs inside the window, the power spectral density (PSD) of the signals are computed and averaged across the ROI. Then they are normalized by subtracting the PSD of the same data collected from a tissue-mimicking phantom. From these average ROI PSDs, 9 spectral features are computed. They included: (1) maximum power (dB), (2) frequency of maximum power (MHz), (3) mean power (dB), (4) slope in dB/MHz of the regression line, (5) y-intercept of the regression line (dB), (6) mid-band power (dB) (based on 20-dB bandwidth of unnormalized PSD), (7) mid-band frequency (MHz), (8) the depth of the ROI (cm), and (9) integrated backscatter (dB): (1) Maximum Power in dB, (2) Frequency at Maximum Power in dB, (3) Mean Power in dB, (4) Normalized Regression Slope of normalized PSD, (5) Normalized y-intercept of normalized PSD, (6) Mid Band Power in dB, (7) Frequency at mid band power (MHz), (8) Depth in cm, (9) Power at zero frequency, (10) Integrated backscatter, and (11) Integrated backscatter in dB. A new image with 10 features for each pixel location is generated, where those bands represent 9 spectral features plus gray-scale pixel intensity.

The multi-dimensional image and label mask are both resized, in this instance, to 256×256 to accommodate the training process. The features are all Z-score normalized. In addition, a Principle Component Analysis is performed with 6 components, representing 95% of the variance of the data.

Figure 36:
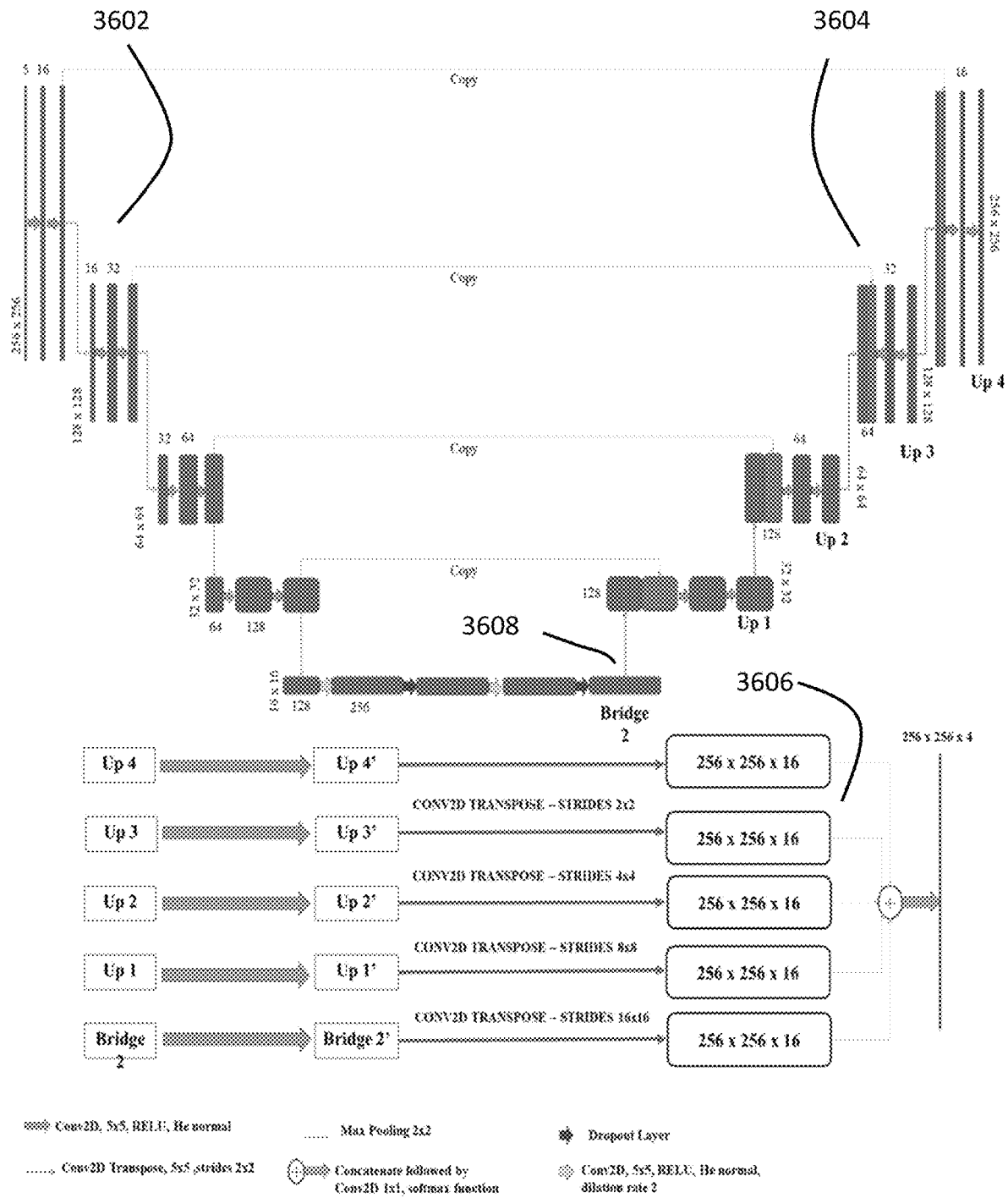
FIG. 36 illustrates a multi-feature Pyramid U-Net network (MFP U-Net) that is a combination of a dilated U-Net and feature pyramid network and can be trained to analyze ultrasound image data and intersect the data with an MRI model.

After the preprocessing step, the multi-dimensional data and label mask is split into a training (80%) and test set (20%) for algorithm training and validation. The training set is passed to a Multi-feature Pyramid U-Net network (MFP U-Net) that is a combination of a dilated U-Net and feature pyramid network and is shown in FIG. 36. Dilated U-Net is a modification of regular U-Net which implements the encoder downward path 3602 and decoder upward path 3604 and uses a regular 2D convolution with dilation rate of 2 for the last layer of the encoding layer. The fully convolutional network (FCN) is designed for feature extraction that can detect objects at different scales. The FCN is integrated into an MFP U-Net whose inputs are outputs of the last encoding level so that strong semantic information of objects after feature layers are upsampled to a fixed dimension 3606 and their sizes are preserved and able to produce more accurate output labels. The MFP U-Net uses 5 levels of encoding and 5 levels of decoding. Each encoder level consists of two convolutional layers with a kernel size of 3×3 and 32 filters, a Rectifier Linear Unit activation function, a He normal kernel initializer, and a 2×2 max pooling layer. However, the last encoder level, called the bridge 3608, has convolution layers with an additional dilation rate of 2 which allows for a wider receptive field of the network. The decoder levels expand encoded feature maps with an upsampling convolutional layer (2×2) and concatenates final output layers at each decoder layer 3606. At the end, all final output feature maps at each decoder level are upsampled to the original input size (240×240) and concatenated into one final layer. The final layer is passed to 1×1 convolutional layer to get probability maps of the number of tissues of the label mask and then converted back to an RGB mask. Two MFP U-Net models are trained to perform two image tasks: the first is to find the bounding box of the entire cluster of tissues and the second is to segment each tissue type from the given multi-dimensional input data. These two models are different in that only one class is used for box detection, but 4 are used for segmentation (background and three cardiac tissue types). The loss function used is binary cross entropy for box detection and categorical cross entropy for the segmentation task. Furthermore, the multi-dimensional data are cropped with a box which finds from their corresponding input label mask.

For reconstruction, the box is predicted first by the MFP U-Net for box detection. That box is then used to crop the data, which is fed to the second MFP U-Net for segmentation. The final segmented output is remapped back with the box coordinates and resized to its original size of (591×201). The resized predicted masks are transformed to Cartesian domain and delineated into a set of three contours of left epicardium, left endocardium, and right ventricle.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims

The invention claimed is:

1. A system for patient cardiac imaging and tissue modeling, comprising:
   an echocardiograph configured to acquire patient 3D cardiac imaging data with raw 2D spectral cardiac imaging data;
   a processor to receive the patient 3D cardiac imaging data with raw 2D spectral cardiac imaging data; and
   software run by the processor to provide the patient 3D cardiac imaging data and the raw 2D spectral cardiac imaging data to a trained learning network to identify a left ventricle, a right ventricle and fat and generate a 3D patient cardiac image labelled with fat; and
   a user interface and display to interact with the patient 3D cardiac image;
   wherein the trained learning network was trained by obtaining training magnetic resonance imaging 3D cardiac imaging data and training echocardiograph 3D cardiac imaging data with training raw 2D spectral cardiac imaging data by using deep learning to find left and right ventricles in the training magnetic resonance imaging 3D cardiac imaging data and training echocardiograph 3D cardiac imaging data, by fitting a training 3D model to a labeled image volume including fat labels, and by registering the training raw 2D spectral cardiac imaging data with the training 3D model.

2. The system of claim 1, comprising analysis software that predicts coronary disease based upon the 3D patient cardiac image labelled with fat based upon fat tissue mapped in locations near coronary arteries.

3. The system of claim 2, wherein the analysis software compares the fat tissue mapped in locations near coronary arteries to a database of coronary plaque obtained by intravascular ultrasound.

4. The system of claim 1, wherein the registering the training raw 2D spectral cardiac imaging data with the training 3D model comprises using segmented structures in the raw 2D spectral cardiac imaging data and aligning contours from the patient 3D cardiac imaging data with the surfaces of the training 3D model.

* * * * *